United States Patent
Wu

(10) Patent No.: US 9,803,017 B2
(45) Date of Patent: Oct. 31, 2017

(54) SOLUBLE MIC NEUTRALIZING MONOCLONAL ANTIBODY FOR TREATING CANCER

(71) Applicant: UNIVERSITY OF WASHINGTON THROUGH ITS CENTER FOR COMMERCIALIZATION, Seattle, WA (US)

(72) Inventor: Jennifer Wu, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 14/900,510

(22) PCT Filed: Jul. 3, 2014

(86) PCT No.: PCT/US2014/045366
§ 371 (c)(1),
(2) Date: Dec. 21, 2015

(87) PCT Pub. No.: WO2015/003114
PCT Pub. Date: Jan. 8, 2015

(65) Prior Publication Data
US 2016/0368991 A1    Dec. 22, 2016

Related U.S. Application Data

(60) Provisional application No. 61/843,182, filed on Jul. 5, 2013, provisional application No. 61/893,734, filed on Oct. 21, 2013.

(51) Int. Cl.
*C07K 16/28* (2006.01)
*A01K 67/027* (2006.01)
*C07K 16/30* (2006.01)
*A61K 39/00* (2006.01)

(52) U.S. Cl.
CPC ...... *C07K 16/2833* (2013.01); *A01K 67/0278* (2013.01); *C07K 16/2851* (2013.01); *C07K 16/30* (2013.01); *A01K 2217/072* (2013.01); *A01K 2227/105* (2013.01); *A01K 2267/0331* (2013.01); *A61K 2039/505* (2013.01); *C07K 2317/24* (2013.01); *C07K 2317/31* (2013.01); *C07K 2317/51* (2013.01); *C07K 2317/515* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/624* (2013.01); *C07K 2317/626* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,518,584 A | 5/1985 | Mark et al. |
| 4,634,664 A | 1/1987 | Oestberg |
| 4,634,666 A | 1/1987 | Engleman et al. |
| 4,737,462 A | 4/1988 | Mark et al. |
| 4,946,778 A | 8/1990 | Ladner et al. |
| 5,225,539 A | 7/1993 | Winter |
| 5,304,489 A | 4/1994 | Rosen |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,733,743 A | 3/1998 | Johnson et al. |
| 5,741,957 A | 4/1998 | Deboer et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,837,242 A | 11/1998 | Holliger et al. |
| 5,849,992 A | 12/1998 | Meade et al. |
| 5,858,657 A | 1/1999 | Winter et al. |

(Continued)

FOREIGN PATENT DOCUMENTS

| | | |
|---|---|---|
| EP | 3016683 A1 | 5/2016 |
| WO | 87/02671 A1 | 5/1987 |
| WO | 90/07861 A1 | 7/1990 |
| WO | 91/10741 A1 | 7/1991 |
| WO | 91/17271 A1 | 11/1991 |
| WO | 92/01047 A1 | 1/1992 |
| WO | 92/22653 A1 | 12/1992 |
| WO | 93/12227 A1 | 6/1993 |
| WO | 01/29242 A2 | 4/2001 |
| WO | 03/063792 A2 | 8/2003 |
| WO | 2012/078014 A1 | 6/2012 |
| WO | 2015/085210 A1 | 6/2015 |
| WO | 2015/139020 A2 | 9/2015 |

OTHER PUBLICATIONS

Mariuzza (Annu. Rev. Biophys. Biophys. Chem., 16: 139-159, 1987).*
Acheampong et al., "Obstructing Shedding of Mic: The Way Forward for Cancer Treatment", IJPBS, 3(1):55-62 (2013).

(Continued)

*Primary Examiner* — Brad Duffy
*Assistant Examiner* — Nelson B Moseley, II
(74) *Attorney, Agent, or Firm* — Nixon Peabody LLP; Mark J. FitzGerald; Nicole D. Kling

(57) ABSTRACT

Disclosed are compositions and methods relating to antibodies that bind soluble Major Histocompatibility Complex class I chain-related (sMIC). Specifically, disclosed are antibodies designed or selected to inhibit sMIC (e.g. to neutralize sMIC) shed from MIC+ tumors. Further disclosed are methods of using the antibodies for the treatment of MIC-positive cancers.

16 Claims, 23 Drawing Sheets

(56) References Cited

U.S. PATENT DOCUMENTS

| | | |
|---|---|---|
| 5,871,907 A | 2/1999 | Winter et al. |
| 5,874,299 A | 2/1999 | Lonberg et al. |
| 5,877,218 A | 3/1999 | Herzig et al. |
| 5,877,397 A | 3/1999 | Lonberg et al. |
| 6,080,560 A | 6/2000 | Russell et al. |
| 6,512,162 B2 | 1/2003 | McBride et al. |
| 6,824,989 B1 | 11/2004 | Eisinger et al. |
| 6,835,823 B2 | 12/2004 | Le et al. |
| 6,852,318 B1 | 2/2005 | Varner |
| 6,890,958 B2 | 5/2005 | Sikorski et al. |
| 6,936,428 B2 | 8/2005 | Davis et al. |
| 6,972,198 B2 | 12/2005 | Craig et al. |
| 7,413,862 B2 | 8/2008 | Van Dongen et al. |
| 7,666,417 B2 | 2/2010 | Spies et al. |
| 7,771,718 B2 | 8/2010 | Spies et al. |
| 7,959,916 B2 | 6/2011 | Spies et al. |
| 8,182,809 B1 | 5/2012 | Wu |
| 8,329,660 B2 | 12/2012 | Kuchroo et al. |
| 8,753,640 B2 | 6/2014 | Wu |
| 9,402,905 B2 | 8/2016 | Wucherpfennig et al. |
| 2003/0105000 A1 | 6/2003 | Pero et al. |
| 2003/0167531 A1 | 9/2003 | Russell et al. |
| 2006/0270045 A1 | 11/2006 | Cregg et al. |
| 2007/0248607 A1 | 10/2007 | Spies et al. |
| 2009/0123921 A1 | 5/2009 | Georgiou et al. |
| 2009/0136516 A1 | 5/2009 | Tedder et al. |
| 2009/0169552 A1 | 7/2009 | Spies et al. |
| 2009/0275124 A1 | 11/2009 | Muruganandam et al. |
| 2010/0111973 A1 | 5/2010 | Dranoff et al. |
| 2011/0117086 A1 | 5/2011 | Pannequin et al. |
| 2011/0123541 A1 | 5/2011 | Bachmann et al. |
| 2012/0195831 A1 | 8/2012 | Zhang et al. |
| 2012/0315287 A1 | 12/2012 | Wu |
| 2014/0322244 A1 | 10/2014 | Wu |
| 2014/0377266 A1 | 12/2014 | Spies et al. |
| 2016/0264673 A1 | 9/2016 | Wu |

OTHER PUBLICATIONS

Bowers et al., "Coupling mammalian cell surface display with somatic hypermutation for the discovery and maturation of human antibodies", PNAS, 108(51):20455-20460 (2011).

Bowers et al., "Humanization of Antibodies Using Heavy Chain Complementarity-determining Region 3 Grafting coupled with in Vitro Somatic Hypermutation", The Journal of Biological Chemistry, 288(11):7688-7696 (2013).

Willis et al., "Human Germline Antibody Gene Segments Encode Polyspecific Antibodies", PLOS Computational Biology, 9(4):e1003045 (2013).

Andrabi et al., "Cross-neutralizing activity of human anti-V3 monoclonal antibodies derived from non-B Glade HIV-1 infected individuals." Virology 439(2):81-88 (2013).

Barderas et al., "Affinity maturation of antibodies assisted by in silico modeling." PNAS 105(26):9029-9034 (2008).

Brown et al., "Tolerance of Single, but Not Multiple, Amino Acid Replacements in Antibody VH CDR2" The Journal of Immunology 156(9):3285-3291 (1996).

Jinushi et al., "Therapy-induced antibodies to MHC class I chain-related protein a antagonize immune suppression and stimulate antitumor cytotoxicity." PNAS 103(24):9190-9195 (2006).

Maynard et al., "Protection against anthrax toxin by recombinant antibody fragments correlates with antigen affinity." Mature Biotechnology 20(6):597-601 (2002).

Winkler et al., "Changing the Antigen Binding Specificity by Single Point Mutations of an Anti-p24 (HIV-1) Antibody." The Journal of Immunology 165(8):4505-4514 (2000).

Abaza et al. "Effects of amino acid substitutions outside an antigenic site on protein binding to monoclonal antibodies of predetermined specificity obtained by peptide immunization: demonstration with region 94-100 (antigenic site 3) of myoglobin," Journal of Protein Chemistry, 11(5):433-444 (1992).

Anderson et al. "Tolerization of tumor-specific T cells despite efficient initial priming in a primary murine model of prostate cancer," Journal of Immunology, 178(3):1268-1276 (2007).

Bae et al. "Metastatic sublines of an SV40 large T antigen immortalized human prostate epithelial cell line," The Prostate, 34(4):275-282 (1998).

Bahram et al. "MIC and Other NKG2D Ligands: From None to Too Many," Current Opinion in Immunology, 17(5):505-509 (2005).

Bahram et al. "Nucleotide sequence of a human MHC class I MICB cDNA," Immunogenetics, 43(4):230-233 (1996).

Bai et al. "Rapid tolerization of virus-activated tumor-specific CD8+ T cells in prostate tumors of TRAMP mice," PNAS 105(35):13003-13008 (2008).

Bauer et al. "A genetic enrichment for mutations constructed by oligodeoxynucleotide-directed mutagenesis," Gene, 37(1-3):73-81 (1985).

Bauer et al. "Activation of NK cells and T cells by NKG2D, a receptor for stress-inducible MICA," Science, 285 (5428):727-729 (1999).

Bird et al. "Single-chain antigen-binding proteins," Science, 242(4877):423-426 (1988).

Burgess et al. "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 111(5 Pt 1):2129-2138 (1990).

Busche et al. "Natural killer cell-mediated rejection of experimental human lung cancer by genetic overexpression of major histocompatibility complex class I chain-related gene A," Human Gene Therapy, 17(2):135-146 (2006).

Carayannopoulos et al. "Cutting edge: murine UL16-binding protein-like transcript 1: a newly described transcript encoding a high-affinity ligand for murine NKG2D," Journal of Immunology, 169(8):4079-4083 (2002).

Cerwenka et al. "Ectopic expression of retinoic acid early inducible-1 gene (RAE-1) permits natural killer cell-mediated rejection of a MHC class I-bearing tumor in vivo," PNAS 98(20):11521-11526 (2001).

Cerwenka et al. "NKG2D ligands: unconventional MHC class I-like-molecules exploited by viruses and cancer," Tissue Antigens, 61(5):335-343 (2003).

Cerwenka et al. "Retinoic acid early inducible genes define a ligand family for the activating NKG2D receptor in mice," Immunity, 12(6):721-727 (2000).

Chalk et al. "siRNAdb: a database of siRNA sequences," Nucleic Acids Research, 33(Database issue):D131-D134 (2005).

Champsaur et al. "Effect of NKG2D ligand expression on host immune responses," Immunology Reviews, 235 (1):267-285 (2010).

Chothia et al. "Canonical structures for the hypervariable regions of immunoglobulins," Journal of Molecular Biology, 196(4):901-917 (1987).

Chothia et al. "Conformations of immunoglobulin hypervariable regions," Nature, 342(6252):877-883 (1989).

Co et al. "Chimeric and Humanized Antibodies with Specificity for the CD33 Antigen," Journal of Immunology, 148 (a):1149-1154 (1992).

Coburn et al. "Potent and specific inhibition of human immunodeficiency virus type 1 replication by RNA interference," Journal of Virology, 76(18):9225-9231 (2002).

Colman et al. "Effects of amino acid sequence changes on antibody-antigen interactions," Research in Immunology, 145(1):33-36 (1994).

Cortes et al. "An Unusually Large Multifunctional Polypeptide in the Erythromycin-producing Polyketide Synthase of Saccharopolyspora erythraea," Nature, 348(6297):176-178 (1990).

Cosman et al. "ULBP3, a novel MHC class I-related molecules, bind to CMV glycoprotein UL16 and stimulate NK cytotoxicity through the NKG2D receptor," Immunity, 14(2):123-133 (2001).

Coudert et al. "Altered NKG2D function in NK cells induced by chronic exposure to NKG2D ligand-expressing tumor cells," Blood, 106(5):1711-1717 (2005).

(56) References Cited

OTHER PUBLICATIONS

Craik et al. "Use of Oligonucleotides for Site-Specific Mutagenesis," BioTechniques, 3:12-19 (1985).
De Kruijf et al. "NKG2D ligand tumor expression and association with clinical outcome in early breast cancer patients: an observational study," BMC Cancer, 12:24 (2012).
Degrassi et al. "Magnetic resonance imaging and histopathological characterization of prostate tumors in TRAMP mice as model for pre-clinical trials," Prostate 67(4):396-404 (2007).
Diefenbach et al. "A novel ligand for the NKG2D receptor activates NK cells and macrophages and induces tumor immunity," European Journal of Immunology, 33(2):381-391 (2003).
Diefenbach et al. "Ligands for the murine NKG2D receptor: expression by tumor cells and activation of NK cells and macrophages," Nature Immunology, 1(2):119-126 (2000).
Diefenbach et al. "Rae1 and H60 ligands of the NKG2D receptor stimulate tumour immunity," Nature, 413 (6852):165-171 (2001).
Diefenbach et al. "Selective associations with signaling proteins determine stimulatory versus costimulatory activity of NKG2D," Nature Immunology, 3(12):1142-1149 (2002).
Diefenbach et al. "The innate immune response to tumors and its role in the induction of T-cell immunity," Immunological Reviews, 188:9-21 (2002).
Donadio et al. "Modular Organization of Genes Required for Complex Polyketide Biosynthesis," Science, 252 (5006):675-679 (1991).
Doubrovina et al. "Evasion from NK cell immunity by MHC class I chain-related molecules expressing colon adenocarcinoma," Journal of Immunology, 171(12):6891-6899 (2003).
Duan et al. "Clinical significance of the immunostimulatory MHC class I chain-related molecule A and NKG2D receptor on NK cells in pancreatic cancer," Medical Oncology, 28(2):466-474 (2011).
Dunn et al. "Human cytomegalovirus glycoprotein UL16 causes intracellular sequestration of NKG2D ligands, protecting against natural killer cell cytotoxicity," Journal of Experimental Medicine, 197(11):1427-1439 (2003).
Elbashir et al. "Duplexes of 21-nucleotide RNAs mediate RNA interference in cultured mammalian cells," Nature, 411(6836):494-498 (2001).
Elbashir et al. "RNA interference is mediated by 21- and 22-nucleotide RNAs," Genes & Development, 15 (2):188-200 (2001).
Ellington et al. "In vitro selection of RNA molecules that bind specific ligands," Nature, 346(6287):818-822 (1990).
Endo et al. "High-throughput, genome-scale protein production method based on the wheat germ cell-free expression system," Biotechnology Advances, 21(8):695-713 (2003).
Extended European Search Report dated Jan. 20, 2017 for EP 14819961.5.
Foster et al. "Characterization of prostatic epithelial cell lines derived from transgenic adenocarcinoma of the mouse prostate (TRAMP) model," Cancer Research, 57(16):3325-3330 (1997).
Friese et al. "MICA/NKG2D-mediated immunogene therapy of experimental gliomas," Cancer Research, 63 (24):8996-9006 (2003).
Fujii et al. "Antibody affinity maturation by random mutagenesis," Methods in Molecular Biology: Antibody Engineering, 248:345-349 (2004).
Galon et al. "Type, density, and location of immune cells within human colorectal tumors predict clinical outcome," Science, 313(5795):1960-1964 (2006).
Gasser et al. "The DNA damage pathway regulates innate immune system ligands of the NKG2D receptor," Nature, 436(7054):1186-1190 (2005).
Gingrich et al. "Pathologic progression of autochthonous prostate cancer in the TRAMP model," Prostate Cancer and Prostatic Diseases, 2(2):70-75 (1999).
Girlanda et al. "MICA expressed by multiple myeloma and monoclonal gammoapthy of undetermined significance plasma cells Costimulates pamidronate-activated gammadelta lymphocytes," Cancer Research, 65(16):7502-7508 (2005).
Gorman et al. "The Rous sarcoma virus long terminal repeat is a strong promoter when introduced into a variety of eukaryotic cells by DNA-mediated transfection," PNAS 79(22):6777-6781 (1982).
Greenberg et al. "Prostate cancer in a transgenic mouse," Proceedings of the National Academy of Sciences USA, 92(8):3439-3443 (1995).
Groh et al. "Broad tumor-associated expression and recognition by tumor-derived gamma delta T cells of MICA and MICB," Proceedings of the National Academy of Sciences USA, 96(12):6879-6884 (1999).
Groh et al. "Costimulation of CD8alphabeta T cells by NKG2D via engagement by MIC induced on virus-infected cells," Nature Immunology, 2(3):255-260 (2001).
Groh et al. "Recognition of stress-induced MHC molecules by intestinal epithelial gammadelta T cells," Science, 279 (5357):1737-1740 (1998).
Groh et al. "Tumour-derived soluble MIC ligands impair expression of NKG2D and T-cell activation," Nature, 419 (6908):734-738 (2002).
Grosschedl et al. "Cell-type specificity of immunoglobulin gene expression is regulated by at least three DNA sequence elements," Cell, 41(3):885-897 (1985).
Grossmann et al. "Expression, specificity and immunotherapy potential of prostate-associated genes in murine cell lines," World Journal of Urology, 19(5):365-370 (2001).
Guerra et al. "NKG2D-deficient mice are defective in tumor surveillance in models of spontaneous malignancy," Immunity, 28(4):571-580 (2008).
Gulubova et al. "Decrease in intrahepatic CD56+ lymphocytes in gastric and colorectal cancer patients with liver metastases," APMIS: Acta Pathologica, Microbiologica, et Immunologica Scandinavica, 117(12):870-879 (2009).
Gura "Systems for identifying new drugs are often faulty," Science, 278(5340):1041-1042 (1997).
Harborth et al. "Identification of essential genes in cultured mammalian cells using small interfering RNAs," Journal of Cell Science, 114(Pt 24):4557-4565 (2001).
Hayakawa "Targeting NKG2D in tumor surveillance," Expert Opinion on Therapeutic Targets, 16(6):587-599 (2012).
Hermann et al. "Adaptive recognition by nucleic acid aptamers," Science, 287(5454):820-825 (2000).
Hitzeman et al. "Expression, processing, and secretion of heterologous gene products by yeast," Berkeley Workshop on Recent Advances in Yeast Molecular Biology: Recombinant DNA, Lawrence Berkeley Laboratory, University of California, Berkeley, CA, 1:173-190 (1982).
Ho et al. "Costimulation of multiple NK cell activation receptors by NKG2D," Journal of Immunology, 169(7):3667-3675 (2002).
Holdenrieder et al. "Soluble MICA in malignant diseases," International Journal of Cancer, 118(3):684-687 (2006).
Holdenrieder et al. "Soluble MICB in malignant diseases: analysis of diagnostic significance and correlation with soluble MICA," Cancer Immunology, Immunotherapy, 55(12):1584-1589 (2006).
Holdenrieder et al. "Soluble NKG2D ligands in hepatic autoimmune diseases and in benign diseases involved in marker metabolism," Anticancer Research, 27(4A):2041-2045 (2007).
Holliger et al. "'Diabodies': small bivalent and bispecific antibody fragments," PNAS 90(14):6444-6448 (1993).
Holmes et al. "Structural studies of allelic diversity of the MHC class I homolog MIC-B, a stress-inducible ligand for the activating immunoreceptor NKG2D," Journal of Immunology, 169(3):1395-1400 (2002).
Horton et al. "Gene splicing by overlap extension: tailor-made genes using the polymerase chain reaction," Biotechniques, 8(5):528-535 (1990).
Hunkapiller et al. "The growing immunoglobulin gene superfamily," Nature, 323(6083):15-16 (1986).
Huse et al. "Generation of a Large Combinatorial Library of the Immunoglobulin Repertoire in Phage Lambda," Science, 246(4935):1275-1281 (1989).
Huston et al. "Protein engineering of antibody binding sites: recovery of specific activity in an anti-digoxin single-chain Fv analogue produced in *Escherichia coli*," PNAS 85(16):5879-5883 (1988).

(56) References Cited

OTHER PUBLICATIONS

International Search Report and Written Opinion dated Nov. 21, 2014 for PCT/US2014/045366 filed Jul. 3, 2014, 14 pages.
Jackson et al. "Expression profiling reveals off-target gene regulation by RNAi," Nature Biotechnology, 21 (6):635-637 (2003).
Jinushi et al. "Expression and role of MICA and MICB in human hepatocellular carcinomas and their regulation by retinoic acid," International Journal of Cancer, 104(3):354-361 (2003).
Jinushi et al. "MHC class I chain-related protein A antibodies and shedding are associated with the progression of multiple myeloma," PNAS 105(4):1285-1290 (2008).
Kabat et al. "Attempts to locate complementarity-determining residues in the variable positions of light and heavy chains," Annals of the New York Academy of Sciences, 190:382-393 (1971).
Kaiser "Cancer. First pass at cancer genome reveals complex landscape," Science, 313(5792):1370 (2006).
Kaiser et al. "Disulphide-isomerase-enabled shedding of tumour-associated NKG2D ligands," Nature, 447 (7143):482-486 (2007).
Kaplan-Lefko et al. "Pathobiology of autochthonous prostate cancer in a pre-clinical transgenic mouse model," The Prostate, 55(3):219-237 (2003).
Kipriyanov et al. "Recombinant single-chain Fv fragments carrying C-terminal cysteine residues: production of bivalent and biotinylated miniantibodies," Molecular Immunology, 31(14):1047-1058 (1994).
Kipriyanov et al. "Single-chain antibody streptavidin fusions: tetrameric bifunctional scFv-complexes with biotin binding activity and enhanced affinity to antigen," Human Antibodies and Hybridomas, 6(3):93-101 (1995).
Kostelny et al. "Formation of a bispecific antibody by the use of leucine zippers," Journal of Immunology, 148 (5):1547-1553 (1992).
Anzavecchia et al. "The use of hybrid hybridomas to target human cytotoxic T lymphocytes," European Journal of Immunology, 17(1):105-111 (1987).
Lazar et al. "Transforming growth factor alpha: mutation of aspartic acid 47 and leucine 48 results in different biological activities," Molecular and Cellular Biology, 8(3):1247-1252 (1998).
Le Maux Chansac et al. "Potentiation of NK cell-mediated cytotoxicity in human lung adenocarcinoma: role of NKG2D-dependent pathway," International Immunology, 20(7):801-810 (2008).
Li et al. "Complex structure of the activating immunoreceptor NKG2D and its MHC class I-like ligand MICA," Nature Immunology, 2(5):443-451 (2001).
Li et al. "Crystal structure of the MHC class I homolog MIC-A, a gammadelta T cell ligand," Immunity, 10(5):577-584 (1999).
Liu et al. "The membrane type matrix metalloproteinase MMP14 mediates constitutive shedding of MHC class I chain-related molecule A independent of A disintegrin and metalloproteinases," Journal of Immunology, 184(7):3346-3350 (2010).
Long "Tumor cell recognition by natural killer cells," Seminars in Cancer Biology, 12(1):57-61 (2002).
Long "Versatile signaling through NKG2D," Nature Immunology, 3(12):1119-1120 (2002).
Maccallum et al. "Antibody-antigen interactions: contact analysis and binding site topography," Journal of Molecular Biology, 262(5):732-745 (1996).
MacNeil et al. "Complex Organization of the Streptomyces avermitilis Genes Encoding the Avermectin Polyketide Synthase," Gene, 115(1-2):119-125 (1992).
Madjd et al. "Upregulation of MICA on high-grade invasive operable breast carcinoma," Cancer Immunity, 7:17 (2007).
Marten et al., "Soluble MIC is Elevated in the Serum of Patients with Pancreatic Carcinoma Diminishing Gamma Delta T Cell Cytotoxicity," Int J Cancer 119(10):2359-65 (2006).
Masters et al. "Short tandem repeat profiling provides an international reference standard for human cell lines" PNAS 98:8012-8017 (2001).

Masuda et al. "High levels of RAE-I isoforms on mouse tumor cell lines assessed by anti-"pan" RAE-I antibody confer tumor susceptibility to NK cells," Biochemical and Biophysical Research Communications, 290(1):140-145 (2002).
McGilvray et al. "NKG2D ligand expression in human colorectal cancer reveals associations with prognosis and evidence for immunoediting," Clinical Cancer Research, 15(22):6993-7002 (2009).
Wang et al. "An six-amino acid motif in the alpha3 domain of MICA is the cancer therapeutic target to inhibit shedding," Biochemical and Biophysical Research Communications, 387(3):476-481 (2009).
Ward et al. "Binding activities of a repertoire of single immunoglobulin variable domains secreted from *Escherichia coli*," Nature, 341(6242):544-546 (1989).
Watson et al. "Expression of the stress-related MHC class I chain-related protein MICA is an indicator of good prognosis in colorectal cancer patients," International Journal of Cancer, 118(6):1445-1452 (2006).
Weidle et al. "Reconstitution of functionally active antibody directed against creatine kinase from separately expressed heavy and light chains in non-lymphoid cells," Gene, 51(1):21-29 (1987).
Whittle et al. "Expression in COS cells of a mouse-human chimaeric B72.3 antibody," Protein Engineering, 1 (6):499-505 (1987).
Wiemann et al. "Systemic NKG2D down-regulation impairs NK and CD8 T cell responses in vivo," Journal of Immunology, 175(2):720-729 (2005).
Wu et al. "An activating immunoreceptor complex formed by NKG2D and DAP10," Science, 285(5428):730-732 (1999).
Wu et al. "Intracellular retention of the MHC class I-related chain B ligand of NKG2D by the human cytomegalovirus UL16 glycoprotein," Journal of Immunology, 170(8):4196-4200 (2003).
Wu et al. "Obstructing shedding of the immunostimulatory MHC class I chain-related gene B prevents tumor formation," Clinical Cancer Research, 15(2):632-640 (2009).
Wu et al. "Oxidative DNA damage in the prostate may predispose men to a higher risk of prostate cancer," Translational Oncology, 2(1):39-45 (2009).
Wu et al. "Prevalent expression of the immunostimulatory MHC class I chain-related molecule is counteracted by shedding in prostate cancer," Journal of Clinical Investigation, 114(4):560-568 (2004).
Wu et al. "T cell antigen receptor engagement and specificity in the recognition of stress-inducible MHC class I-related chains by human epithelial gamma delta T cells," Journal of Immunology, 169(3):1236-1240 (2002).
Yi et al. "A microcapillary trap cartridge-microcapillary high-performance liquid chromatography electrospray ionization emitter device capable of peptide tandem mass spectrometry at the attomole level on an ion trap mass spectrometer with automated routine operation," Rapid Communications in Mass Spectometry, 17(18):2093-2098 (2003).
Zompi et al. "NKG2D triggers cytotoxicity in mouse NK cells lacking DAP12 or Syk family kinases," Nature Immunology, 4(6):565-572 (2003).
McGilvray et al. "ULBP2 and RAET1E NKG2D ligands are independent predictors of poor prognosis in ovarian ancer patients," International Journal of Cancer, 127(6):1412-1420 (2010).
Miller et al. "Cloning and Expression of a Yeast Ubiquitin-Protein Cleaving Activity in *Escherichia Coli*," Nature Biotechnology, 7:698-704 (1989).
Morrison et al. "Chimeric human antibody molecules: mouse antigen-binding domains with human constant region domains," PNAS 81(21):6851-6855 (1984).
Nausch et al. "NKG2D ligands in tumor immunity," Oncogene, 27(45):5944-5958 (2008).
Neuberger "Generating High-avidity Human Mabs in Mice," Nature Biotechnology, 14(7):826 (1996).
Neuberger et al. "Recombinant antibodies possessing novel effector functions," Nature, 312(5995):604-608 (1984).

(56) References Cited

OTHER PUBLICATIONS

Nicolaou et al. "Calicheamicin θ : A Rationally Designed Molecule with Extremely Potent and Selective DNA Cleaving Properties and Apoptosis Inducing Activity," Angewandte Chemie International Edition, 33(2):183-186 (1994).
Nunn et al. "Comparison of a *Salmonella typhimurium* proteome defined by shotgun proteomics directly on an LTQ-FT and by proteome pre-fractionation on an LCQ-DUO," Briefings in Functional Genomics & Proteomics, 5(2):154-168 (2006).
Ogasawara et al. "Impairment of NK cell function by NKG2D modulation in NOD mice," Immunity, 18(1):41-51 (2003).
Okayama et al. "A cDNA cloning vector that permits expression of cDNA inserts in mammalian cells," Molecular and Cellular Biology, 3(2):280-289 (1983).
Oppenheim et al. "Sustained localized expression of ligand for the activating NKG2D receptor impairs natural cytotoxicity in vivo and reduces tumor immunosurveillance," Nature Immunology, 6(9):928-937 (2005).
Ostberg et al. "Human X (Mouse X Human) Hybridomas Stably Producing Human antibodies," Hybridoma, 2(4):361-367 (1983).
Padlan et al. "Identification of specificity-determining residues in antibodies," FASEB Journal, 9(1):133-139 (1995).
Perentes et al. "Cancer cell-associated MT1-MMP promotes blood vessel invasion and distant metastasis in triple-negative mammary tumors," Cancer Research, 71(13):4527-4538 (2011).
Poljak "Production and structure of diabodies," Structure, 2(12):1121-1123 (1994).
Queen et al. "A humanized antibody that binds to the interleukin 2 receptor," PNAS 86(24):10029-10033 (1989).
Queen et al. "Cell-type Specific Regulation of a Kappa Immunoglobulin Gene by Promoter and Enhancer Elements," Immunological Reviews, 89:49-68 (1986).
Raffaghello et al. "Downregulation and/or release of NKG2D ligands as immune evasion strategy of human neuroblastoma," Neoplasia, 6(5):558-568 (2004).
Raulet "Roles of the NKG2D immunoreceptor and its ligands," Nature Reviews Immunology, 3(10):781-790 (2003).
Rebmann et al. "Soluble MICA as an independent prognostic factor for the overall survival and progression-free survival of multiple myeloma patients," Clinical Immunology, 123(1):114-120 (2007).
Ren et al. "Cancer gene therapy using mesenchymal stem cells expressing interferon-beta in a mouse prostate cancer ung metastasis model," Gene Therapy, 15(21):1446-1453 (2008).
Rudikoff et al. "Single amino acid substitution altering antigen-binding specificity," Proceedings of the National Academy of Sciences USA, 79(6):1979-1983 (1982).
Sabin et al. "High-Level Expression and In Vivo Processing of Chimeric Ubiquitin Fusion Proteins in *Saccharomyces cerevisiae*," Nature Biotechnology, 7:705-709 (1989).
Salagianni et al. "New insights into the role of NK cells in cancer immunotherapy," Oncoimmunology, 1(2):205-207 (2012).
Salih et al. "Functional expression and release of ligands for the activating immunoreceptor NKG2D in leukemia," Blood, 102(4):1389-1396 (2003).
Salih et al. "Cutting edge: down-regulation of MICA on human tumors by proteolytic shedding," Journal of Immunology, 169(8):4098-4102 (2002).
Salih et al. "Release of MICB molecules by tumor cells: mechanism and soluble MICB in sera of cancer patients," Human Immunology, 67(3):188-195 (2006).
Sconocchia et al. "Defective infiltration of natural killer cells in MICA/B-positive renal cell carcinoma involves beta (2)-integrain-mediated interaction," Neoplasia, 11(7):662-671 (2009).

Seliger et al. "HLA-G and MIC expression in tumors and their role in anti-tumor immunity," Trends in Immunology, 24(2):82-87 (2003).
Sitaraman et al. "High-throughput protein expression using cell-free system," Methods in Molecular Biology, 498:229-244 (2009).
Skerra et al. "Assembly of a functional immunoglobulin Fv fragment in *Escherichia coli*," Science, 242 (4855):1038-1041 (1988).
Smith et al. "Constructed Mutants Using Synthetic Oligodeoxyribonucleotides as Site-Specific Mutagens," in JK Setlow and A. Hollaender (Eds.), Genetic Engineering: Principles and Methods, Plenum Press, 3:1-32 (1981).
Smyth et al. "NKG2D function protects the host from tumor initiation," Journal of Experimental Medicine, 202 (5):583-588 (2005).
Spirin "High-throughput cell-free systems for synthesis of functionally active proteins," Trends in Biotechnology, 22 (10):538-545 (2004).
Steinle et al."Diversification, expression, and gamma delta T cell recognition of evolutionarily distant members of the MIC family of major histocompatibility complex class I-related molecules," PNAS 95(21):12510-12515 (1998).
Strong "Asymmetric ligand recognition by the activating natural killer cell receptor NKG2D, a symmetric homodimer," Molecular Immunology, 38(14):1029-1037 (2002).
Sutherland et al. "The UL16-binding proteins, a novel family of MHC class I-related ligands for NKG2D, activate natural killer cell functions," Immunological Reviews, 181:185-192 (2001).
Suzuki et al. "MUC1 carrying core 2 O-glycans functions as a molecular shield against NK cell attack, promoting bladder tumor metastasis," International Journal of Oncology, 40(6):1831-1838 (2012).
Takeda et al. "Construction of chimaeric processed immunoglobulin genes containing mouse variable and human constant region sequences," Nature, 314(6010):452-454 (1985).
Tamaki et al. "Association between soluble MICA levels and disease stage IV oral squamous cell carcinoma in Japanese patients," Human Immunology, 69(2):88-93 (2008).
Tamaki et al. "Soluble MICB serum levels correlate with disease stage and survival rate in patients with oral squamous cell carcinoma," Anticancer Research, 30(10):4097-4101 (2010).
Tuerk et al. (Aug. 1990) "Systematic evolution of ligands by exponential enrichment: RNA ligands to bacteriophage T4 DNA polymerase," Science, 249(4968):505-510 (1990).
Tuschl et al. "Targeted mRNA degradation by double-stranded RNA in vitro," Genes & Development, 13:3191-3197 (1999).
Tzartos "Epitope mapping by antibody competition. Methodology and Evaluation of the validity of the technique," Methods in Molecular Biology, 66:55-66 (1996).
Varghese et al. "Enhanced therapeutic efficacy of IL-12, but not GM-CSF, expressing oncolytic herpes simplex virus for transgenic mouse derived prostate cancers," Cancer Gene Therapy, 13(3):253-265 (2006).
Vetter et al. "Expression of Stress-induced MHC Class I Related Chain Molecules on Human Melanoma," Journal of Investigative Dermatology, 118(4):600-605 (2002).
Vivier et al. "Targeting natural killer cells and natural killer T cells in cancer," Nature Reviews Immunology, 12 (4):239-252 (2012).
Walder et al. "Oligodeoxynucleotide-directed mutagenesis using the yeast transformation system," Gene, 42 (2):133-139 (1986).
Waldhauer et al. "NK cells and cancer immunosurveillance," Oncogene, 27(45):5932-5943 (2008).
Waldhauer et al. "Tumor-associated MICA is shed by ADAM proteases," Cancer Research, 68(15):6368-6376 (2008).

* cited by examiner

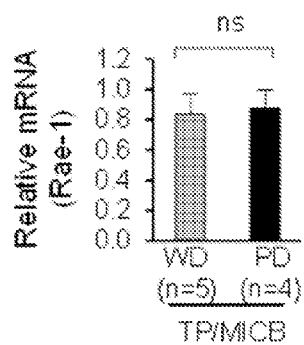
Fig. 2E
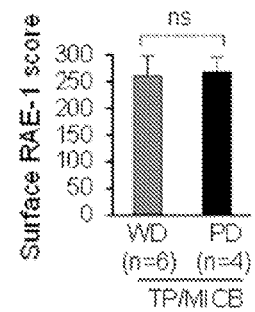
Fig. 2F
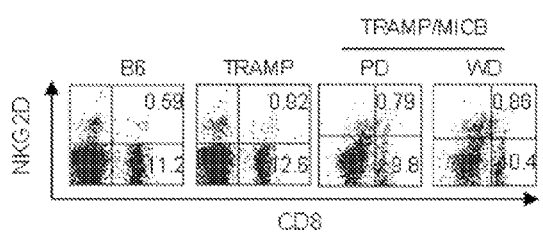
Fig. 3A
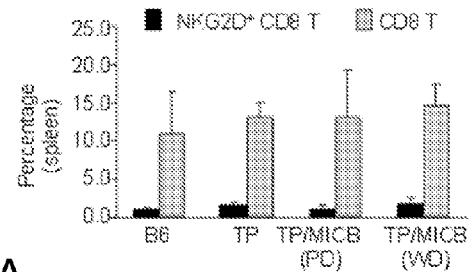
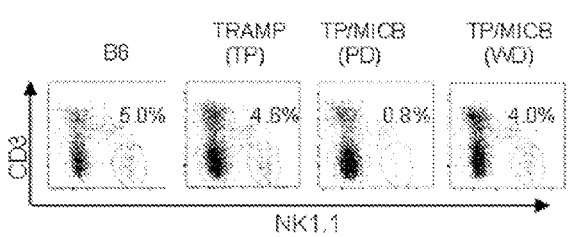
Fig. 3B
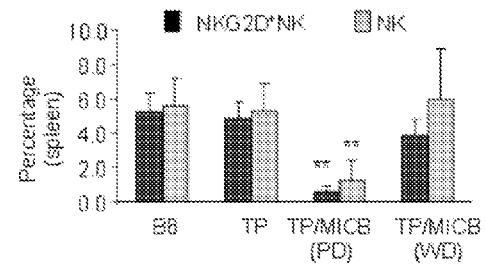

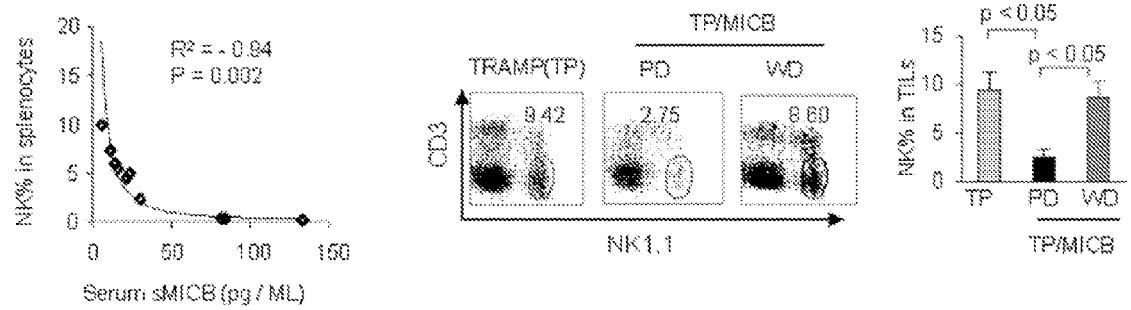
Fig. 3C
Fig. 3E
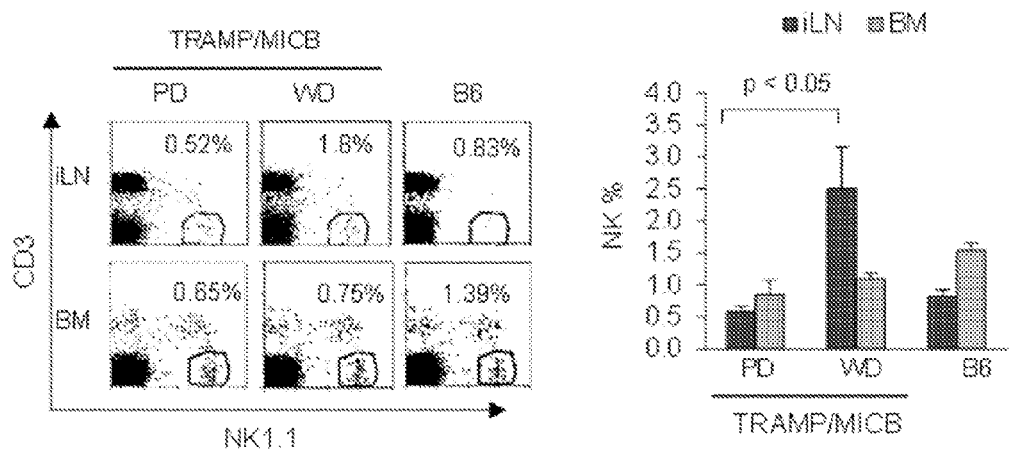
Fig. 3D
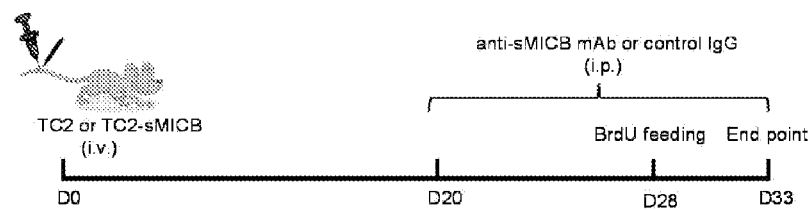
Fig. 4A

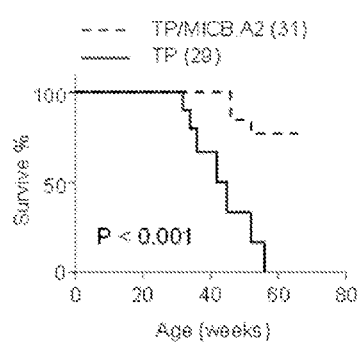
Fig. 6A
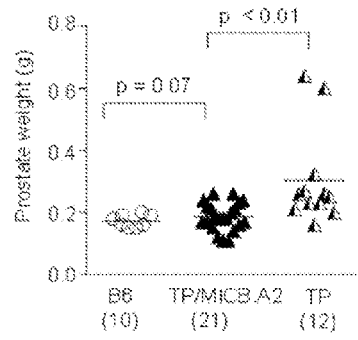
Fig. 6B
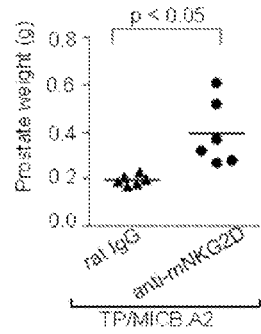
Fig. 6D
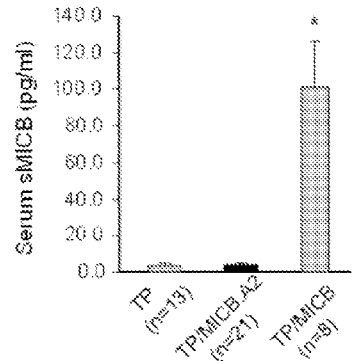
Fig. 6C
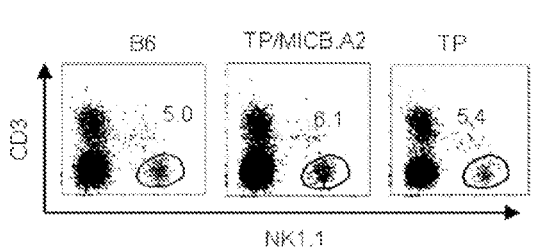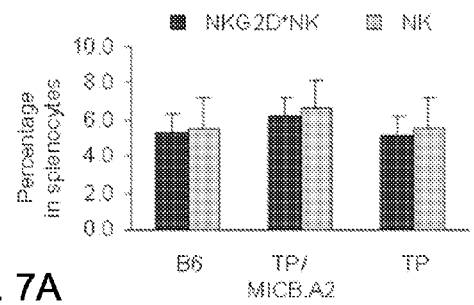
Fig. 7A

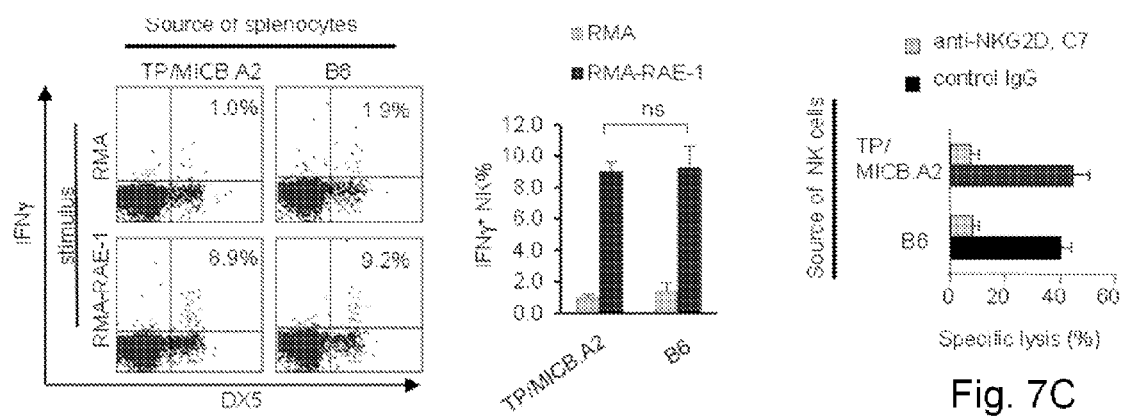
Fig. 7B
Fig. 7C
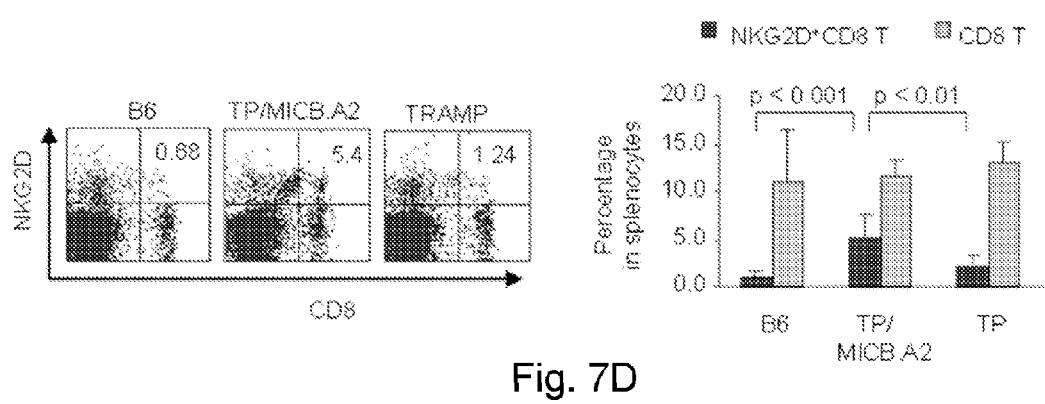
Fig. 7D

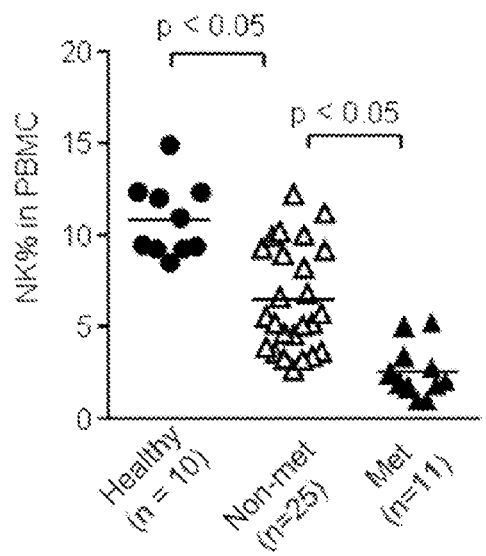 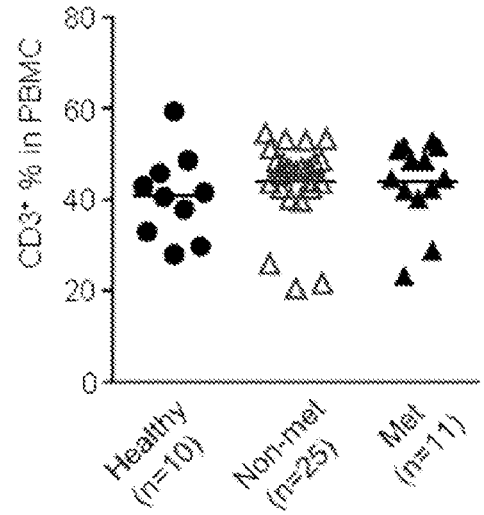
Fig. 8A    Fig. 8B
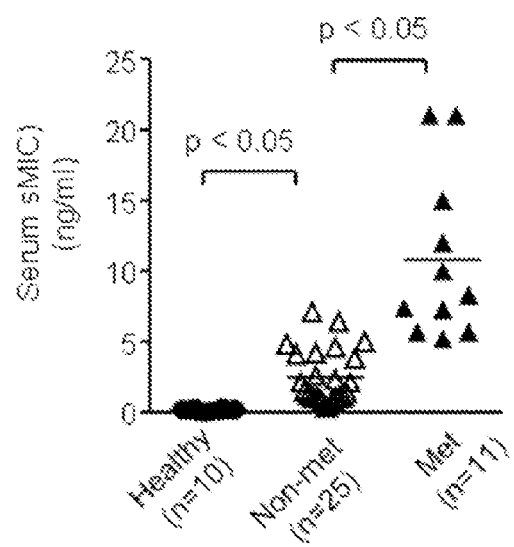 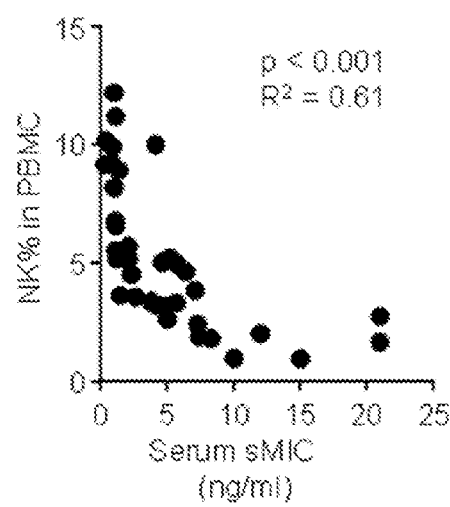
Fig. 8C    Fig. 8D

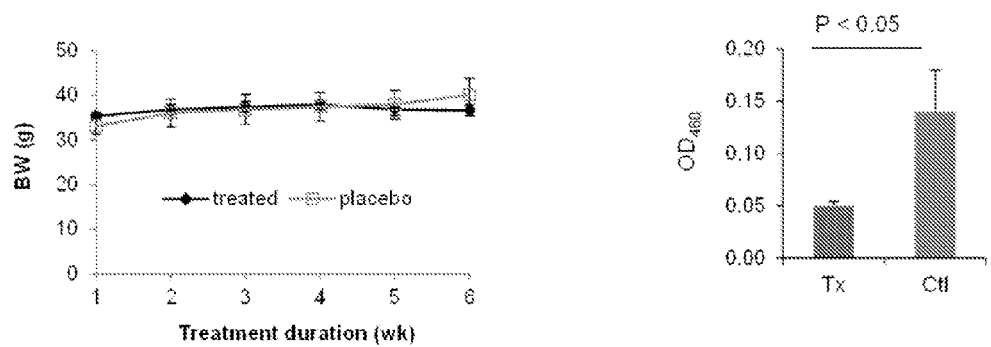
Fig. 10A
Fig. 10C
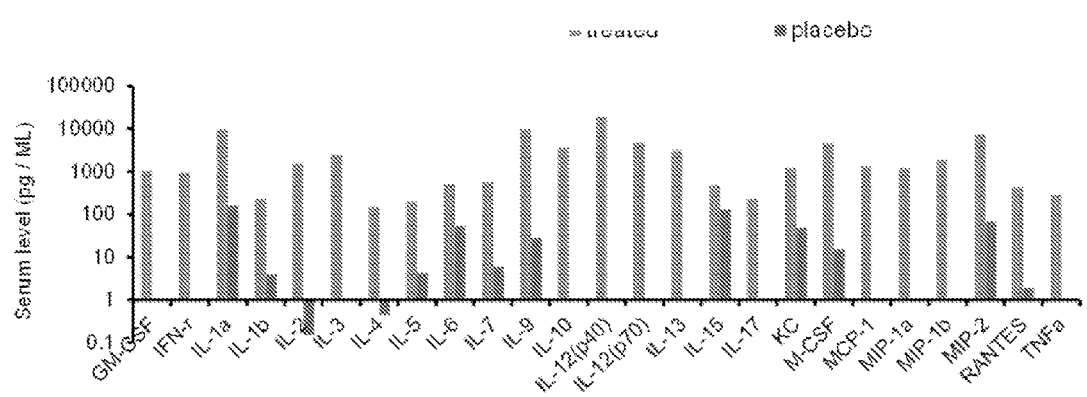
Fig. 10B

IP: p2B10G5 mAb

IB: goat anti-MICB
(R&D systems, AF1599, goat IgG)

1. sMICB only (5 ug / ml)
2. sMICB + 10 ug / ml p2B10G5
3. sMICB + 20 ug / ml p2B10G5
4. sMICB + anti-NKG2D antibody C7 (20 ug/ml)

Antibody Light Chain
>P2B10G5-VL

D I V L T Q T T S Y L S V S L G G R V T I A C K A S A H I N
5'
GACATTGTGCTCACCCAGACTACATCCTACTTGTCTGTATCTCTAGGAGGCAGAGTCACCATT
GCTTGCAAGGCAAGTGCCCACATTAAT 90
←······························FR1······························→←--CDR1---

N W L A W Y Q Q K P G N A P R L L I S D A T S L E T G V P S
5'
AATTGGTTAGCCTGGTATCAGCAGAAACCAGGAAATGCTCCTAGGCTCTTAATATCTGATGCA
ACCAGTTTGGAAACTGGGGTTCCTTCA 180
······→←··············FR2··············→←-CDR2-→←···········

R F S G S G S G K D Y T L S I T S L Q T E D V A T Y Y C Q H
5'
AGATTCAGTGGCAGTGGATCTGGAAAGGATTACACTCTCAGCATTACCAGTCTTCAGACTGA
AGATGTTGCTACTTATTACTGTCAACAT 270
···························FR3····························→←····

Y W S T P W T F G G G T K L E I K R A D A A P T V S
5'
TATTGGAGTACTCCGTGGACGTTCGGTGGAGGCACCAAGCTGGAAATCAAACGGGCTGATGC
TGCACCAACTGTATCCACC 351
··········CDR3·····→←··········FR4··········→

Fig. 20

Antibody Heavy Chain

>P2B10G5-VH

L P E V Q L E E S G P G L V K P S Q S L S L T C T V T G Y S

5'

CTTCCGGAGGTCCAGCTGGAGGAGTCTGGACCTGGCCTGGTGAAACCCTCTCAGTCTCTGTCC
CTCACCTGCACTGTCACTGGCTACTCA 90

←················FR1················→ ←

I T S D Y A W N W I R Q F P G N K L E W M G Y I S Y S G S T

5'

ATCACCAGTGATTATGCCTGGAACTGGATCCGGCAGTTTCCAGGAAACAAACTGGAGTGGAT
GGGCTACATAAGCTACAGTGGTAGCACT 180

--CDR1---------→ ←················FR2················→ ←------CDR2------→

N Y N P S L K S R I S I T R D T S K N Q F F L Q L N S V I T

5'

AACTACAACCCATCTCTCAAAAGTCGAATCTCTATCACTCGAGACACCTCCAAGAACCAGTTC
TTCCTGCAGTTGAATTCTGTGATTACT 270

←················FR3················

E D T A T Y Y C A R G G T Y F D Y W G Q G T T L T V S S A K

5'

GAGGACACAGCCACATATTACTGTGCAAGGGGGGGGACTTACTTTGACTACTGGGGCCAAGG
CACCACTCTCACAGTCTCCTCAGCCAAA 360

→ ←------CDR3---------→ ←············FR4············→

T T P P S V Y

5' ACGACACCCCCATCTGTCTATTC 383

Fig. 20 (cont.)

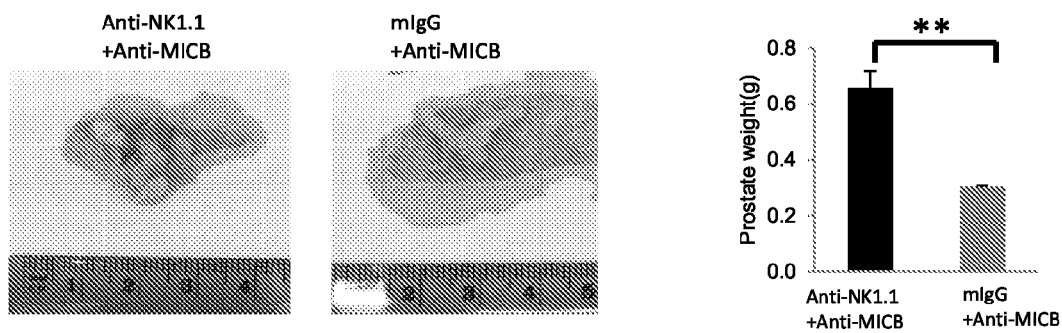
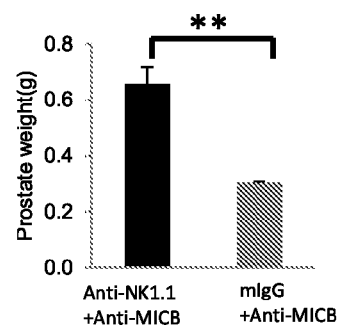
Fig. 23 A  Fig. 23B
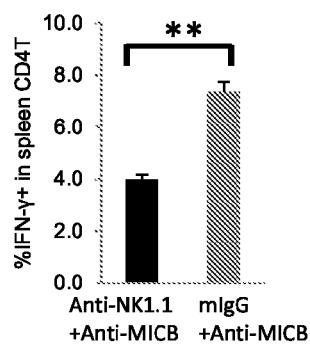
Fig. 23C
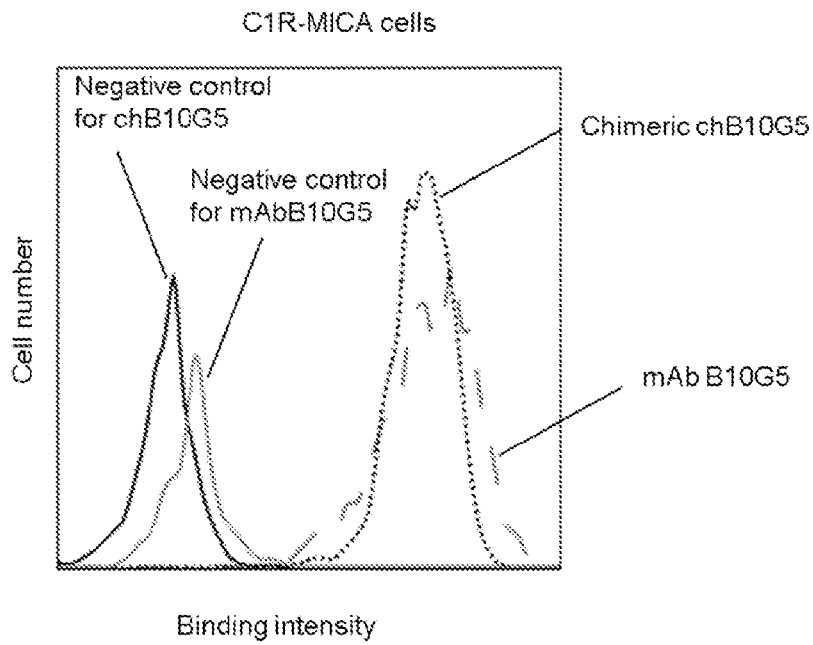
Fig. 24

SOLUBLE MIC NEUTRALIZING MONOCLONAL ANTIBODY FOR TREATING CANCER

CROSS-REFERENCE TO RELATED APPLICATIONS

This application is a 35 U.S.C. §371 National Phase Entry Application of International Application No. PCT/US2014/045366 filed Jul. 3, 2014, which designated the U.S., and which claims benefit under 35 U.S.C. §119(e) of U.S. Provisional Application No. 61/843,182 filed Jul. 5, 2013 and U.S. Provisional Application No. 61/893,734 filed Oct. 21, 2013, the contents of which are incorporated herein by reference in their entirety.

STATEMENT REGARDING FEDERALLY SPONSORED RESEARCH

This invention was made with government support under W81XWH-06-1-0014, awarded by the Department of Defense and R01 CA149405 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 26, 2014, is named 034186-081580-PCT_SL.txt and is 16,528 bytes in size.

BACKGROUND

Elevation in serum soluble NKG2D ligand, soluble sMIC, is associated with metastasis in certain types of cancer. In men diagnosed with prostate cancer, development of metastatic disease is correlated with marked elevation of the serum soluble NKG2D ligand, sMIC, and profound loss of NK cells in the circulation.

SUMMARY

Described herein are the results of investigations as to whether neutralizing serum soluble Major Histocompatibility Complex class I chain-related (sMIC) can be an effective systemic treatment for metastatic cancer. In particular, it was investigated whether an antibody designed or selected to inhibit sMIC (e.g. to neutralize sMIC) shed from MIC+ tumors would be effective to treat those tumors. The studies described herein used a "humanized" double transgenic TRAMP/MIC pre-clinical model and demonstrated that neutralizing serum sMIC with a specific antibody results in regression of advanced metastatic prostate cancer through mechanisms of restoring NK cell homeostasis, priming and polarizing CD4 T cells, and enhanced CD8 T cell function with no systemic cytotoxicity. The present data demonstrate that the sMIC-neutralizing therapy is effective in treating a broad range of MIC cancers. Accordingly, these results are readily generalized to any $MIC^+$ cancer.

BRIEF DESCRIPTION OF THE DRAWINGS

FIG. 1A depicts a Kaplan-Meier plot showing significantly reduced survival of TRAMP/MICB mice in comparison to TRAMP mice (p<0.001). Only tumor-associated incidence of death was considered in the analyses. Numbers indicate animals were surveyed during the indicated survival time. FIG. 1B demonstrates that significant increased prostate weight in cohorts of 24-week-old TRAMP/MICB mice (n=12) in comparison to TRAMP littermates (n=13). FIG. 1C depicts representative images of gross appearance of tumors and associated lymph nodes from TRAMP/MIC(B) mice (representative of 6/12 mice) and TRAMP littermates (representative of 12 out of 13 mice).

FIGS. 2A-2F demonstrate that accelerated progression to PD carcinomas in TRAMP/MIC mice is associated with elevated serum sMIC and loss of surface MIC. FIG. 2A depicts a summary IHC score of surface MICB expression on tumor cells. FIG. 2B depicts quantitative RT-PCR showing comparable levels of MICB expression in PD and WD tumors at the mRNA level. FIG. 2C depicts ELISA measurement of serum levels of sMICB in the cohorts of 24-week TRAMP/MICB mice at various ages during carcinoma development. *, $p<0.01$. **, $p<0.001$. ns, not significant. Note that development of PD carcinomas is associated with marked elevation of serum levels of sMICB. FIG. 2D depicts the correlation of serum sMICB with tumor volume in TRAMP/MICB mice at the age of 24 weeks. FIG. 2E depicts quantitative RT-PCR showing comparable levels of endogenous NKG2D ligand RAE-1 expression in PD and WD tumors at the mRNA level. FIG. 2F depicts a representative micrograph and summary scores of IHC staining demonstrating pattern of endogenous NKG2D ligand RAE-1 expression in TRAMP/MICB carcinomas. Data represent results from four independent analyses.

FIGS. 3A-3E demonstrate that prostate carcinoma progression is associated with sMIC-induced impairment in NK cell peripheral maintenance. FIGS. 3A and 3B Comparisons of splenic CD8 (FIG. 3A) and NK (FIG. 3B) cells and $NKG2D^+$ population in cohorts of 24-week old TRAMP/MICB, TRAMP, and wild-type B6 mice. Left panel, representative dot plots of flow cytometry analyses. Right panel, pooled statistical data of flow cytometry analyses of each cohort. **, $p<0.001$ in comparison to TRAMP mice or to TRAMP/MICB mice that developed WD tumors. FIG. 3C demonstrates the significant inverse correlation of serum sMICB with splenic NK cell population as analyzed from the cohort of 24-week old TRAMP/MICB mice. FIG. 3D depicts representative dot plots of flow cytometry analyses and statistics of pooled data demonstrating systemic (iLN and BM) depletion of NK cells in TRAMP/MICB mice that developed PD carcinoma. iLN, inguinal lymph nodes. BM, bone marrow. FIG. 3E depicts representative dot plots of flow cytometry analyses and statistical data demonstrating significant reduction of NK cells in tumor infiltrated lymphocytes (TILs) in PD tumors from TRAMP/MICB mice. All data show represents results from three independent assays of at least 5 animals.

FIGS. 4A-4D demonstrate that sMIC impairs NK cell peripheral homeostasis and facilitates lung metastasis in experimental TRAMP-C2 lung metastatic model and that neutralizing sMIC with a monoclonal antibody (mAb B10G5) restores NK cell homeostasis and eliminates lung metastasis. FIG. 4A depicts the experiment design. FIG. 4B depicts quantification of lung deposits of micrometastasis demonstrating that sMIC facilitates lung metastasis and that treatment with anti-sMIC (mAb B10G5) inhibits lung metastasis. FIG. 4C depicts representative dot plots (left panel) of flow cytometry analyses and pooled statistical data (right panel) demonstrating NK cell frequency in bone marrow, lymph nodes, and spleens. cIgG, isotype control IgG for the sMIC-neutralizing mAb B10G5. *, $p<0.05$ in comparison to anti-sMIC (mAb B10G5) treatment group and all animals injected with TRAMP-C2 cells. FIG. 4D depicts representative flow cytometry analyses and quantification of splenic BrdU$^+$ NK cell accumulation over 5 days demonstrating NK cell renewal ability. Data are representatives of five animals per subgroup and three independent experiments.

FIGS. 5A and 5B depict the percentage of CD45.1$^+$ NK cells in the total adoptively transferred CD45.1$^+$ population in the spleen (FIG. 5A) and lymph nodes at euthanization (FIG. 5B). FIGS. 5C and 5D depict a summary of V$_{450}$ dilution assay indicating that sMICB perturbs congenic CD45.1$^+$ NK cell proliferation in the spleen (FIG. 5C) and lymph nodes (FIG. 5D) and that treatment with anti-sMIC (mAb B10G5) restores the ability of NK cells to proliferate. 5-8 animals were used in each group. Data represent three independent experiments.

FIGS. 6A-6D demonstrate that expression of membrane-restricted NKG2D ligand MICB.A2 in the TRAMP prostate prevents tumor progression. FIG. 6A depicts a Kaplan-Meier plot demonstrating tumor-free survival of TRAMP/MICB.A2 mice (TRAMP mice with MICB.A2 specifically expressed on the prostate). Numbers indicates animals being surveyed. FIG. 6B depicts the significantly reduced prostate weight in TRAMP/MICB.A2 bi-Tg mice (n=21) in comparison to age-matched TRAMP (n=13) littermates. Age-matched wild-type B6 are shown as normal controls. FIG. 6C demonstrates that no sMICB was detected in the sera of TRAMP/MICB.A2 mice by ELISA. *, sera from TRAMP/MICB mice as the assay positive control. FIG. 6E demonstrates that blocking NKG2D function with an antibody in TRAMP/MICB.A2 mice resulted in significantly elevated prostate weight. Data in FIG. 6D represent two independent experiments.

FIGS. 7A-7D demonstrate that membrane-restricted MICB.A2 sustains NKG2D anti-tumor immunity in both NK and CD8 T cells. FIG. 7A depicts flow cytometry analyses of splenic NK cells from cohorts of 24-week old TRAMP/MICB.A2, TRAMP, and wild type B6 mice and relative levels of NKG2D expression. Left panel, representative dot plots. Right panel, quantification of pooled data. FIGS. 7B and 7C demonstrate that splenic NK cells form TRAMP/MICB.A2 mice and B6 mice have comparable level of IFNγ production (FIG. 7B; left, representative dot plot of flow cytometry analyses; right, statistical summary of data) and lytic ability (FIG. 7C) when stimulated with RMA-RAE-1 cells for 4 h duration. Cytotoxicity assay was performed using the standard $^{51}$Cr release assay. Anti-mouse NKG2D antibody C7 was used as the blocking antibody. FIG. 7D depicts representative dot plots of flow cytometry analyses and statistics of splenic CD8 T cell population and their NKG2D expression. All data represent three independent analyses of a minimum of five animals.

FIGS. 8A-8D demonstrate that development of metastatic prostate cancer in men is associated with reduced NK cell frequency in the blood and high levels of serum sMIC. Data show NK cell (CD3$^-$CD56$^+$) frequency (FIG. 8A), T cell (CD3$^+$CD56$^-$) frequency (FIG. 8B), and serum levels of sMIC (FIG. 8C) from 36 treatment-naïve prostate cancer patients, of whom 25 were diagnosed with localized disease (non-met) and 11 were diagnosed with distant metastasis (Met). Samples from age-matched healthy men (n=10) were used as controls. Data represent results from three independent assays. FIG. 8D demonstrates the significant inverse correlation between serum sMIC and the frequency of circulating NK cells from all patients.

FIG. 9A is a depiction of treatment. FIG. 9B demonstrates representative gross prostate size from antibody treated and control groups. FIG. 9C depicts a summary of prostate weight from antibody treated and control groups. FIG. 9D depicts a summary of metastatic incidence of in antibody treated and control groups.

FIGS. 10A-10C demonstrate that systemic effect of the antibody treatment. FIG. 10A depicts the body weight of animals during the course of treatment. FIG. 10B depicts the serum cytokine profile at the end of the treatment. FIG. 10C depicts serum sMIC as measured by ELISA at the study end point.

FIG. 11A depicts NK cell frequency in the spleen and LN in antibody treated and control groups. FIG. 11B demonstrates NK cell renewal or proliferation in the spleen and LN in antibody treated and control groups. FIG. 11C depicts NK cell IFNγ production in response to PMA and Ionomycin stimulation.

FIG. 12A demonstrates that antibody treated increased NKG2D$^+$CD8 T cells, indication of increased activation. FIG. 12B demonstrates that antibody treatment marked increase CD8 T cell IFNγ production in response to PMA and Ionomycin stimulation.

FIG. 13A depicts a summary of Th1 cell frequency. FIG. 13B depicts a summary of Th17 cell frequency. FIG. 13C depicts a summary of central memory CD4 T cells.

FIG. 14A depicts the prostate-specific transgene constructs. Expression of shedding-sensitive native MICB or shedding-resistant mutant MICB.A2 was under the direction of the prostate-specific rat probasin promoter (−426 to+28 bp). FIG. 14B depicts RT-PCR detection of prostate-specific expression of MICB or MICB.A2. PR, prostate. LV, liver. LU, lung. MU, muscle. SP, spleen. FIG. 14C depicts expression of NKG2D ligands does not significantly influence prostate weight.

FIG. 15A depicts representative flow cytometry analyses (left panel) and quantification (right panel) of pooled data of NK1.1 population (CD3$^-$NK1.1$^+$) of each genotypes. FIG. 15B depicts a representative histogram of NKG2D expression on NK cells. FIG. 15C and FIG.

15D depict representative dot plots of flow cytometry analyses of CD8 T cell population. All data represent at least 6 animals per genotype.

Figure 16A:
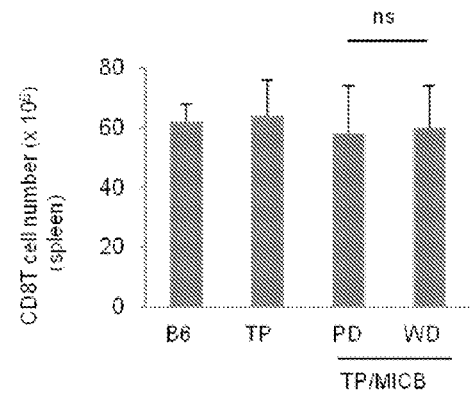
Figure 16B:
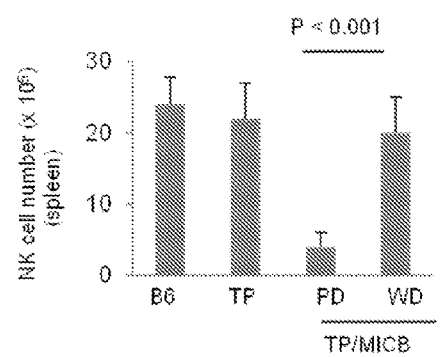
Figure 16C:
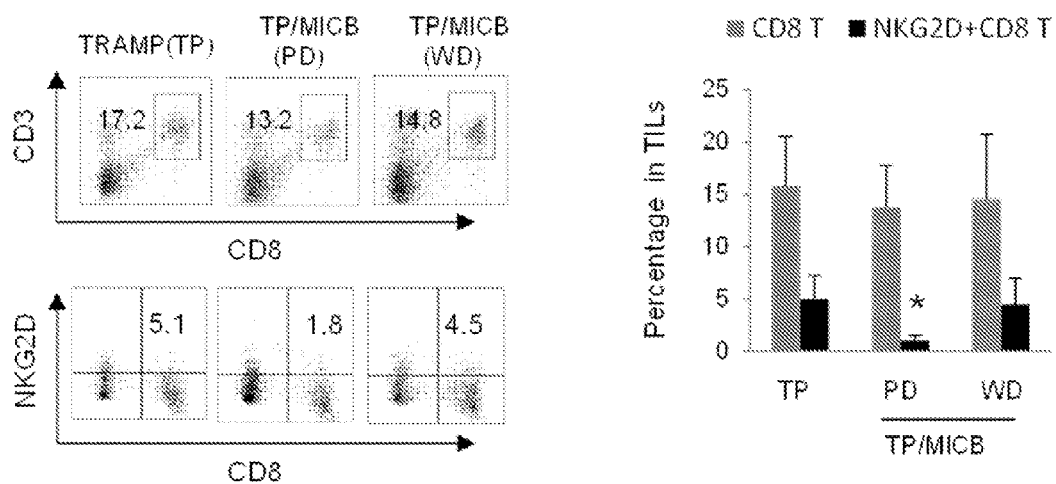

FIGS. 16A-16B depict the absolute number of NK cells (FIG. 16A) and CD8 T cells (FIG. 16B) in the spleens and lymph nodes of TRAMP and TRAMP/MICB mice. Data show significant loss of NK cell number, not CD8 T cell number with progression to PD tumors. FIG. 16C depicts representative dot plots and pooled statistical data showing total CD8 T cells and NKG2D$^+$CD8 T cells infiltrated in tumor parenchyma of TRAMP and TRAMP/MICB mice. Data show no significant difference in total CD8 T infiltrates, but a significant reduction of NKG2D$^+$CD8 T cells. TIL, tumor infiltrated lymphocytes.

Figure 17A:
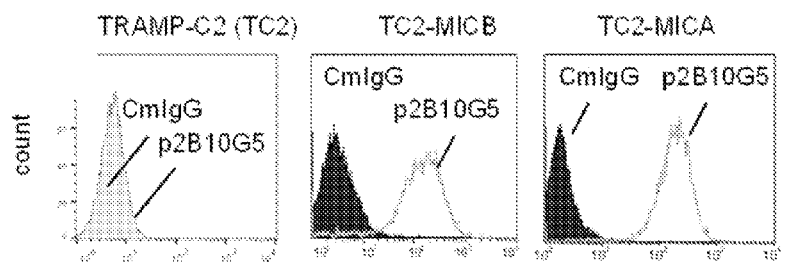
Figure 17B:
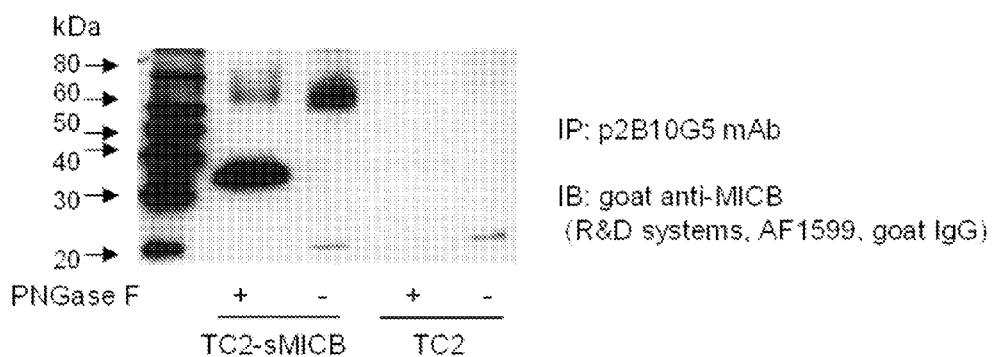
Figure 17C:
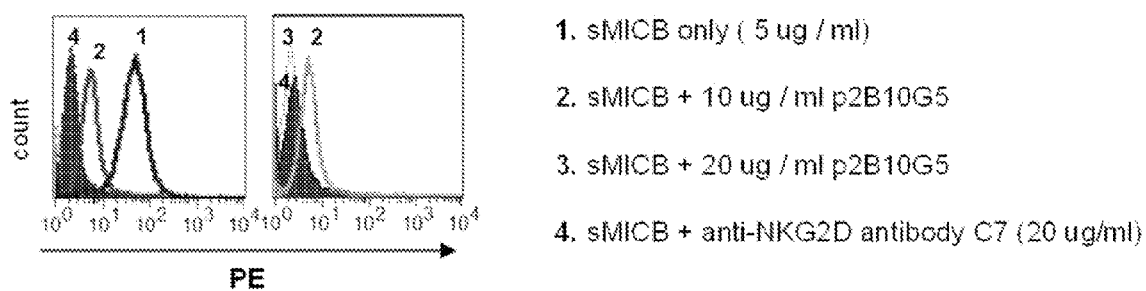

FIGS. 17A-17C demonstrate characterization of sMIC specificity of the antibody p2B10G5. FIG. 17A depicts a representative histogram from flow cytometry analysis showing that purified p2B10G5 mAb is MIC (A and B)-specific. Mouse prostate tumor cell line TRAMP-C2 (TC2) and its derivative TC2-MICA and TRAMP-MICB were incubated with CD16/32 to block FcRγ before incubating with 2 μg/ml of p2B10G5 or control mouse IgG (cIgG) and PE-conjugated goat anti-mouse IgG. FIG. 17B depicts an unedited immunoblot showing p2B10G5 is sMIC-specific. 2 ml Culture supernatant of TC2-sMICB or TC2 cells were incubated with p2B10G5 and protein A-beads. Half of the immune complexes were treated with PNGaseF to deglycosylate. The immune complex were dissolved in SDS-sample buffer, loaded onto 7.5% SDS/PAGE gel, transferred into nitrocellulose membrane, and blotted with goat anti-MICB polyclonal antibody AF1599 (R&D Systems). Lane 1, deglycosylated sMICB. Lane 2, native sMICB. FIG. 17C depicts flow cytometry assay demonstrating that p2B10G5 inhibits sMICB binding to NKG2D on mouse NK cells. Purified mouse splenic NK cells were incubated with biotinylated rsMICB (5 ug/ml) and various concentrations of p2B10G5 followed by PE-streptavidin. Cells were analyzed with BD FACSscan. Data were analyzed with CellQuest software. Data clearly demonstrate that p2B10G5 inhibits the binding of sMICB to mouse NKG2D.

Figure 18:
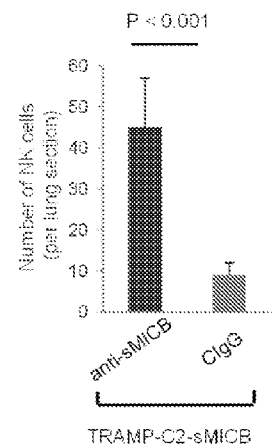

FIG. 18 depicts the loss of NK cells in tissues with tumor metastasis. Bar graph shows the summary data of NK cells counted from one lung section. Five lung sections were counted from each animal to obtain the mean data of an individual. Data show loss of NK cells in lung parenchyma with tumor micrometastases (arrows in H&E staining).

Figure 19A:
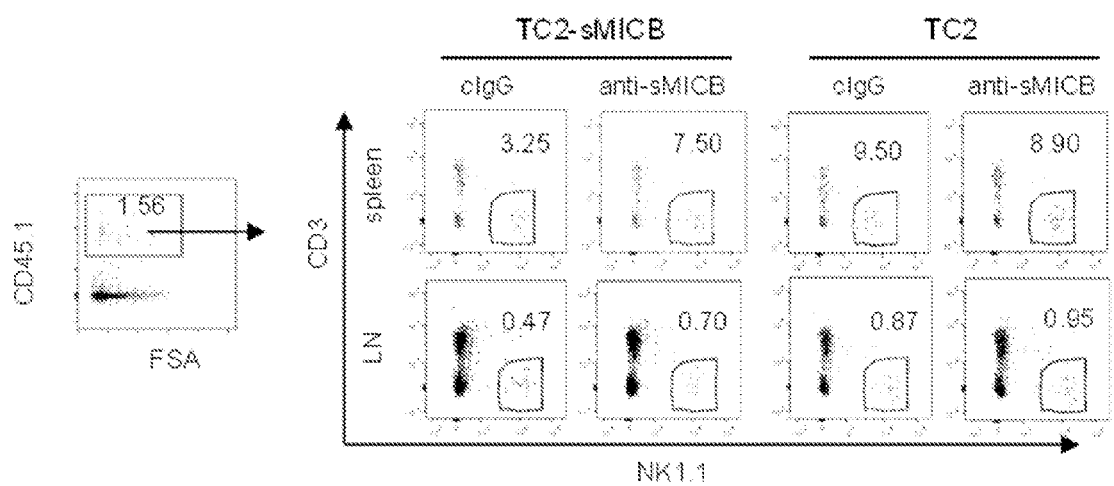
Figure 19B:
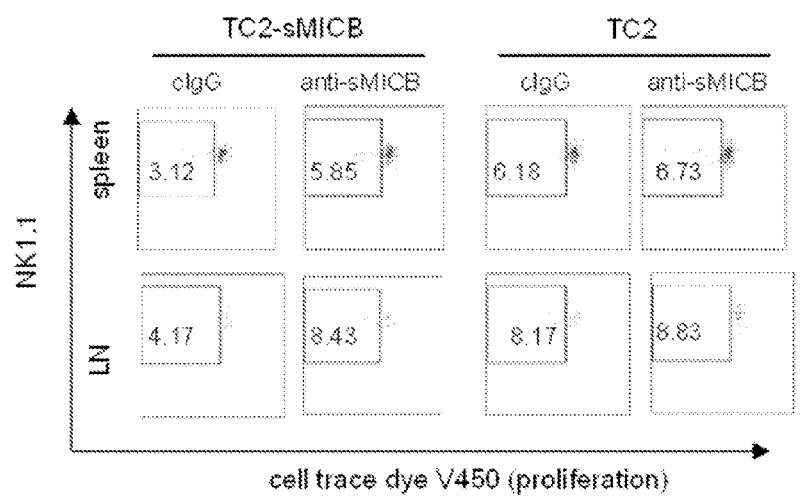
Figure 19C:
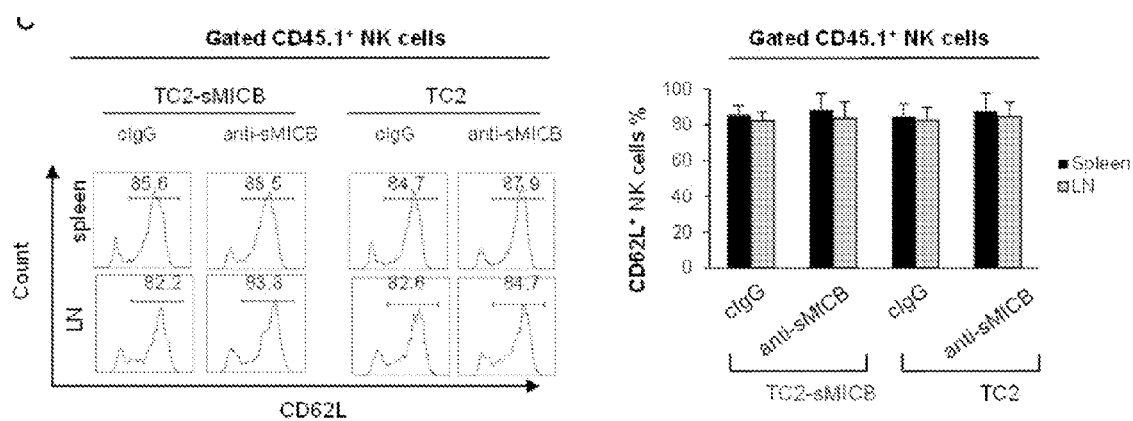

FIGS. 19A-19B depict representative dot plots of flow cytometry analyses of adoptively transferred V450-labeled congenic CD45.1$^+$ NK1.1 population (FIG. 19A) and proliferation (FIG. 19B) in the spleen and lymph nodes of the transplanted TRAMP-C2 (TC2) and TC2-sMICB metastasis model. Data shown that sustained congenic CD45.1$^+$ NK1.1 cells were significant lower in mice implanted with TC2-sMICB cells than those implanted with TC2 cells. Data also show that sMIC neutralizing antibody treatment increases the sustainability of congenic CD45.1$^+$ NK1.1 cells in mice implanted with TC2-sMICB cells by increasing NK cell proliferation. FIG. 19C depicts representative dot plots and pooled statistical data showing that sMICB does not influence the expression of NK cell homing receptor CD62L.

FIG. 20 depicts the sequence of the P2B10G5 antibody (IgG1 K) light chain (protein sequence disclosed as SEQ ID NO: 7 and DNA sequence disclosed as SEQ ID NO: 19) and heavy chain (protein sequence disclosed as SEQ ID NO: 8 and DNA sequence disclosed as SEQ ID NO: 20)

Figure 21A:
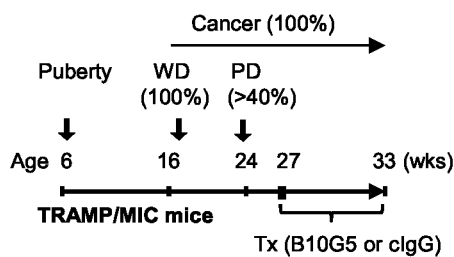
Figure 21B:
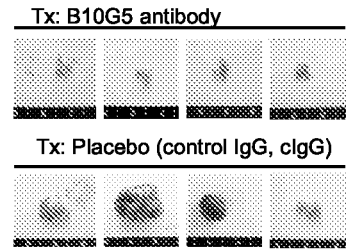
Figure 21C:
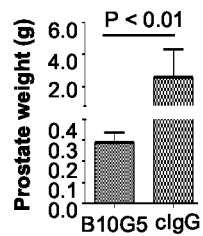
Figure 21D:
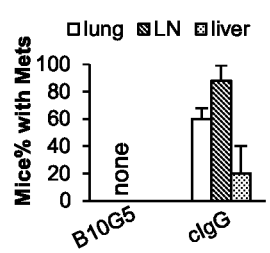
Figure 21E:
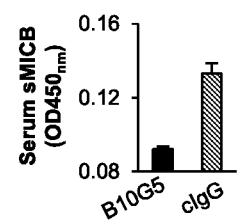
Figure 21F:
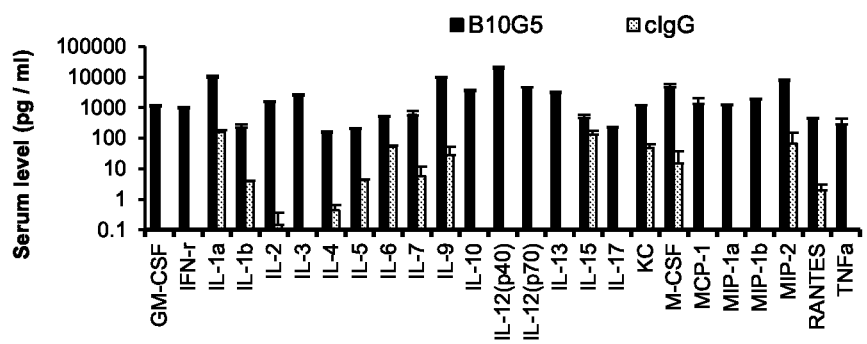
Figure 21G:
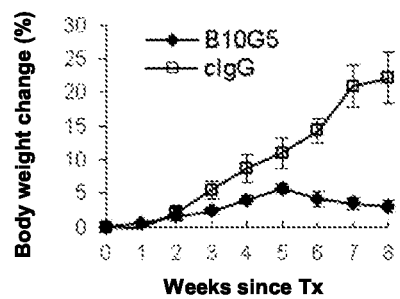

FIGS. 21A-21G demonstrate that therapy with sMIC-specific monoclonal antibody B10G5 resulted in marked inhibition/regression of primary prostate carcinoma and metastasis. FIG. 21A is a schematic of the treatment regimen. FIGS. 21B and 21C depict representative gross prostate size and summary of prostate weight from mice receiving B10G5 therapy or isotype control IgG (cIgG). FIG. 21D depicts a summary of metastatic incidence. FIG. 21E demonstrates that B10G5 therapy reduces serum levels of sMIC. FIG. 21F depicts a graph of serum cytokine profile at the end of the treatment. FIG. 21G depicts a graph of body weight change of mice over therapeutic course. Note that increased body weight in control group is due to large primary tumor burden.

Figure 22:
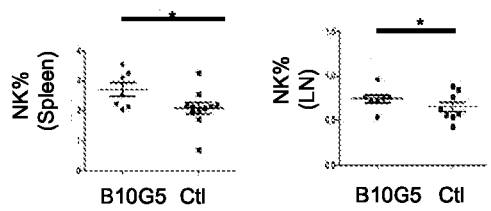
Figure 22:
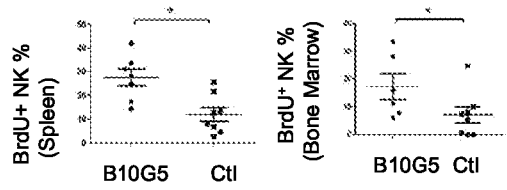
Figure 22:
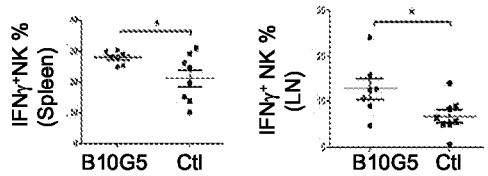
Figure 22:
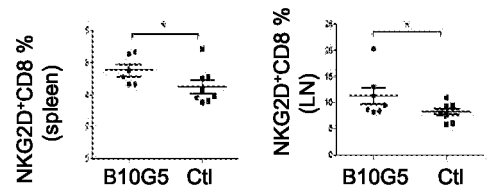
Figure 22:
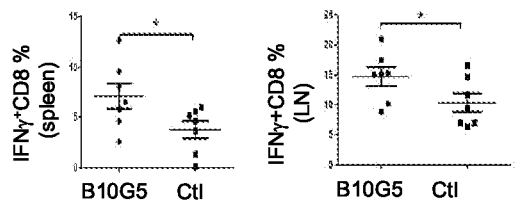
Figure 22:
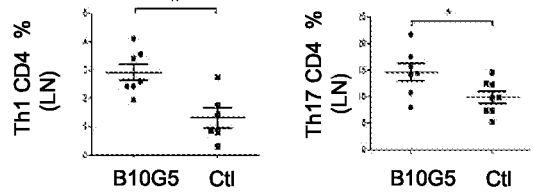
Figure 22:
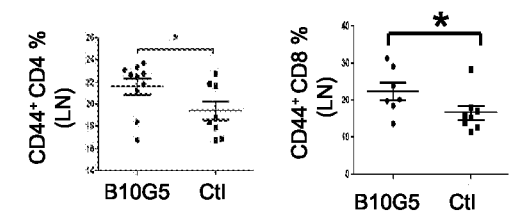

FIGS. 22A-22G demonstrate that B10G5 therapy not only enhances NK cell homeostasis and function but also potentiates adaptive T cell function. FIGS. 22A-22B demonstrate that B10G5 therapy significantly increased the number of NK cells in the periphery and the ability of NK cell to renew. FIG. 22C demonstrates that B10G5 therapy significantly enhanced NK cell IFNγ production in response to PMA and ionomycin restimulation. FIG. 22D demonstrates that B10G5 therapy significantly increase the expression of the co-stimulatory NKG2D on CD8 T cells. FIG. 22E demonstrates that therapy potentiates the CD8 T cell IFNγ production in response to re-stimulation. FIG. 22F demonstrates that B10G5 therapy primed the polarization of CD4 T cells in the dLN to tumor-reactive Th1 and Th17. FIG. 22G demonstrates that B10G5 therapy significantly increased CD44$^{hi}$ memory CD4 and CD8 T cells. Data are representative of three independent studies. n>5 for animals in each group. *, p<0.05.

FIGS. 23A-23C demonstrate that the NK depletion mitigates the therapeutic effect of B10G5. FIG. 23A depicts grossly enlarged prostate tumor upon NK depletion. FIG. 23B depicts a graph comparing prostate weight between NK depleted and non-depleted mice received B10G5 therapy demonstrating that tumors failed to respond to B10G5 therapy with NK cell depletion. FIG. 23C depicts graphs of decreased IFN-γ$^+$ CD4 T cell percentage with NK depletion during B10G5 therapy.

FIG. 24 depicts histograms of flow cytometry analyses demonstrating that chimeric chB10G5 antibody has comparable affinity to native mAb B10G5 in binding to MICA expressed by C1R-MICA cells Chimeric chB10G5 was generated by fusing the variable region $V_L$ and $V_H$ of mAb B10G5 (IgG1) respectively with the human IgG1 constant region of $C_L$ and $C_H$.

DETAILED DESCRIPTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2006).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof as described in Kabat et al. (1971) Ann. NY Acad, Sci. 190:382-391 and/or Kabat, E. A., et al. (1991) Sequences of Proteins of Immunological Interest, Fifth Edition, U.S. Department of Health and Human Services, NIH Publication No. 91-3242.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

"Avidity" is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant (KD of $10^{-5}$ to $10^{-12}$ moles/liter or less, such as $10^{-7}$ to $10^{12}$ moles/liter or less, or $10^{-8}$ to $10^{-12}$ moles/liter (i.e., with an association constant (KA) of $10^5$ to $10^{12}$ liter/moles or more, such as $10^7$ to $10^{12}$ liter/moles or $10^8$ to $10^{12}$ liter/moles). Any KD value greater than $10^{-4}$ mol/liter (or any KA value lower than $10^4$ M$^{-1}$) is generally considered to indicate non-specific binding. The KD for biological interactions which are considered meaningful (e.g., specific) are typically in the range of $10^{-10}$ M (0.1 nM) to $10^{-5}$ M (10000 nM). The stronger an interaction, the lower is its KD. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an anti-MIC-binding peptide (e.g., an antibody or portion thereof) described herein to bind to a target, such as a MIC molecule present on the cell-surface, with a KD $10^{-5}$M (10000 nM) or less, e.g., $10^{-6}$ M, $10^{-7}$M, $10^{-8}$M, $10^{-9}$ M, $10^{-10}$ M, $10^{11}$M, $10^{-12}$M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody or antigen-binding portion thereof is said to specifically bind an antigen when it preferentially recognizes its target antigen in a complex mixture of proteins and/or macromolecules.

In some embodiments, a reagent that binds specifically to sMIC binds specifically to sMIC as compared to non-MIC polypeptides. In some embodiments, a reagent that binds specifically to sMIC binds specifically to sMIC as compared to non-soluble MIC (e.g. as compared to the extracellular domain of uncleaved, mature MIC).

In some embodiments, an antibody or antigen-binding portion thereof as described herein which binds to a sMIC polypeptide with a dissociation constant (KD) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, an isolated antibody or antigen-binding portion thereof described herein binds a sMIC polypeptide with a dissociation constant (KD) of from about $10^{-5}$ M to $10^{-6}$ M. In some embodiments, an isolated antibody or antigen-binding portion thereof described herein binds a sMIC polypeptide with a dissociation constant (KD) of from about $10^{-6}$ M to $10^{-7}$ M. In some embodiments, an isolated antibody or antigen-binding portion thereof described herein binds a sMIC polypeptide with a dissociation constant (KD) of from about $10^{-7}$ M to $10^{-8}$ M. In some embodiments, an isolated antibody or antigen-binding portion thereof described herein binds a sMIC polypeptide with a dissociation constant (KD) of from about $10^{-8}$ M to $10^{-9}$ M. In some embodiments, an isolated antibody or antigen-binding portion thereof described herein binds a sMIC polypeptide with a dissociation constant (KD) of from about $10^{-9}$ M to $10^{-10}$ M. In some embodiments, an isolated antibody or antigen-binding portion thereof described herein binds a sMIC polypeptide with a dissociation constant (KD) of from about $10^{-10}$ M to $10^{-11}$ M. In some embodiments, an isolated antibody or antigen-binding portion thereof described herein binds a sMIC polypeptide with a dissociation constant (KD) of from about $10^{-11}$ M to $10^{-12}$ M. In some embodiments, an isolated antibody or antigen-binding portion thereof described herein binds a sMIC polypeptide with a dissociation constant (KD) of less than $10^{-12}$ M.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

In some embodiments, the technology described herein relates to antibodies and/or polypeptides comprising an antigen-binding portion of an antibody which bind a MIC polypeptide. In some embodiments, the MIC polypeptide is a soluble MIC polypeptide (sMIC). As used herein "soluble MIC" or "sMIC" refers to a portion of a MIC polypeptide that is lacking a transmembrane domain, e.g. an extracellular portion of MIC that has been cleaved from the transmembrane domain. In some embodiments, soluble MIC can comprise about, e.g., amino acids 24-260 of SEQ ID NOs: 15 or 16. In some embodiments, soluble MIC can comprise about, e.g., 20 or more amino acids of residues 24-260 of SEQ ID NO: 15 or 16, e.g., 20, 50, 100, 150 or more amino acids of residues 24-260 of SEQ ID NO: 15 or 16.

Major Histocompatibility Complex class I chain-related (MIC) polypeptides are surface transmembrane proteins. The presence of a MIC polypeptide on the cell surface can signal the immune receptor NKG2D for tumor immune destruction, typically by natural killer cells (NK cells) and cytotoxic T cells (CTLs). However, in many tumors, MIC is shed from the tumor surface, resulting in decreased host immunity against the tumor cell and promoting tumor evasion and progression. MIC polypeptides include, but are not limited to the human MICA (e.g. NCBI Ref Seqs NP_000238 (SEQ ID NO:15) and 001170990) and human MICB (e.g. NCBI Ref Seq: NP_005922 (SEQ ID NO: 16). In some embodiments, a MIC polypeptide can comprise MICA. In some embodiments, a MIC polypeptide can comprise MICB.

In some embodiments, the methods and compositions described herein relate to inhibition of sMIC, e.g. reducing the level and/or activity of sMIC that is available to interact with cellular receptors. In some embodiments, inhibition of sMIC can be a reduction of unbound sMIC (e.g. sMIC not bound to a receptor and/or available to be bound by the antibody reagents described herein). In some embodiments, inhibition of sMIC can be a reduction of the level of sMIC, e.g. the level of sMIC in circulation.

In some embodiments, described herein is an isolated antibody or antigen-binding portion thereof that specifically binds a sMIC polypeptide, said antibody or antigen-binding portion thereof comprising one or more heavy and light chain complementarity determining regions (CDRs) selected from the group consisting of: (a) a light chain CDR1 having the amino acid sequence of SEQ ID NO: 9; (b) a light chain CDR2 having the amino acid sequence of SEQ ID NO: 10; (c) a light chain CDR3 having the amino acid sequence of SEQ ID NO: 11; (d) a heavy chain CDR1 having the amino acid sequence of SEQ ID NO: 12; (e) a heavy chain CDR2 having the amino acid sequence of SEQ ID NO: 13; and (f) a heavy chain CDR3 having the amino acid sequence of SEQ ID NO: 14. In some embodiments, described herein is an isolated antibody or antigen-binding portion thereof that specifically binds a sMIC polypeptide, said antibody or antigen-binding portion thereof comprising the light chain complementarity determining regions (CDRs): (a) a light chain CDR1 having the amino acid sequence of SEQ ID NO: 9; (b) a light chain CDR2 having the amino acid sequence of SEQ ID NO: 10; and (c) a light chain CDR3 having the amino acid sequence of SEQ ID NO: 11. In some embodiments, described herein is an isolated antibody or antigen-binding portion thereof that specifically binds a sMIC polypeptide, said antibody or antigen-binding portion thereof comprising the heavy chain complementarity determining regions (CDRs): (d) a heavy chain CDR1 having the amino acid sequence of SEQ ID NO: 12; (e) a heavy chain CDR2 having the amino acid sequence of SEQ ID NO: 13; and (f) a heavy chain CDR3 having the amino acid sequence of SEQ ID NO: 14. In some embodiments, described herein is an isolated antibody or antigen-binding portion thereof that specifically binds a sMIC polypeptide, said antibody or antigen-binding portion thereof comprising the heavy and light chain complementarity determining regions (CDRs): (a) a light chain CDR1 having the amino acid sequence of SEQ ID NO: 9; (b) a light chain CDR2 having the amino acid sequence of SEQ ID NO: 10; (c) a light chain CDR3 having the amino acid sequence of SEQ ID NO: 11; (d) a heavy chain CDR1 having the amino acid sequence of SEQ ID NO: 12; (e) a heavy chain CDR2 having the amino acid sequence of SEQ ID NO: 13; and (f) a heavy chain CDR3 having the amino acid sequence of SEQ ID NO: 14.

In some embodiments, the antibody or polypeptide comprising an antigen-binding fragment of an antibody described herein comprises one or more CDRs, e.g. 1 CDR, 2 CDRs, 3 CDRs, 4 CDRs, 5 CDRs, or 6 CDRs, selected from the group consisting of (a) a light chain CDR1 having the amino acid sequence of SEQ ID NO: 9; (b) a light chain CDR2 having the amino acid sequence of SEQ ID NO: 10; (c) a light chain CDR3 having the amino acid sequence of SEQ ID NO: 11; (d) a heavy chain CDR1 having the amino acid sequence of SEQ ID NO: 12; (e) a heavy chain CDR2 having the amino acid sequence of SEQ ID NO: 13; and (f) a heavy chain CDR3 having the amino acid sequence of SEQ ID NO: 14. In some embodiments, the antibody or polypeptide comprising an antigen-binding fragment of an antibody described herein comprises a heavy chain or a portion thereof, comprising one or more CDRs, e.g., 1 CDR, 2 CDRs, or 3 CDRs selected from the group consisting of a heavy chain CDR1 having the amino acid sequence of SEQ ID NO: 12; a heavy chain CDR2 having the amino acid sequence of SEQ ID NO: 13; and a heavy chain CDR3 having the amino acid sequence of SEQ ID NO: 14. In some embodiments, the antibody or polypeptide comprising an antigen-binding fragment of an antibody described herein comprises a light chain or a portion thereof, comprising one or more CDRs, e.g., 1 CDR, 2 CDRs, or 3 CDRs selected from the group consisting of a light chain CDR1 having the amino acid sequence of SEQ ID NO:9; a light chain CDR2 having the amino acid sequence of SEQ ID NO: 10; a light chain CDR3 having the amino acid sequence of SEQ ID NO: 11.

In some embodiments, the isolated antibody or antigen-binding portion thereof can comprise a heavy chain comprising the amino acid sequence of SEQ ID NO: 8. In some embodiments, the isolated antibody or antigen-binding portion thereof can comprise a light chain comprising the amino acid sequence of SEQ ID NO: 7.

In embodiments wherein an antibody as described herein comprises at least one CDR which is not identical to the sequence of SEQ ID NOs: 9-14, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding fragment thereof as described herein, will result in an antigen or antigen-binding fragment thereof which will bind a MIC polypeptide. In some embodiments, the antibody or antigen-binding fragment thereof can inhibit sMIC. The method described in Fujii et al. also permits one of ordinary skill in the art to screen for a light chain sequence which will give the desired binding behavior when combined with a known heavy chain fragment and vice versa.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al, Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan (FASEB J. 9:133-139 (1995)) and MacCallum (J Mol Biol 262(5):732-45 (1996)) and Chothia (J. Mol. Biol. 196:901-917 (1987) and Nature 342:877-883 (1989)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

As used herein, the terms "proteins" and "polypeptides" are used interchangeably herein to designate a series of amino acid residues each connected to the other by peptide bonds between the alpha-amino and carboxy groups of adjacent residues. The terms "protein", and "polypeptide", which are used interchangeably herein, refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to an encoded gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "antigen-binding fragment" or "antigen-binding portion" of an antibody, used interchangeably herein, refer to one or more fragments of an antibody as described herein, said fragments) still having the binding affinities as defined above herein. Fragments of a complete antibody have been shown to be able to carry out the antigen-binding function of an antibody. In accordance with the term "antigen-binding portion" of an antibody, examples of binding fragments include (i) an Fab fragment, i.e. a monovalent fragment composed of the VL, VH, CL and CH1 domains; (ii) an F(ab')2 fragment, i.e. a bivalent fragment comprising two Fab fragments linked to one another in the hinge region via a disulfide bridge; (iii) an Fd fragment composed of the VH and CH1 domains; (iv) an Fv fragment composed of the FL and VH domains of a single arm of an antibody; and (v) a dAb fragment (Ward et al., (1989) Nature 341:544-546) consisting of a VH domain or of VH, CH1, CH2, DH3, or VH, CH2, CH3 (dAbs, or single domain antibodies, comprising only $V_L$ domains have also been shown to specifically bind to target eptiopes). Although the two domains of the Fv fragment, namely VL and VH, are encoded by separate genes, they may further be linked to one another using a synthetic linker, e.g. a poly-G4S amino acid sequence ('G4S' disclosed as SEQ ID NO: 17), and recombinant methods, making it possible to prepare them as a single protein chain in which the VL and VH regions combine in order to form monovalent molecules (known as single chain Fv (ScFv); see, for example, Bird et al. (1988) Science 242:423-426; and Huston et al. (1988) Proc. Natl. Acad. Sci. USA 85:5879-5883). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites (see, for example, Holliger, R, et al. (1993) Proc. Natl. Acad. Sci. USA 90:64446448; Poljak, R. J, et al. (1994) Structure 2:1121-1123). An immunoglobulin constant domain refers to a heavy or light chain constant domain. Human IgG heavy chain and light chain constant domain amino acid sequences are known in the art.

Furthermore, an antibody as described herein or an antigen-binding portion thereof may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule (Kipriyanov, S. M., et al. (1995) Human Antibodies and Hybridomas 6:93-101) and the use of a cystein residue, a marker peptide and a C-terminal polyhistidinyl, e.g. hexahistidinyl tag ('hexahistidinyl tag' disclosed as SEQ ID NO: 18) in order to produce bivalent and biotinylated scFv molecules (Kipriyanov, S. M., et al. (1994) Mol. Immunol. 31:10471058).

In some embodiments, the antibody and/or antigen-binding portion thereof described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding fragment thereof.

As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g. an epitope present on sMIC) of a MIC polypeptide). Such conservatively modified variants are in addition to and do not exclude polymorphic variants, interspecies homologs, and alleles consistent with the disclosure.

In some embodiments, a conservatively modified variant of an antibody reagent can comprise alterations other than in the CDRs, e.g. a conservatively modified variant of an antibody reagent can comprise CDRs having the sequence of one or more of SEQ ID NOs 9-14.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particular conservative substitutions include, for example; Ala into Gly or into Ser; Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the antibody and/or antigen-binding portion thereof described herein can be a variant of a sequence described herein, e.g. a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity, e.g. antigen-specific binding activity for the relevant target polypeptide, e.g. a sMIC polypeptide. A wide variety of PCR-based site-specific mutagenesis approaches are also known in the art and can be applied by the ordinarily skilled artisan.

Examples of substitution variants include conservative substitution of amino acids, e.g. in a $V_H$ or $V_L$, domain, that do not alter the sequence of a CDR. A conservative substitution in a sequence not comprised by a CDR can be a substitution relative to a wild-type or naturally-occurring sequence, e g human or murine framework and/or constant regions of an antibody sequence.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, Jan. 1985, 12-19); Smith et al. (Genetic Engineering: Principles and Methods, Plenum Press, 1981); and U.S. Pat. Nos. 4,518,584 and 4,737,462, which are herein incorporated by reference in their entireties.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the antibody or antigen-binding portion thereof is a fully human antibody. In some embodiments, the antibody or antigen-binding portion thereof is a humanized antibody. In some embodiments, the antibody or antigen-binding portion thereof is a chimeric antibody. In some embodiments, the antibody or antigen-binding portion thereof is a recombinant polypeptide.

The term "human antibody" refers to antibodies whose variable and constant regions correspond to or are derived from immunoglobulin sequences of the human germ line, as described, for example, by Kabat et al. (see Kabat, et al. (1991) Sequences of Proteins of Immunological Interest, Fifth Edition, U.S. Department of Health and Human Services, NIH Publication No. 91-3242). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line (see Kabat, E. A., et al. (1991) Sequences of Proteins of Immunological Interest, Fifth Edition, U.S. Department of Health and Human Services, NIH Publication No. 91-3242). According to particular embodiments, however, such recombinant human antibodies are subjected to in-vitro mutagenesis (or to a somatic in-vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g. a mouse-antibody, (referred to as the donor immunoglobulin). See, Queen et al., Proc Natl Acad Sci USA 86:10029-10033 (1989) and WO 90/07861, U.S. Pat. Nos. 5,693,762, 5,693,761, 5,585,089, 5,530,101 and Winter, U.S. Pat. No. 5,225,539, which are herein incorporated by reference in their entirety. The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies. See Carter et al., WO 92/22653, which is herein incorporated by reference in its entirety.

In some embodiments, the antibody reagents (e.g. antibodies) described herein are not naturally-occurring biomolecules. For example, a murine antibody raised against an antigen of human origin would not occur in nature absent human intervention and manipulation, e g manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, N Y, 1982 and 1989), and Ausubel, 1987, 1993, and can be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

Accordingly, the expression of an antibody or antigen-binding portion thereof as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989). Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art. See Ausubel et al., 1987, 1993.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in E. coli., for example. Other gene expression elements useful for the expression of cDNA encoding antibodies or antigen-binding portions thereof include, but are not limited to (a) viral transcription promoters and their enhancer elements, such as the SV40 early promoter. (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983) Immunoglobulin cDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an antibody, antigen-binding portion thereof, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the fused genes encoding the antibody, antigen-binding fragment thereof, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the fused genes encoding chimeric H and L chains can be assembled on the same expression vector.

For transfection of the expression vectors and production of the chimeric, humanized, or composite human antibodies described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, or antigen-binding portion thereof as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 Science 1538 (1988), as known to one of ordinary skill in the art.

Yeast provides certain advantages over bacteria for the production of immunoglobulin H and L chains. Yeasts carry out post-translational peptide modifications including glycosylation. A number of recombinant DNA strategies exist that utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conf. Yeast, Genetics & Molec. Biol. (Montpelier, France, 1982).

Yeast gene expression systems can be routinely evaluated for the levels of production, secretion and the stability of antibodies, and assembled chimeric, humanized, or composite human antibodies, portions and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45, (Glover, ed., IRL Press, 1985) and e.g., U.S. Publication No. US 2006/0270045 A1.

Bacterial strains can also be utilized as hosts for the production of the antibody molecules or peptides described herein, E. coli K12 strains such as E. coli W3110 (ATCC 27325), Bacillus species, enterobacteria such as Salmonella typhimurium or Serratia marcescens, and various Pseudomonas species can be used. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of chimeric, humanized, or composite humanized antibodies and fragments thereof encoded by the cloned immunoglobulin cDNAs or CDRs in bacteria (see Glover, 1985; Ausubel, 1987, 1993; Sambrook, 1989; Colligan, 1992-1996).

Host mammalian cells can be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells. Exemplary eukaryotic cells that can be used to express polypeptides include, but are not limited to, COS cells, including COS 7 cells; 293 cells, including 293-6E cells; CHO cells, including CHO—S and DG44 cells; PER.C6™ cells (Crucell); and NSO cells. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, one or more antibodies or antigen-binding portions thereof as described herein can be produced in vivo in an animal that has been engineered or transfected with one or more nucleic acid molecules encoding the polypeptides, according to any suitable method.

In some embodiments, an antibody or antigen-binding portion thereof as described herein is produced in a cell-free system. Nonlimiting exemplary cell-free systems are described, e.g., in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

Many vector systems are available for the expression of cloned H and L chain genes in mammalian cells (see Glover, 1985). Different approaches can be followed to obtain complete $H_2L_2$ antibodies. As discussed above, it is possible to co-express H and L chains in the same cells to achieve intracellular association and linkage of H and L chains into complete tetrameric $H_2L_2$ antibodies or antigen-binding portions thereof. The co-expression can occur by using either the same or different plasmids in the same host. Genes for both H and L chains or portions thereof can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing antibodies, antigen-binding portions thereof and/or $H_2L_2$ molecules via either route could be transfected with plasmids encoding additional copies of peptides, H, L, or H plus L chains in conjunction with additional selectable markers to generate cell lines with enhanced properties, such as higher production of assembled $H_2L_2$ antibody molecules or enhanced stability of the transfected cell lines.

Additionally, plants have emerged as a convenient, safe and economical alternative main-stream expression systems for recombinant antibody production, which are based on large scale culture of microbes or animal cells. Antibodies can be expressed in plant cell culture, or plants grown conventionally. The expression in plants may be systemic, limited to susb-cellular plastids, or limited to seeds (endosperms). See, e.g., U.S. Patent Pub. No. 2003/0167531; U.S. Pat. Nos. 6,080,560; 6,512,162; WO 0129242. Several plant-derived antibodies have reached advanced stages of development, including clinical trials (see, e.g., Biolex, NC).

In some aspects, provided herein are methods and systems for the production of a humanized antibody, which is prepared by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors can be the same vector. Also provided herein are DNA sequences encoding the light chain or the heavy chain of the humanized antibody; an expression vector which incorporates a said DNA sequence; and a host transformed with a said expression vector.

Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

In addition, techniques developed for the production of "chimeric antibodies" (see Morrison et al., Proc. Natl. Acad. Sci. 81:851-855 (1984); Neuberger et al., Nature 312:604-608 (1984); Takeda et al., Nature 314:452-454 (1985); which are incorporated by reference herein in their entireties) by splicing genes from a mouse, or other species, antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells (WO 87/02671; which is incorporated by reference herein in its entirety). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Alternatively, techniques described for the production of single chain antibodies (see, e.g. U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989); which are incorporated by reference herein in their entireties) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (see, e.g. Skerra et al., Science 242:1038-1041 (1988); which is incorporated by reference herein in its entirety).

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies. These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences. *E. coli* is one prokaryotic host particularly useful for cloning the DNA sequences. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization. Mammalian cells are a preferred host for expressing nucleotide segments encoding immunoglobulins or fragments thereof. See Winnacker, From Genes to Clones, (VCH Publishers, N Y, 1987), which is incorporated herein by reference in its entirety. A number of suitable host cell lines capable of secreting intact heterologous proteins have been developed in the art, and include CHO cell lines, various COS cell lines, HeLa cells, L cells and multiple myeloma cell lines. Expression vectors for these cells can include expression control sequences, such as an origin of replication, a promoter, an enhancer (Queen et al., "Cell-type Specific Regulation of a Kappa Immunoglobulin Gene by Promoter and Enhancer Elements," Immunol Rev 89:49 (1986), incorporated herein by reference in its entirety), and necessary processing information sites, such as ribosome binding sites, RNA splice sites, polyadenylation sites, and transcriptional terminator sequences. Preferred expression control sequences are promoters substantially similar to a region of the endogenous genes, cytomegalovirus, SV40, adenovirus, bovine papillomavirus, and the like. See Co et al., "Chimeric and Humanized Antibodies with Specificity for the CD33 Antigen," J Immunol 148:1149 (1992), which is incorporated herein by reference in its entirety. Alternatively, antibody coding sequences can be incorporated in transgenes for introduction into the genome of a transgenic animal and subsequent expression in the milk of the transgenic animal (e.g., according to methods described in U.S. Pat. Nos. 5,741,957, 5,304,489, 5,849,992, all incorporated by reference herein in their entireties). Suitable transgenes include coding sequences for light and/or heavy chains in operable linkage with a promoter and enhancer from a mammary gland specific gene, such as casein or beta lactoglobulin. The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra, which is herein incorporated by reference in is entirety). For production of transgenic animals, transgenes can be microinjected into fertilized oocytes, or can be incorporated into the genome of embryonic stem cells, and the nuclei of such cells transferred into enucleated oocytes. Once expressed, antibodies can be purified according to standard procedures of the art, including HPLC purification, column chromatography, gel electrophoresis and the like (see generally, Scopes, Protein Purification (Springer-Verlag, NY, 1982), which is incorporated herein by reference in its entirety).

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROTEIN PURIF. (Springer-Verlag, N Y, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized or composite human antibody can then be used therapeutically or in developing and performing assay procedures, immunofluorescent stainings, and the like. See generally, Vols. I & II Immunol Meth. (Lefkovits & Pernis, eds., Acad. Press, N Y, 1979 and 1981).

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antigen-binding portion thereof as described herein. Such functional activities include inhibition of sMIC, and/or anti-cancer activity. Additionally, a polypeptide having functional activity means the polypeptide exhibits activity similar, but not necessarily identical to, an activity of a reference antibody or antigen-binding portion thereof as described herein, including mature forms, as measured in a particular assay, such as, for example, a biological assay, with or without dose dependency. In the case where dose dependency does exist, it need not be identical to that of the reference antibody or antigen-binding portion thereof, but rather substantially similar to the dose-dependence in a given activity as compared to the reference antibody or antigen-binding portion thereof as described herein (i.e., the candidate polypeptide will exhibit greater activity, or not more than about 25-fold less, about 10-fold less, or about 3-fold less activity relative to the antibodies and antigen-binding fragments described herein).

In some embodiments, the technology described herein relates to a nucleic acid encoding an antibody or antigen-binding portion thereof as described herein. As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

In some embodiments, a nucleic acid encoding an antibody or antigen-binding portion thereof as described herein is comprised by a vector. In some of the aspects described herein, a nucleic acid sequence encoding an antibody or antigen-binding portion thereof as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

Aspects of the technology described herein relate to compositions comprising an antibody or antigen-binding portion thereof as described herein or a nucleic acid encoding an antibody or antigen-binding portion thereof as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody or antigen-binding portion thereof as described herein or a nucleic acid encoding an antibody or antigen-binding portion thereof as described herein can be a lyophilisate.

In some embodiments, the technology described herein relates to a syringe comprising a therapeutically effective amount of a composition described herein.

As used herein, the phrase "therapeutically effective amount", "effective amount" or "effective dose" refers to an amount that provides a therapeutic or aesthetic benefit in the treatment, prevention, or management of a tumor or malignancy, e.g. an amount that provides a statistically significant decrease in at least one symptom, sign, or marker of a tumor or malignancy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering an antibody or antigen-binding portion thereof as described herein or a nucleic acid encoding an antibody or antigen-binding portion thereof as described herein to a subject. In some embodiments, the subject is in need of treatment for a cancer and/or malignancy. In some embodiments, the subject is in need of treatment for an epithelial cell tumor or a hematopoietic malignancy. In some embodiments, the method is a method of treating a subject. In some embodiments, the method is a method of treating an epithelial cell tumor or a hematopoietic malignancy in a subject.

A "tumor" as used herein refers to an uncontrolled growth of cells which interferes with the normal functioning of the bodily organs and systems. The terms "cancer" and "malignancy" refer to a tumor that is metastatic, i.e. that is it has become invasive, seeding tumor growth in tissues remote from the original tumor site. A subject that has a cancer or a tumor is a subject having objectively measurable cancer cells present in the subject's body. Included in this definition are benign tumors and malignant cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the tumor or malignancy is MIC-positive. As used herein, the term "MIC-positive tumor" is used to describe a tumor cell, a cluster of tumor cells or a tumor mass, which produces a MIC protein. This term is intended to encompass all tumor cells and/or tumor masses that shed all or part of a MIC protein, thus these cells may only display a MIC protein on its surface for a short time period—that is, the term encompasses tumors that shed MIC protein, regardless of whether detectable MIC protein remains present on their cell surface or not. However, any tumor that is capable of escaping innate immune rejection by shedding MIC is considered to be a "MIC-positive tumor" as that term is used herein. Some non-limiting examples of MIC-positive tumors include epithelial cell tumors and hematopoietic malignancies. In some embodiments, the MIC-positive tumor or malignancy can be a MIC-positive prostate cancer and/or metastasis thereof.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, various cancers. In addition, the methods described herein can be used to treat domesticated animals and/or pets. A subject can be male or female.

A subject can be one who has been previously diagnosed with or identified as suffering from or having a condition in need of treatment (e.g. a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment. As used herein, the term "administering," refers to the placement of an antibody or antigen-binding portion thereof as described herein or a nucleic acid encoding an antibody or antigen-binding portion thereof as described herein into a subject by a method or route which results in at least partial localization of the agents at a desired site. The pharmaceutical composition comprising an antibody or antigen-binding portion thereof as described herein or a nucleic acid encoding an antibody or antigen-binding portion thereof as described herein disclosed herein can be administered by any appropriate route which results in an effective treatment in the subject.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 µg/kg body weight to 100 µg/kg body weight. Alternatively, the dose range can be titrated to maintain serum levels between 1 µg/mL and 1000 µg/mL. For systemic administration, subjects can be administered a therapeutic amount, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In fact, to the extent that inhibition of MIC shedding can promote immune attack on a tumor, long term administration is contemplated, e.g. first to treat the tumor itself, and then to provide continued surveillance against the development of tumor cells that gain the ability to shed MIC. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m$^2$ to about 700 mg/m$^2$. In some embodiments, the dose can be about 250 mg/m$^2$. In some embodiments, the dose can be about 375 mg/m$^2$. In some embodiments, the dose can be about 400 mg/m$^2$. In some embodiments, the dose can be about 500 mg/m$^2$.

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments the dose can be administered about every 2 weeks. In some embodiments the dose can be administered about every 3 weeks. In some embodiments, the dose can be from about 2 mg/kg to about 15 mg/kg administered about every 2 weeks. In some embodiments, the dose can be from about 2 mg/kg to about 15 mg/kg administered about every 3 weeks. In some embodiments, the dose can be from about 2 mg/kg to about 15 mg/kg administered intravenously about every 2 weeks. In some embodiments, the dose can be from about 2 mg/kg to about 15 mg/kg administered intravenously about every 3 weeks. In some embodiments, the dose can be from about 200 mg/m$^2$ to about 400 mg/m$^2$ administered intravenously about every week. In some embodiments, the dose can be from about 200 mg/m$^2$ to about 400 mg/m$^2$ administered intravenously about every 2 weeks. In some embodiments, the dose can be from about 200 mg/m$^2$ to about 400 mg/m$^2$ administered intravenously about every 3 weeks. In some embodiments, a total of from about 2 to about 10 doses are administered. In some embodiments, a total of 4 doses are administered. In some embodiments, a total of 5 doses are administered. In some embodiments, a total of 6 doses are administered. In some embodiments, a total of 7 doses are administered. In some embodiments, a total of 8 doses are administered. In some embodiments, the administration occurs for a total of from about 4 weeks to about 12 weeks. In some embodiments, the administration occurs for a total of about 6 weeks. In some embodiments, the administration occurs for a total of about 8 weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, gemcitabine, cisplastin, paclitaxel, carboplatin, bortezomib, AMG479, vorinostat, rituximab, temozolomide, rapamycin, ABT-737, and PI-103.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ Edition, 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g. interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Patent Publication WO 2003/063792 and U.S. Pat. No. 8,329,660. In some embodiments, the immunotherapy stimulates NK responses. In some embodiments, the immunotherapy is an adoptive cell transfer approach.

The efficacy of a given treatment for cancer can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc. In addition, efficacy of an agent can be measured by a decrease in circulating MIC peptides or fragments thereof in a subject being treated with an agent comprising an antibody or antigen-binding portion thereof as described herein or a nucleic acid encoding an antibody or antigen-binding portion thereof as described herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

1. An isolated antibody or antigen-binding portion thereof that specifically binds to a sMIC polypeptide, the antibody or antigen-binding portion thereof comprising one or more heavy and light chain complementarity determining regions (CDRs) selected from the group consisting of:
    a. a light chain CDR1 having the amino acid sequence of SEQ ID NO: 9;
    b. a light chain CDR2 having the amino acid sequence of SEQ ID NO: 10;
    c. a light chain CDR3 having the amino acid sequence of SEQ ID NO: 11;
    d. a heavy chain CDR1 having the amino acid sequence of SEQ ID NO: 12;
    e. a heavy chain CDR2 having the amino acid sequence of SEQ ID NO: 13; and
    f. a heavy chain CDR3 having the amino acid sequence of SEQ ID NO: 14.
2. The isolated antibody or antigen-binding portion thereof of paragraph 1, comprising the light chain complementarity determining regions (CDRs):
    a. a light chain CDR1 having the amino acid sequence of SEQ ID NO: 9;
    b. a light chain CDR2 having the amino acid sequence of SEQ ID NO: 10; and
    c. a light chain CDR3 having the amino acid sequence of SEQ ID NO: 11.
3. The isolated antibody or antigen-binding portion thereof of any of paragraphs 1-2, comprising the heavy chain complementarity determining regions (CDRs):
    a. a heavy chain CDR1 having the amino acid sequence of SEQ ID NO: 12;
    b. a heavy chain CDR2 having the amino acid sequence of SEQ ID NO: 13; and
    c. a heavy chain CDR3 having the amino acid sequence of SEQ ID NO: 14.
4. The isolated antibody or antigen-binding portion thereof of any of paragraphs 1-2, comprising the complementarity determining regions (CDRs):
    a. a light chain CDR1 having the amino acid sequence of SEQ ID NO: 9;
    b. a light chain CDR2 having the amino acid sequence of SEQ ID NO: 10;
    c. a light chain CDR3 having the amino acid sequence of SEQ ID NO: 11.
    d. a heavy chain CDR1 having the amino acid sequence of SEQ ID NO: 12;
    e. a heavy chain CDR2 having the amino acid sequence of SEQ ID NO: 13; and
    f. a heavy chain CDR3 having the amino acid sequence of SEQ ID NO: 14.
5. The antibody or antigen-binding portion thereof of any of paragraphs 1-4, comprising a light chain having the sequence of SEQ ID NO: 7.

6. The antibody or antigen-binding portion thereof of any of paragraphs 1-5, comprising a heavy chain having the sequence of SEQ ID NO: 8.
7. An isolated antibody or antigen-binding portion thereof that specifically binds to a sMIC polypeptide comprising heavy and light chain complementarity determining regions (CDRs):
   a. a light chain CDR1 having the amino acid sequence of SEQ ID NO: 9;
   b. a light chain CDR2 having the amino acid sequence of SEQ ID NO: 10;
   c. a light chain CDR3 having the amino acid sequence of SEQ ID NO: 11;
   d. a heavy chain CDR1 having the amino acid sequence of SEQ ID NO: 12;
   e. a heavy chain CDR2 having the amino acid sequence of SEQ ID NO: 13;
   f. a heavy chain CDR3 having the amino acid sequence of SEQ ID NO: 14.
8. The antibody or antigen-binding portion thereof of any of paragraphs 1-7, further comprising a conservative substitution in a sequence not comprised by a CDR.
9. The antibody or antigen-binding portion thereof of any of paragraphs 1-8, wherein the antibody or polypeptide is selected from the group consisting of:
   an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, and a bispecific antibody.
10. The antibody or antibody-binding portion thereof of any of paragraphs 1-9, wherein the antibody or antigen-binding portion thereof binds specifically to sMIC.
11. A pharmaceutical composition comprising an antibody or antigen-binding portion thereof of any of paragraphs 1-10 and a pharmaceutically acceptable carrier.
12. A nucleic acid encoding an antibody or antigen-binding portion thereof of any of paragraphs 1-10.
13. The nucleic acid of paragraph 12, wherein one or more of the nucleic acid sequences encoding the CDRs of the antibody or antigen-binding portion thereof are selected from the group consisting of SEQ ID NOs: 1-6.
14. The nucleic acid of paragraph 12, wherein the nucleic acid sequences encoding the CDRs of the antibody or antigen-binding portion thereof are SEQ ID NOs: 1-6.
15. The nucleic acid of any of paragraphs 12-14, wherein the nucleic acid is a cDNA.
16. A method of inhibiting sMIC, the method comprising contacting a cell with or administering to a subject an antibody or antigen-binding portion thereof of any of paragraphs 1-10.
17. A method of treating a MIC-positive cancer in a subject in need thereof, the method comprising administering an effective amount of an antibody or antigen-binding portion thereof of any of paragraphs 1-10 or a pharmaceutical composition of paragraph 11 to the subject.
18. The method of paragraph 17, wherein the MIC-positive cancer is a tumor.
19. The method of paragraph 17, wherein the MIC-positive cancer is an epithelial cell tumor.
20. The method of paragraph 17, wherein the MIC-positive cancer is a hematopoietic malignancy.
21. The method of any of paragraphs 17-20, further comprising administering an additional immunotherapy.

EXAMPLES

Example 1

NKG2D-mediated anti-tumor immunity is evident in experimental animal models. However, whether NKG2D ligands contribute to tumor suppression or progression clinically remains controversial. Described herein are two novel lines of "humanized" bi-transgenic (bi-Tg) mice in which native human NKG2D ligand MICB or the engineered membrane-restricted MICB (MICB.A2) was expressed in the prostate of TRAMP mouse model of spontaneous carcinogenesis. Bi-Tg TRAMP/MICB mice exhibited markedly increased incidence of progressed carcinomas and metastasis, whereas TRAMP/MICB.A2 mice enjoyed long-term tumor-free survival conferred by sustained NKG2D-mediated anti-tumor immunity Mechanistically, it was found that cancer progression in TRAMP/MICB mice is associated with loss of peripheral NK cell pool owing to high serum levels of tumor-derived soluble MICB (sMICB). These findings were also evident in prostate cancer patients. Collectively, this study has not only provided first direct conclusive evidence in "humanized" mouse models demonstrating that soluble and membrane-restricted NKG2D ligands pose distinctive opposite impacts on cancer progression, but also uncovered a novel mechanism of sMIC-induced impairment of NK cell anti-tumor immunity. The present findings indicate that soluble NKG2D ligands permit NK-cell based cancer immunotherapy. The unique mouse models described herein are valuable for optimizing the immunotherapy in this context.

Introduction

NKG2D and its ligands are significant in anti-tumor immunity as evidenced in experimental animal models. NKG2D is an activating receptor expressed by all natural killer (NK) cells, most NKT cells, subsets of γδ T cells, all human CD8 T cells and activated mouse CD8 T cells (1, 2). Engagement of NKG2D can activate NK cells and co-stimulate CD8 and γδ T cells in vitro (3-5). Enforced expression of NKG2D ligand causes tumor cells to be rejected in syngeneic mice in a manner that is dependent on NK cells and, in some cases, primed CD8 T cells (6, 7). Neutralizing NKG2D in vivo with a specific antibody enhances host sensitivity to carcinogen-induced spontaneous tumor initiation (8). NKG2D-deficient TRAMP mice (transgenic adenocarcinoma of the mouse prostate) are three times more likely to develop aggressive poorly-differentiated (PD) prostate carcinoma than NKG2D$^{wt}$ TRAMP counterparts (9). Moreover, in NKG2D$^{wt}$ TRAMP mice, progression to PD prostate carcinoma was mostly associated with down-regulation of NKG2D ligand expression by tumor cells (9).

Curiously, most human tumors, in particular those of epithelial origins express abundant NKG2D ligands yet progress to advanced diseases (10, 11), suggesting that NKG2D function is compromised in cancer patents. Various mechanisms have been proposed to explain how tumor cells evade NKG2D immunity One prevailing concept is that exhaustion of NKG2D function by chronic exposure to its ligands contributes significantly to tumor immune evasion and progression (12-19). However, the prognostic value of NKG2D ligand expression in cancer patients is inconsistent at best (20-24). Levels of NKG2D ligand expression were reported to correlate with better clinical prognosis in colorectal cancer and early stage of breast cancer (22-24), but with poor survival in ovarian and invasive breast cancer (20, 21). Moreover, the underlying mechanisms for NKG2D exhaustion in cancer patients are also in debate. One hypothesis proposes that soluble NKG2D ligands, as a result of tumor-associated shedding, are the negative regulator for NKG2D function and confer the mechanisms of immune evasion. Indeed, clinical data demonstrated that elevated serum levels of soluble NKG2D ligands correlated with advanced epithelial malignancies (13, 14, 25-29). An alternative hypothesis proposes that chronic exposure to membrane-bound NKG2D ligands on tumor cell surface also impairs NKG2D immunity based on observations that constitutive and ectopic expression of NKG2D ligands in normal mouse down-modulates NKG2D function (12, 15, 19).

Currently, there are no suitable mouse models to study the impact of human NKG2D ligands on cancer progression and host immunity due to divergence of NKG2D ligands between human and mice. Although NKG2D function is conserved between human and rodents, the nature and expression pattern of its ligands are highly dissimilar between the two species (10, 31). In humans, known ligands for NKG2D include the major histocompatibility complex (MHC) class I chain-related molecules (MIC) family members MICA and MICB and a family of UL-16 binding proteins (ULBPs) 1-5 (10, 31). In murine systems, the known ligands for NKG2D include the retinoic acid early inducible family of proteins RAE-1, the minor histocompatibility antigen H60 and its variants, and the murine ULBP-like transcript 1 (MULT1) (10, 31). No homolog of human MIC has yet been described in mice. In general, human or mouse NKG2D does not recognize the ligands of their counterparts, except that mouse NKG2D can recognize human MICB and selective alleles of human MICA (32-34). Most importantly, tumor-shedding of NKG2D ligands to down-regulate NKG2D function has been described and proposed as one of the immune evasion mechanisms in human cancer, but has not been described in mice. In mice, NKG2D-mediated suppression of ligand expression on tumor cells was postulated to be the main mechanism of tumor immune evasion (9). These differences create a barrier to study the impact of human NKG2D ligands on cancer progression.

To clarify the impact of human NKG2D ligands on cancer, we exploited the knowledge that the human NKG2D ligand MICB can stimulate mouse NKG2D immunity (33, 34) and generated two unique lines of "humanized" bi-transgenic (bi-Tg) mouse models TRAMP/MICB and the TRAMP/MICB.A2. The former expresses the native human MICB which can be shed by tumor cells whilst the latter expresses an engineered membrane-restricted MICB (designated as MICB.A2) in the prostate of the autochthonous TRAMP mouse (33, 35, 36). Using these models, for the first time the distinct roles of membrane-bound NKG2D ligands and tumor-derived soluble NKG2D ligands on cancer progression are conclusively demonstrated herein. Moreover, it was also uncovered that prostate cancer metastatic progression is associated with profound loss of peripheral NK cells and elevated level of circulating soluble NKG2D ligands in both men and mice.

Results

Bi-Tg TRAMP/MIC mice exhibit accelerated progression to poorly-differentiated (PD) prostate carcinoma and metastasis.

To define the role of NKG2D ligand in tumor progression, the minimal rat probasin (rPb) promoter (35) was used to direct the expression of the native human NKG2D ligand MICB and the engineered membrane-restricted MICB.A2 (36) encoding transgenes to the prostate epithelium in independent lines of C57BL/6 mice (designated as MICB/B6 and MICB.A2/B6 respectively, FIG. 14A-14D). Single copy integration and prostate-specific expression of the transgenes were confirmed respectively by genomic PCR against a limited template dilution standard (data not shown) and RT-PCR (FIGS. 14A-14D). These transgenic mice exhibit normal prostate physiology and immune constitution as wild type B6 animals (FIGS. 14A-14D and 15A-15D).

Figure 1A:
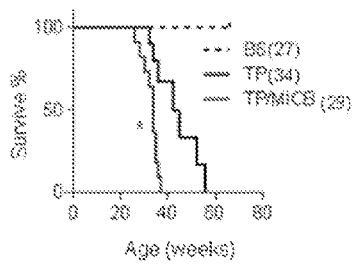
FIGS. 1A-1C demonstrate prostate-specific expression of native human MIC (B) in the mouse model of spontaneous prostate cancer (TRAMP, The transgenic adenocarcinoma of the mouse prostate) promotes the development of poorly-differentiated (PD) prostate carcinoma and metastasis.
Figure 1B:
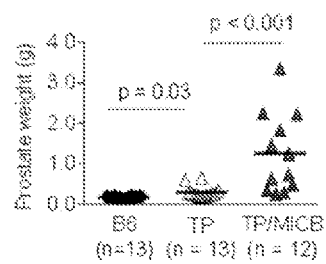
Figure 1C:
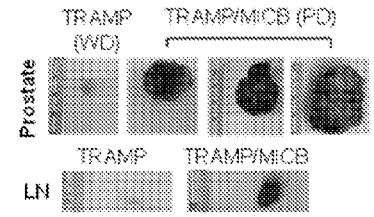

To investigate the role of native human NKG2D ligand on tumor immunity, male MICB/B6 mice were crossed with TRAMP female mice on a B6 background to generate the bi-Tg TRAMP/MICB mice. Normally, male TRAMP mice of B6 background develop hyperplasia and adenocarcinomas by 18 weeks of age and metastatic disease by 30 weeks of age (35, 37), with rare incidence of poorly differentiated (PD) carcinomas. Remarkably, TRAMP/MICB mice elicited much more aggressive tumor growth and progression than TRAMP littermates with significant reduction in overall survival (FIG. 1A and Table 1). When specifically examined at 24 weeks of age, 33% (4/12) of the TRAMP/MICB mice had palpable prostate tumors and had significantly elevated prostate weight at sacrifice in comparison to age-matched TRAMP (n=13) (FIG. 1B). The palpable tumors are grossly large in volume and uniformly to be PD carcinomas in histology (FIG. 1C). Amongst the non-palpable tumors from TRAMP/MICB mice, 75% (6/8) exhibited well-differentiated (WD) carcinomas characterized by intact glandular architecture (Table 1). The remaining tumors (2/8) were mildly-differentiated (MD) carcinomas, a transitional lesion in progression that was characterized by nearly anaplastic sheets of cells with remnants of glandular architecture (data not shown) (37). In age-matched TRAMP male littermates (n=13), only 8% (1/13) had palpable prostate tumor which, however, did not exhibit the pathological characteristics of PD lesions but phylloides-like (PHY) lesions characterized by staghorn luminal patterns (Table 1), similar to a rare lesion in human prostate cancer with unclear prognosis (37, 38). Furthermore, all the four TRAMP/MICB mice that developed palpable PD carcinomas had metastatic deposits in the pelvic draining lymph nodes, lung, and/or liver as confirmed by immunostaining for the SV40T oncoprotein (data not shown). Conversely, none of the 13 age-matched TRAMP littermates had evidence of metastatic lesions in the lymph nodes, lung, liver, or bone (Table 1). These observations demonstrate that expression of native NKG2D ligands MICB accelerated carcinoma progression in TRAMP mice.

Rapid Progression of Prostate Carcinoma in TRAMP/MICB Mice is Associated with Elevated Serum Levels of Soluble MICB (sMICB)

Figure 2A:
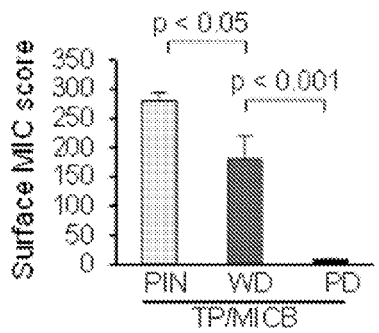
Figure 2B:
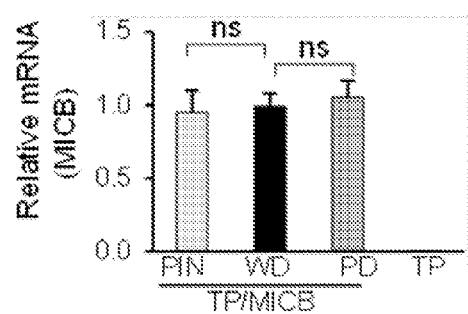
Figure 2C:
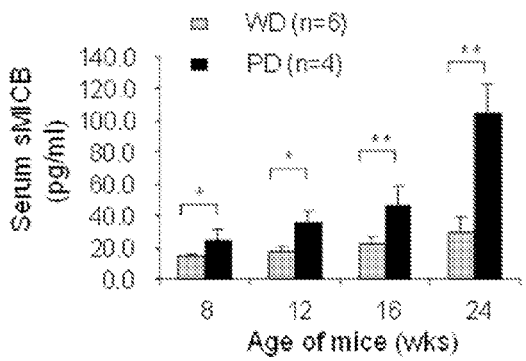
Figure 2D:
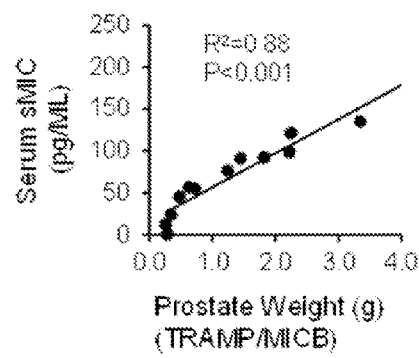

To understand the underlying mechanism that expression of NKG2D ligand MICB expedites the progression of prostate carcinoma in TRAMP mice, MICB expression was examined in the prostate of TRAMP/MICB mice by immunohistochemistry with the monoclonal antibody (mAb) 6D4.6 which is specific for the α1α2 ectodomain of MICA and MICB (11). Interestingly, pre-malignant PIN (prostate intraepithelia neoplasia)-like lesions and WD carcinoma displayed intensive MIC immunostaining, predominantly located on the epithelial cell surface of the prostate gland, whereas little or no MICB expression was detected on surface of PD tumor cells (FIG. 2A). Instead, intense MIC immunostaining in the interstitial space of the PD lesions was seen (data not shown). This pattern of MICB immunoreactivity in WD and PD carcinomas is similar to previous observation of MIC expression in high grade and low grade prostate carcinomas in cancer patients (28). Furthermore, quantitative RT-PCR revealed that MICB was expressed equally in WD and PD lesions at the mRNA level (FIG. 2B), suggesting that the loss of tumor cell surface MICB expression in the PD lesions was due to modifications at the post-transcriptional level. In prostate cancer patients, loss of tumor cell surface MIC was shown to be a result of shedding (28). Serum levels of sMICB in these mice were tracked during carcinoma development. sMICB was detected in all TRAMP/MICB mice at all ages with varying levels (FIG. 2C). However, mice that developed PD carcinomas (n=4) by 24 weeks of age had remarkably elevated levels of serum sMICB compared to those that only developed WD carcinomas (n=6) (FIG. 2C, p<0.01). Furthermore, there is a significant correlation between serum sMIC and final tumor volume as examined at the age of 24 weeks old (FIG. 2D, $R^2$=0.88, p<0.88). Together, these data indicate that the progression to PD carcinomas in TRAMP/MICB mice was associated with loss of tumor cell surface membrane-bound MICB and elevated serum levels of sMICB.

Tumor shedding of NKG2D ligands to impair its receptor function has been demonstrated in many types of human cancers and proposed to be one of the mechanisms of immune evasion. In TRAMP mice, however, tumors have been shown to evade NKG2D immune surveillance via an alternative mechanism. Guerra et al. have demonstrated that expression of the endogenous NKG2D ligand, e.g. RAE-1, was downregulated by the receptor NKG2D during tumor progression (9). To address whether this alternative mechanism contributes, at least in part, to the development of PD tumors in TRAMP/MICB mice, the expression of RAE-1, the most abundantly expressed endogenous mouse NKG2D ligand in TRAMP tumors (9), was examined. Comparable mRNA and protein levels of RAE-1 expression were found in PD and WD tumors from TRAMP/MICB mice (FIGS. 2E-2F). These data indicate that development of PD carcinoma in TRAMP/MICB mice is not due to immune editing of endogenous NKG2D ligand expression. Thus, tumor-derived sMICB accounts for the major cause of tumor progression.

sMICB Perturbs Nk Cell Peripheral Maintenance and Facilitates Tumor Metastasis

To understand the mechanisms by which sMICB facilitates tumor progression, splenic CD8 T and NK cell populations and their NKG2D expression in TRAMP/MICB mice vs. their TRAMP littermates were examined. All the TRAMP/MICB and TRAMP mice had comparable frequency and absolute numbers of splenic CD8 T cells (FIGS. 3A and 16A). Only a small fraction of the CD8 T cells expressed NKG2D and the expression levels were not significantly different between TRAMP/MICB and TRAMP mice. Given that NKG2D is only expressed by activated mouse CD8 T cells and that antigen-specific CD8 T cell tolerance is well-documented in TRAMP mice (39, 40), this observation is expected. Intriguingly, the frequency and absolute number of NK cells in the spleen were significantly reduced in TRAMP/MICB mice that developed PD carcinomas and metastasis (FIGS. 3B and 16B). There was a significant inverse correlation between serum levels of sMICB and numbers of residual splenic NK cells in the cohort of TRAMP/MICB mice (FIG. 3C, p=0.02, $R^2$=−0.94). No major difference in the splenic NK cell population was observed among the TRAMP littermates.

It was further addressed whether sMICB-associated depletion of splenic NK cells in TRAMP/MICB mice is a systemic effect or splenic-specific effect due to impaired trafficking. Despite marked reduction of splenic NK cells in association with high serum levels of sMICB, no accumulation of $CD3^-NK1.1^+$ cell population in the lymph nodes or bone marrow was seen. Rather, a significant reduction of NK cell frequency in the lymph nodes was also observed (FIG. 3D). Only a modest but not significant reduction of NK cells was seen in the bone marrow (FIG. 3D). Consistent with the findings in the peripheral lymphoid organs, NK cell infiltration in the tumor parenchyma of PD carcinomas was also significantly reduced (FIG. 3E), whereas CD8 T cell infiltration was not affected (FIG. 16C). Nevertheless, $NKG2D^+$ CD8 T cells were significantly reduced among CD8 T cells infiltrated in the PD carcinomas (FIG. 16C). These observations indicate that the loss of NK cells in the secondary lymphoid organs is not due to development block or increased egress of NK cells into the tumor parenchyma.

Figure 4B:
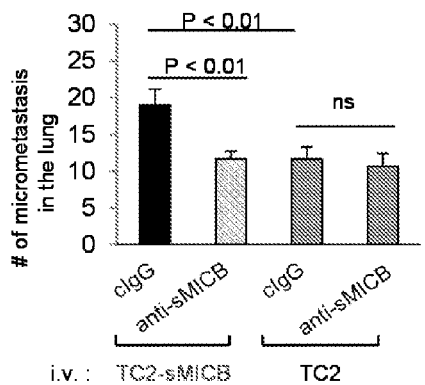
Figure 4C:
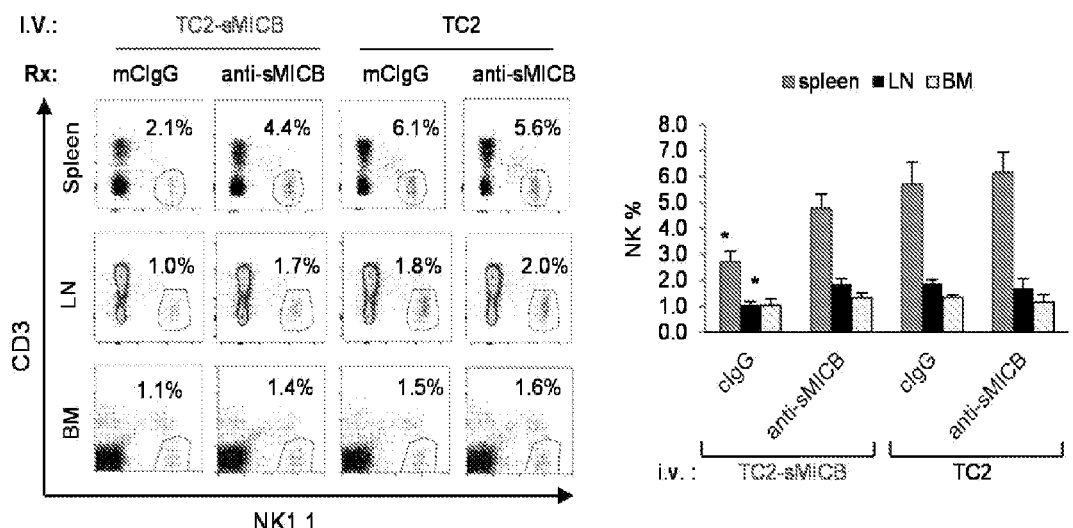
Figure 4D:
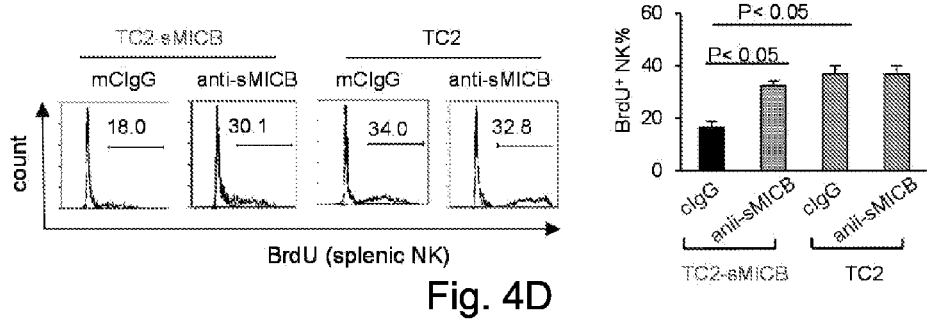

To confirm that tumor progression and metastasis is facilitated by sMICB through impairing NK cell homeostasis, the growth characteristics of TRAMP carcinoma-derived syngeneic metastatic cell line TRAMP-C2 (TC2) (41, 42) with and without sMICB expression after intravenous inoculation were determined (FIG. 4A). Three weeks post-implantation, animals were treated with the sMIC-neutralizing antibody P2B10G5 or control IgG for two-week duration (FIGS. 17A-17C). As expected, micro-metastatic deposits in the lung were significantly higher in mice implanted with TC2 cells expressing sMICB (TC2-sMICB) than in those implanted with TC2 cells (FIG. 4B) (microscopy image data not shown). Concomitantly, a significant reduction of NK cells were found in the spleen, LN, and lung of mice implanted with TC2-sMICB cells with comparison to those implanted with TC2 cells (FIGS. 4C, and 18) (microscopy image data not shown). Moreover, lung micro-metastatic deposits of TC2-sMICB were significant reduced by sMIC-neutralizing antibody (FIG. 4B) (microscopy image data not shown), with the concurrent restoration of peripheral pool of NK cells (FIG. 4C). By BrdU pulsing, it was found that highly proliferating NK cells failed to accumulate in the spleen of TC2-sMICB-bearing mice, but restored with the treatment of sMICB-neutralizing antibody (FIG. 4D). Taken together, these data clearly show that sMICB facilitates metastasis of tumor cells and such an activity is associated strongly with disruption of NK cell peripheral maintenance.

Figure 5A:
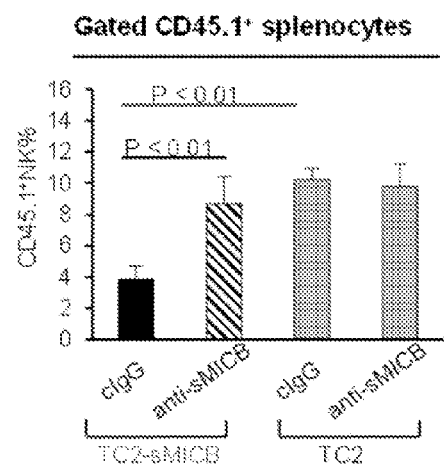
FIGS. 5A-5D demonstrate that sMIC perturbs adoptively transferred NK cell proliferation in transplanted metastatic TRAMP-C2-sMIC mice. $1 \times 10^7$ V$_{450}$-labeled CD45.1$^+$ congenic splenocytes were transferred into CD45.2$^+$ mice that were implanted with TRAMP-C2-sMICB or TRAMP-C2 mice. These mice were treated with sMICB-neutralizing antibody (mAb B10G5) or control IgG (cIgG) before and after receiving CD45.1$^+$ congenic splenocytes. Mice were euthanized five days after congenic transfer.
Figure 5B:
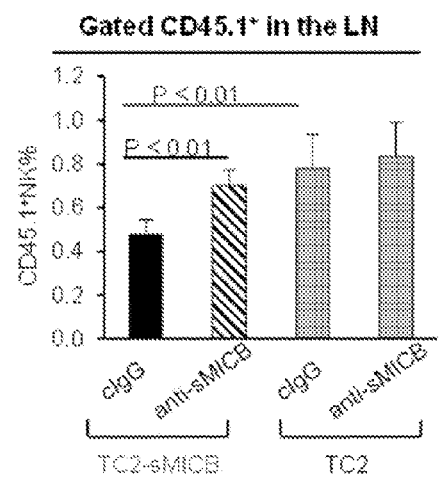
Figure 5C:
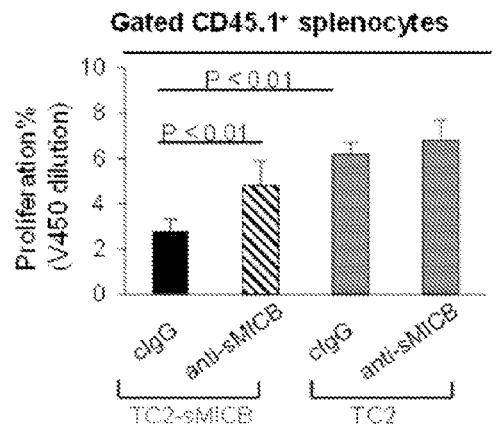
Figure 5D:
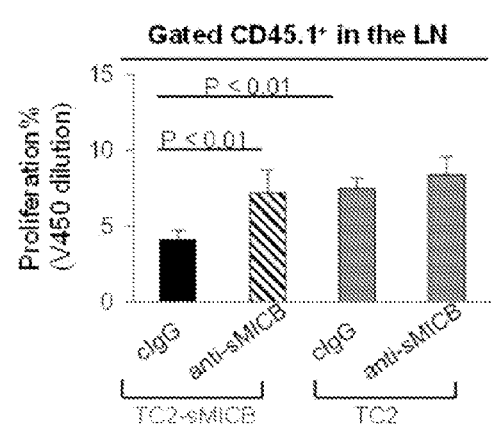

To further address if the maintenance of established NK cell population is negatively affected by sMICB and to confirm the potential underlying mechanisms, cell trace dye V450-labeled congenic $CD45.1^+$ splenocytes were adoptively transferred into mice four weeks post-implantation with TC2 or TC2-sMICB cells as described above. These mice were pre-treated with sMIC-neutralizing antibody P2B10G5 or control IgG (twice weekly) one week prior to the transfer. Five days post-transfer, the frequency of congenic NK cells in the spleen and lymph nodes was examined. In comparison with mice implanted with TC2 cells, mice that were implanted with TC2-sMICB cells had significantly reduced frequency of $CD45.1^+$ NK cells in both spleens and lymph nodes (FIGS. 5A, 5B and 19A). However, treatment with sMIC-neutralizing antibody led to a significant increase of congenic $CD45.1^+$ NK cells in mice inoculated with TC2-sMICB cells (FIGS. 5A, 5B, and 19A). The sMIC-neutralizing antibody did not have a significant effect on the frequency of $CD45.1^+$ NK cells in mice implanted with TC2 cells (FIGS. 5A, 5B, and 19A). V450 dilution analyses of the transferred congenic $CD45.1^+$ cells revealed a significant increase in proliferation of $CD45.1^+$ NK cells in both spleen and lymph nodes with the treatment of sMIC-neutralizing antibody in mice implanted with TC2- sMICB cells (FIGS. 5C, 5D, and 19B). A significant difference of the expression of NK cell homing receptor CD62L in the spleen or lymph nodes among all groups of animals was not detected (FIG. 19C), indicating that sMIC-associated loss of NK cell in the peripheral was not likely due to impaired NK trafficking. This adoptive transfer experiment has clearly and conclusively demonstrated that sMICB perturbs NK cell peripheral maintenance, in part through impairing NK cell proliferation.

Stable Expression of the Non-shedding Membrane-bound NKG2D Ligand by Tumor Cells Prevents Tumorigenic Progression To further determine that tumor progression in TRAMP/MICB mice is driven by sMICB rather than tumor surface MICB and to define the role of membrane-bound NKG2D ligands in tumor immunity, bi-Tg MICB.A2/TRAMP mice were generated by crossing male MICB.A2/B6 mice to female TRAMP (B6 background) mice. Of note, the engineered MICB.A2 was generated by replacing a shedding regulatory region of MICB with corresponding sequence of HLA-A2. MICB.A2 could not be shed from tumor cell surface and is membrane-restricted (36). Overall, more than 90% of the TRAMP/MICB.A2 mice remained long-time tumor-free survival (FIG. 6A). When cohorts of TRAMP/MICB.A2 mice was examined at 24 weeks of age, prostate weights (0.20±0.01 g) were only slightly higher than wild type B6 littermates (0.17±0.01 g; p=0.16) but significantly lower than TRAMP littermates (0.30±0.04 g; p<0.01, FIG. 6B). Remarkably, no single TRAMP/MICB.A2 mouse developed prostate carcinoma. The normal architecture of prostate gland was mostly preserved demonstrated by p63 immunostaining (data not shown). Amongst the 21 TRAMP/MICB.A2 mice, prostate glands from eight animals exhibited normal histology with intact basal cell layers. Prostates from the remaining 13 of these animals exhibited varying grade of PIN-like lesions represented by reduced p63-positivity in the interior of the multilayered lesions and an increased ratio of luminal cell to p63-positive basal cells (data not shown) (37). Furthermore, the SV40T oncogenic protein which drives carcinoma development in TRAMP mice remained present in epithelium of the prostates from all TRAMP/MICB.A2 mice (35). Importantly, no soluble form of sMICB was detected in the sera of these animals (FIG. 6C). These data clearly demonstrate that membrane-bound form of MICB suppresses prostate cancer oncogenesis and progression.

To ascertain that tumor suppression in TRAMP/MICB.A2 mice is mediated by NKG2D immunity as a consequence of prostate-specific expression of MICB.A2, cohorts of TRAMP/MICB.A2 mice (n=6/cohort) of 16 to 18-week-old were treated with the NKG2D blocking antibody C7 or control rat IgG twice weekly for an 8-week duration. Without an exception, all the mice treated with C7 had elevated prostate weight and developed prostate carcinoma (FIG. 6D and data not shown).

Remarkably, unlike TRAMP/MICB mice which had significant reduction of NK cells in the spleen (FIGS. 3A-3E), the frequency of both NK and CD8 T cell population was comparable to TRAMP or wild type B6 littermates (FIGS. 7A-7D). The level of NKG2D expression on NK cells in TRAMP/MICB.A2 mice was also unperturbed (FIG. 7A). Moreover, when stimulated with NKG2D ligand RAE-1 expressing cell line ex vivo, splenic NK cells from TRAMP/MICB.A2 and wild type mice showed comparable levels of IFN-γ production and NKG2D-dependent cytotoxicity (FIGS. 7B and 7C). Moreover, the splenic NKG2D$^+$CD8 T cells increased in frequency in TRAMP/MICB.A2 mice in comparison to TRAMP littermates although total CD8 T cell frequency remains similar (FIG. 7D). This data supports the notion that expression of membrane-bound NKG2D ligands on tumor cells promotes CD8 T cell response because NKG2D expression correlates with the activation status of mouse CD8 T cells (6). Collectively, these data provided direct in vivo evidence that sustained expression of membrane-bound form of NKG2D ligand does not impair, but rather stimulates host immunity to suppress tumorigenic progression.

Metastatic Prostate Cancer in Men is Associated with Reduced Peripheral NK Cells and Elevated Serum sMIC To understand the clinical significance of these findings, CD3$^-$CD56$^+$ NK cell population in the peripheral blood of 36 newly diagnosed treatment-naïve prostate cancer patients with varying Gleason Scores, of whom 11 had distant metastatic diseases and 25 had only localized diseases was analyzed. It was found that the frequency of circulating NK cells was profoundly reduced in prostate cancer patients (n=36) in comparison to age-matched healthy men (n=10). Strikingly, men who developed metastatic diseases had significant lower frequency of circulating NK cells, than those who were only diagnosed with localized diseases (FIG. 8A). No significant difference was observed in circulating T cells (CD3$^+$CD56$^-$) among all the analyzed subjects (FIG. 8B). Moreover, serum levels of sMIC were significantly higher in men with metastatic disease than those with localized diseases (FIG. 8C). Furthermore, there is a significant inverse correlation between the serum levels of sMIC and NK cell frequency in the circulation (FIG. 8D). No correlation of T cell frequency with sMIC was found (data not shown). These data revealed a clear association of prostate cancer metastasis with loss of NK cell in the peripheral lymphocyte pool and high serum levels of sMIC in patients and confirms the close immunological and pathological similitude of the TRAMP/MIC mouse model to prostate cancer patients.

Generation and characterization of sMIC-neutralization monoclonal antibody P2B10G5. Two balb/c mice were immunized with purified recombinant soluble MIC (rsMIC) three times at two weeks intervals. A 100μg weight of the conjugated KLH peptide in Freund's complete adjuvant was used for the first immunization. At the subsequent immunizations, 50 μg of the KLH peptide in incomplete Freund's adjuvant were administered. One week prior to the last immunization, blood was collected and antibody titers were determined by ELISA using rsMIC coated plates. Hybridomas were generated by fusing splenocytes from immunized mice with the murine myeloma cell line SP2/0 using polyethylene glycol. Fusion hybrids were selected using HAT medium and the reactivity of the secreted antibody was tested by ELISA and flow cytometry analysis against C1R and C1R-MIC cells. Antibody produced by one of the hybridoma p2B10G5 was purified by BioXcell (Labnon, N.H.).

Discussion

Ample evidence from experimental animal models supports the significance of NKG2D function in tumor immunity. However, to date studies have not been able to clarify, whether sustained expression of NKG2D ligands on tumor cells or chronic exposure of NKG2D to its ligands expressed on tumor cells is most beneficial for tumor immunity (12, 15, 19). To this end, novel "humanized" bi-Tg TRAMP/MIC and TRAMP/MIC.A2 mouse models were established in which a human NKG2D ligand was specifically expressed on a spontaneous tumor with concurrent expression of the oncogenic protein SV40T, closely emulating human cancers. Moreover, we differentially expressed two forms of NKG2D ligands to distinguish their effects on tumor progression: the native NKG2D ligand MIC which can be shed by tumors to generate the soluble form as naturally occurred in cancer patients and the mutant membrane-restricted NKG2D ligand MIC.A2 which could not be shed from tumors. With these two lines of mouse models, it was for the first time clearly demonstrated that membrane-restricted and soluble NKG2D ligands pose opposite impact on tumor progression and metastasis. This conclusively demonstrates that membrane-restricted NKG2D ligand MIC.A2 could sustain NKG2D protective immunity and prevent spontaneous tumorigenesis and that native NKG2D ligand MIC facilitates tumor progression through soluble ligand-mediated impairment of NK cell peripheral maintenance.

Mechanisms, such as down-modulation of NKG2D expression by tumor-derived soluble NKG2D ligands (13, 14, 25, 28, 43) and TGFβ (44) and obstructing MIC-NKG2D interaction by core2 O-glycans (45), have been described as tumor-immune evasion of NKG2D-mediated immunity. A novel observation was made in the current study regarding the profound impairment of NK cell homeostasis in both mice and men by tumor-derived soluble NKG2D ligands. It was found that peripheral NK cells were significantly depleted as a result of high levels of circulating sMIC in bi-Tg TRAMP/MIC mice. This tumor evasion mechanism was further confirmed in an experimental lung TRAMP-C2-sMIC model and also indicated to be of significance in prostate cancer patients. As shown in the animal models, depletion of NK cells was most profound in the peripheral lymphoid organs and less so in the bone marrow, suggesting that homeostatic maintenance of NK cell pool in the peripheral was affected. This point was further strengthened by the adoptive transfer experiment where it was observed the depletion of proliferating NK cells by soluble MIC that can be reversed by treatment of neutralizing antibody. These findings are intriguing and provide explanations, at least in part, for many clinical observations.

For instance, decreased intra-tumoral NK cell number has been found to predict a poor clinical outcome in certain type of cancer patient (46, 47). Also, retrospective studies suggest that serum sMIC has a predictive value for epithelial cancer progression to metastasis (13, 14, 29). The failure of clinical trial of adoptive NK cell transfer to treat human malignancy (48, 49) may also be explained in part by soluble NKG2D ligand mediated NK cell depletion. One of the challenges for improving the therapeutic outcome is to sustain infused NK cells in cancer patients (48, 49). The current study indicates that elimination of soluble NKG2D ligands is a viable avenue to explore to improve NK cell-based cancer immunotherapy. Further studies are necessary to uncover the cellular and molecular mechanism by which sMIC impairs NK cell peripheral homeostasis.

The finding that membrane-bound NKG2D ligand protects anti-tumor immunity contradicts the conclusion from other reports that chronic exposure to membrane-bound ligands impairs NKG2D function and thus increases susceptibility to tumorigenesis (15, 19). It is contemplated herein that the discrepancy lies in the differences among various experimental models. In two studies, the ligand of NKG2D was constitutively and broadly expressed in non-tumor prone wild type mice (15, 19), which is highly non-physiological relative to expression in a tissue-specific fashion in the context of a spontaneous tumor. For instance, one transgenic mouse model that was created by expressing human MIC under the constitutive and ubiquitous mouse MHC class I H-2K$^b$ promoter on a C57BL/6 background showed impaired ability of NK cells to reject MICA-transfected RMA tumors in comparison to the wild-type counterparts (19). In other models (15), NKG2D ligand RAE-1ε was expressed in normal mice under the constitutive involucrin promoter (inducing squamous epithelium expression) or the ubiquitous chicken β-actin promoter; local and systemic NKG2D downregulation was noted in these mice in comparison to the wild-type counterparts. Notably, in these transgenic mouse models, NKG2D ligand expression was "ectopic" and under the direction of a constitutive or ubiquitous promoter in somatic cells. Given the magnitude of ligand-induced NKG2D signaling on activating NK cells, down-modulation of NKG2D function is expected in these transgenic mice in comparison to an otherwise wild type counterpart as a self-regulatory mechanism to allow normal embryonic development. Thus, although the findings from these mouse models are interesting, they do not represent the real situation in cancer patients. In contrast, described herein are unique transgenic mice that express NKG2D ligands in the prostate that is prone to develop cancer spontaneously due to concurrent expression of SV40 T antigen. The organ-specific and temporal expression of NKG2D ligand during cancer progression closely resembles that in human cancers. The results described herein reflect more closely what is happening in human patients, which is validated by consistent clinical observations: prostate cancer progression correlated profoundly with increased soluble MIC and concurrent depletion of NK pool in the circulation.

Most studies did not specify if NKG2D ligands present on tumor tissues were membrane-bound or soluble. This ambiguity may account for the contradiction in prognostic value of NKG2D ligands in patients, even with the same type of cancer at different disease stages. For example, high expression of NKG2D ligand MIC in tumors was reported to predict a good prognosis for early breast cancer but a poor prognosis for invasive breast carcinoma (21, 24). Tumor shedding of sMIC is mediated by members of matrix metalloproteinase (MMP) families (50, 51). One of the members, MT1-MMP that is shown to mediate MIC shedding (50), is upregulated in invasive breast carcinomas and its expression gave a poor clinical prognosis in patients with invasive breast cancer (52). Thus, it is possible that different forms of NKG2D ligands were detected in early and invasive breast cancer tissues. Because soluble NKG2D ligands negatively regulate the function of multiple anti-tumor effector cells within tumor tissue and systemically, it is contemplated herein that a combination of vigilant scoring of NKG2D ligand expression in tumor tissues with serum levels of sMIC can provide an accurate prognosis of a malignancy.

In summary, described herein is a unique mouse model of spontaneous carcinoma that recapitulates the specific interactions between NKG2D and its cognate ligands during tumor progression. It is further demonstrated that metastatic progression of prostate cancer is associated with loss of NK cells in the circulating and high levels of soluble MIC in both mice and men. The present study not only clearly defines the impact of NKG2D ligand expression on tumor progression but also presents a valuable pre-clinical autochthonous mouse model that can be exploited to develop and optimize cancer immunotherapy based on the biology of NKG2D and its ligands.

Methods

Human Blood Sample Collection. The collection and the use of human peripheral blood samples and relevant clinical information were approved by the University of Washington Institutional Review Board and the Medical University of South Carolina. All subjects gave written informed consent for the study. Blood samples of treatment-naïve and newly diagnosed prostate cancer patients (n=36, age 52-79) were obtained from the outpatient Urology Clinics at the Veterans Affair Puget Sound Health Care System, Seattle Cancer Care Alliance, and Hollings Cancer Center. All subjects enrolled in this study have normal white blood cell count (4,000-11,000 cells/microliter). 25 of these men were diagnosed with localized diseases only. 11 of these men were diagnosed with distant metastasis (bone or lymph nodes). Blood samples from healthy control age-matched men (n=10, age 50-68) were obtained from human subject recruited at the University of Washington. Healthy subject was defined as no history of cancer and no immunological disorder. Whole blood was collected in heparinized tubes. Serum was collected and PBMCs were separated by Ficoll-Hypaque density.

Transgenic Mice. Mice were bred and housed under specific pathogen-free conditions in the animal facility of the University of Washington and the Medical university of South Carolina in accordance with institutional guidelines with approved IACUC protocols. All mice used in this study were on the C57BL6 (B6) background. The rPB-MICB and rPB-MICB.A2 expression cassette were constructed by replacing the SV40T fragment from rPB-SV40T expression cassette (35) with the cDNA fragments encoding MICB or MICB.A2 respectively. The cDNA encoding for MICB.A2 was similarly described (33). Briefly, a small region of MICB α3 domain (aa 238-252) spanning the motif that regulates MICB shedding (36) was replaced with corresponding sequence from HLA.A2. The molecule MICB.A2 has the same function as MICB in recognition of NKG2D (33, 36). The entire rPB-MICB or rPB-MICB.A2 expression cassette was gel purified following digestion with HindIII and was microinjected into fertilized B6 embryos respectively (performed at University of Washington Comparative Medicine transgenic core facility). Transgenic progeny were identified by PCR analysis of DNA extracted from tail biopsies using the forward primer specific for rPB (5'-acaagtgcatttagcctctccagta-3') and the reverse primer specific for MICB (5'-tgtgtcttggtcttcatggc-3') or MICB.A2 (5'-cagagacagcgtggtgagtcatatg-3').

The male rPB-MICB and rPB-MICB.A2 animals were bred with female TRAMP mice to generate the experimental male TRAMP-MICB and TRAMP-MICB.A2 animals. Presence of double transgenes was identified by PCR analysis of DNA extracted from tail biopsies using the primers specific for SV40Tag (Forward 5'-gatatggctgatcatgaacagact-3' and Reverse 5'-tttgaggatgtaaagggcactg-3') and MICB or MICB.A2 as described above. All experimental mice were randomly assigned to cohorts and sacrificed at defined age for evaluation. In some cohorts, animals were administrated i.p. with anti-NKG2D blocking antibody C7 (100 μg/mouse, eBiosciences) or control IgG twice weekly for an 8-week duration. Prostates, lymph nodes, liver, lung, and femur were collected for histological evaluation. In some experiments, LN and bone marrow were also collected along with spleens for single cell suspension and immunological evaluation. Blood were collected for assaying serum levels of sMICB by ELISA.

Experimental lung metastatic model. TRAMP-C2 (TC2) or TC2 cells expressing soluble MICB (TC2-sMICB) were i.v. transplanted into two groups of syngenic MICB/B6 transgenic mice (n=6) ($0.5 \times 10^6$ cells/mouse) at the age of 8-10-week old. As mice do not naturally express homologs to human MIC, we chose to use the transgenic MICB/B6 mice instead of B6 mice in this experiment to avoid the effect of autoantibody against the human molecule sMICB during the experiment. Six week post-transplantation, mice in each group were further randomized into two subgroups: with anti-MICB mAb p2B10G5 (or named as B10G5) treatment or control mouse IgG. Each mouse in the treatment group received i.p. the dose of 100 μg mAb p2B10G5 or mouse IgG twice weekly for two weeks before sacrifice. For BrdU feeding, mice were supplies with 0.8 mg/ml of BrdU (Sigma) in drinking water with daily refreshing. For congenic experiments, $1 \times 10^7$ congenic CD45.1$^+$ splenocytes were labeled with Cell Trace Dye V450 before being i.v. transferred into each mouse. After euthanization, spleens, bone marrows, and LNs were harvested for single cell suspension analyses. Lung were harvested, fixed in 10% neutral fixation buffer, paraffin embedded and sectioned for histology evaluation.

Histological and Immunohistochemical Examination. The mouse prostate and other soft tissues were fixed in 10% formaldehyde and embedded in paraffin wax. The bone tissues were de-calcificated for 24 h before embedded. Five-micrometer sections were cut and stained with H&E for pathological evaluation. Sections were also stained with: 1) anti-MICB (and MICB.A2) mAb 6D4.6 (mouse IgG; 1:500; Biolegend); 2) anti-panRAE-1 antibody (Rat mAb IgG2a; 1:500; R&D); 3) anti-SV40T antigen (Rabbit polyclonal IgG, 1:200; Santa Cruz); 4) anti-mouse p63 antibody (Mouse mAb IgG2a; 1:200; Thermo Scientific). Sections were deparaffinized, incubated for 10 min in 10 mM citrate buffer (pH 6.0) at 95° C. for antigen retrieval. Endogenous peroxidase activity was quenched with 3% hydrogen peroxide. After quenching endogenous peroxidase activity and blocking nonspecific binding, slides were incubated with specific primary antibody overnight at 4° C. followed by subsequent incubation with the appropriate biotinylated secondary antibody: goat anti-rabbit IgG (Vector, Burlingame, Calif.); rabbit anti-rat IgG (Vector); goat anti-mouse IgG (Vector) at a 1:1000 dilution for 20 minutes at 37° C. Immunoreactive antigens were detected using the Vectastain Elite ABC Immunoperoxidase Kit and DAB. All slides were counterstained with hematoxylin (Vector) and mounted with Permount (Fisher Scientific).

IHC Evaluation. Scoring of the IHC staining was similarly described previously (53). Briefly, the intensity of specific staining was double-blind graded on a scale of 1 to 3 (1=weak staining, 2=moderate staining, and 3=strong staining) A semiquantitative score on a 10% increment scale ranging from 0 to 100% was used to assess the percentage of stained cells of the intensity. Approximately 500 cells were analyzed for each case. The final composite staining score for immunostaining was based on the intensity of staining (1, 2, or 3) multiplied by the percentage of immunopositive cells (0-100). The maximum composite score is 300.

Pathological Evaluation. Ten randomly selected fields of H&E-stained sections of the prostate from individual mouse of each cohort were independently scored by two scientists for incidence and percentage of area corresponding to each pathologic stage. Pathologic grading of the prostate was performed according to the recommendations of published studies (35, 38).

Flow Cytometry Analysis. For analyses of NK cell frequency in human PBMC, single cell suspension was stained with FITC-conjugated anti-human CD3 and PE-conjugated anti-human CD56 antibodies (eBiosciences). Samples were analyzed with BD FACScan™. NK cells were defined as CD3$^-$CD56$^+$. For analyzing mouse samples, single cell suspensions of splenocytes, LN and bone marrow were incubated on ice for 30 min with a combination of FITC-conjugated mNK-specific mAb NK1.1 or DX5 or mCD8-specific antibody (ebiosciences) in combination with PE-conjugated anti-mouse NKG2D mAb CX5 (ebioscience) and PerCP-conjugated anti-mouse CD3 antibody (eiosciences). Cells were analyzed using a BD FACscan™ or Fortessa™. Data were analyzed using the BD FlowJo™ software (Tree Star).

Cytotoxicity Assay. Mouse NK cells were isolated as previously described from pooled splenocytes from two to three representative mice with similar prostate disease progression within the same experimental group were used as effectors (33). $^{51}$Cr-labeled TRAMP-MICB.A2 cells were used as target cells. Cyotoxicity assay was performed using standard 4-hour $^{51}$Cr release assay as described previously (33). 30 µg/ml of anti-NKG2D antibody C7 (ebioscience) was for blocking NKG2D function.

ELISA for sMIC. Serum was diluted 1:2 with PBS. Amount of soluble MIC in human serum was measured using MICA DuoSet™ sandwich ELISA kit (R&D Systems) following manufacture's protocol. Amount of soluble MICB in mouse serum was measured using human MICB Duo-Set™ sandwich ELISA kit (R&D Systems) as previously described (33).

Statistical Analysis. All statistical data were expressed as mean±SEM. Difference between means of populations was compared by standard Student's t-test for unpaired, one-tailed samples. Survival was determined via Kaplan-Meier analysis with comparison of curves using the Mantel-Haenszel log-rank test. A p value of 0.05 or less was considered significant. The GraphPad Prism™ software was used for all analyses.

Example 2

Antibody Neutralizing Soluble NKG2D Ligand Revives Host Anti-tumor Immunity and Alleviates Advanced Prostate Cancer Activation of the c-type lectin-like stimulatory receptor NKG2D is important for maintaining anti-tumor immunity. Retaining NKG2D ligands on tumor cell surface is critical for sustaining NKG2D-mediated tumor suppression. In cancer patients, shedding of NKG2D ligands by cancer cells down-regulates NKG2D receptor expression in CD8 T cells and NK cells and, thus, compromises NKG2D-Mediated immune surveillance. More severely, chronic exposure to soluble NKG2D ligand can induce depletion of peripheral NK cells, which is particularly profound in patients who progress to metastatic diseases. Levels of serum soluble NKG2D ligands have been proposed as a potential prognosis biomarker for metastasis of human malignancies. Whether neutralizing circulating soluble NKG2D ligand can be an effective treatment for metastatic malignancy has never been tested.

In human malignancy of solid tumors, the most-abundantly expressed NKG2D ligands are the MHC I-chain related molecules A and B (MICA/B). Shedding of MIC has been shown to correlate with disease stages of various types of human cancer. Given the fact that no human MIC homolog is identified in rodents and that regulation of NKG2D-function in tumor bearing host is implied with an alternative mechanism, described herein is a "NKG2D-ligand humanized" mouse prostate tumor TRAMP/MIC model and demonstration of the simulation of this model to men with prostate cancer pathologically and immunologically. In this study, it is demonstrated that neutralizing serum soluble MIC with a monoclonal antibody dramatically induces regression of advanced prostate cancer and suppresses metastasis. The therapeutic effect is through restoring NK cell homeostasis and priming CD4 and CD8 T cell anti-tumor immunity.

Results

Figure 9A:
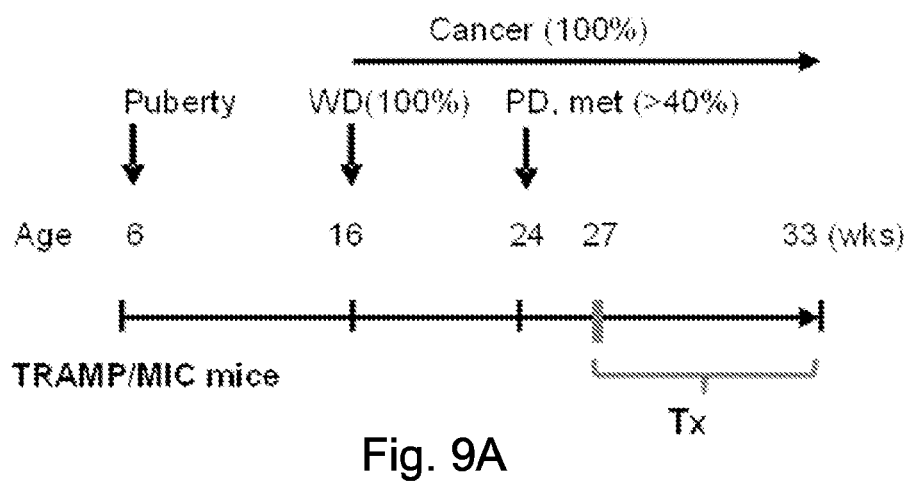
FIGS. 9A-9D demonstrate that treatment with p2B10G5 caused marked regression of Primary prostate carcinoma and inhibited metastasis.
Figure 9B:
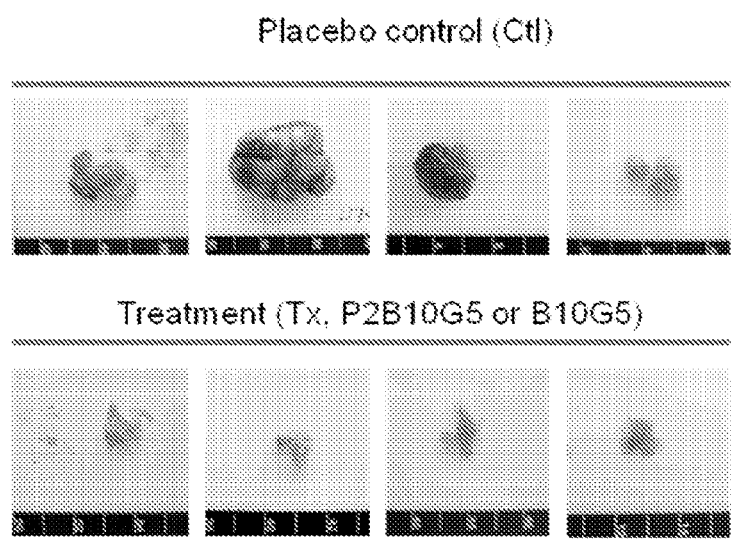
Figure 9C:
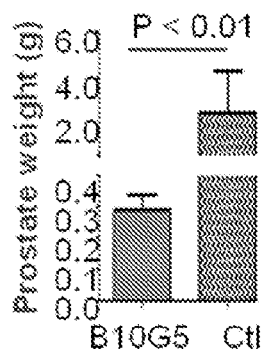
Figure 9D:
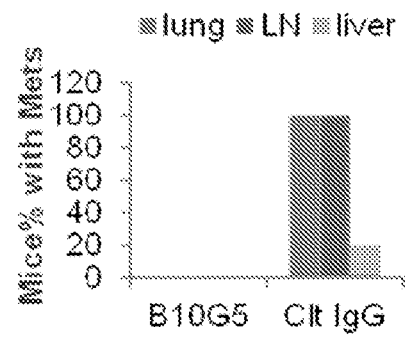

Antibody Neutralizing sMIC Causes Regression of Advanced Prostate Cancer and Suppresses Metastasis As described herein, more than 40% of the "NKG2D ligand humanized" TRAMP/MIC mice develop poorly differentiated prostate carcinoma and metastasis by 24 week of age, as a result of tumor shedding of sMIC. A cohort of 27 to 28-week old TRAMP/MIC mice were treated with the monoclonal antibody, "P2B10G5", which is specific to the extracellular domain of human MICA and MICB, or control mouse IgG (Placebo), twice weekly by intraperitoneal injection at 30 mg/KG body weight (FIG. 9A). After 6 weeks of treatment, all mice in the antibody treated group were generally healthy whereas all the mice in the control group showed severe symptoms of illness. When examined, all the animals in the antibody treated group had significantly smaller prostate size in compare to the control group large tumors (FIG. 9B). Prostate weight of treated mice is remarkably decreased in comparison to which in the control group (FIG. 9C). No metastasis was observed in the lymph nodes or lung in the antibody treated mice. Conversely, 100% of the mice in the control group had lung or lymph node metastasis (FIG. 9D).

The Antibody Treatment Causes Significant Apoptosis of Tumor Cells as Shown by Cleaved Caspase-3 Immunohistochemistry Staining (Data not Shown).

No significant systemic cytotoxicity was observed in association with the treatment. Animals in the control placebo had significantly higher body weight than the treated group (FIG. 10A), due to large tumor burden Animals with the antibody treatment only had a tendency of weight loss, but not significant (FIG. 10A). The weight change may due to the treatment response of systemic cytokine storm (FIG. 10B). The antibody treatment significantly decreased serum levels of sMIC (FIG. 10C).

Antibody Treatment Restores NK cell Homeostasis and Enhances NK Cell Function

Figure 11A:
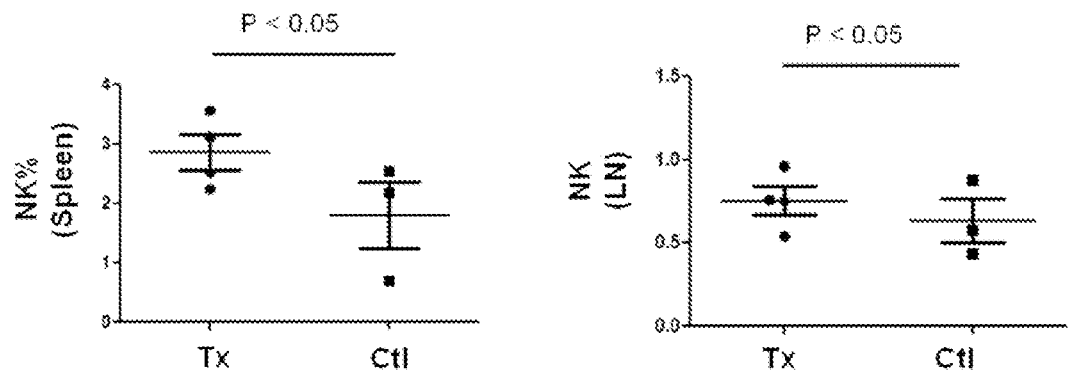
FIGS. 11A-11C demonstrates that antibody treatment enhanced NK cell homeostasis and function.
Figure 11B:
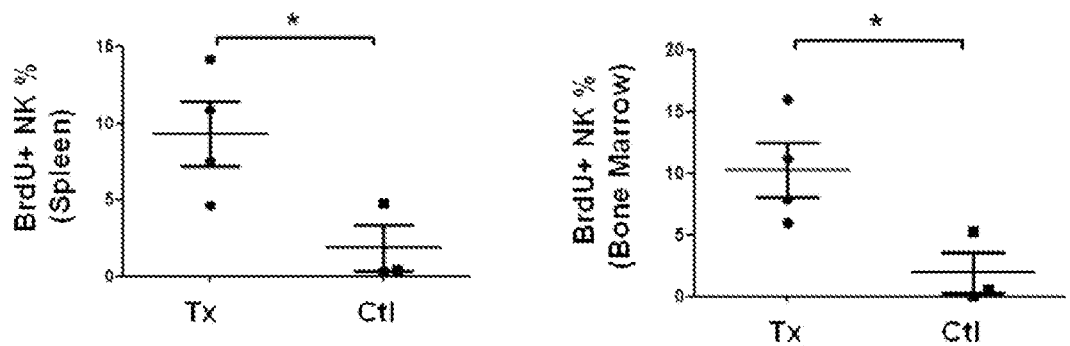
Figure 11C:
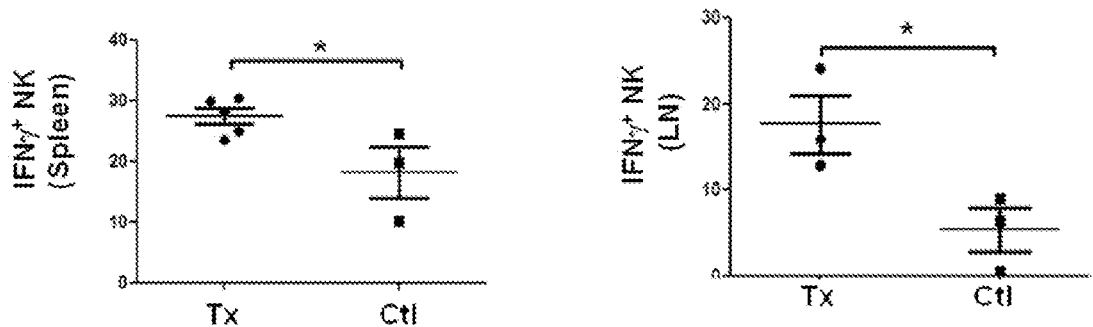

Tumor-derived sMIC perturbs NK peripheral homeostasis to deplete peripheral NK cells (JCI revision). With the antibody to neutralize circulating sMIC, peripheral NK cell homeostasis was significantly restored as measured by NK cell frequency in the spleen and draining lymph nodes (FIG. 11A). Moreover, continues BrdU pulsing (5-day in the drinking water, 5 mg/ml) revealed that the rate of NK cell renewal was remarkably enhanced with the antibody treatment (FIG. 11B). Moreover, antibody treatment markedly increased NK cell IFNγ production in response to restimulation (FIG. 11C). When congenic splenocytes were transferred to these animals, similar effects on congenic transferred splenic NK cells were seen.

Antibody Treatment Breaks CD8 T Cell Tolerance

Figure 12A:
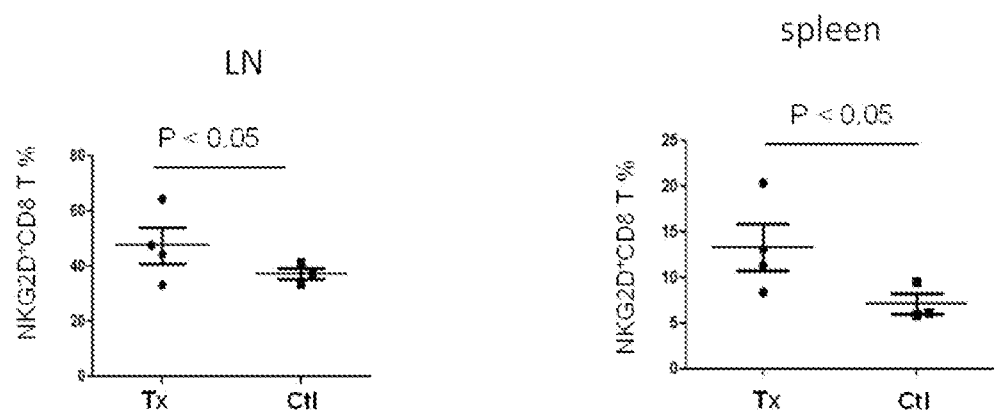
FIGS. 12A-12B demonstrate that antibody treatment enhanced CD8 T cell activation and function.
Figure 12B:
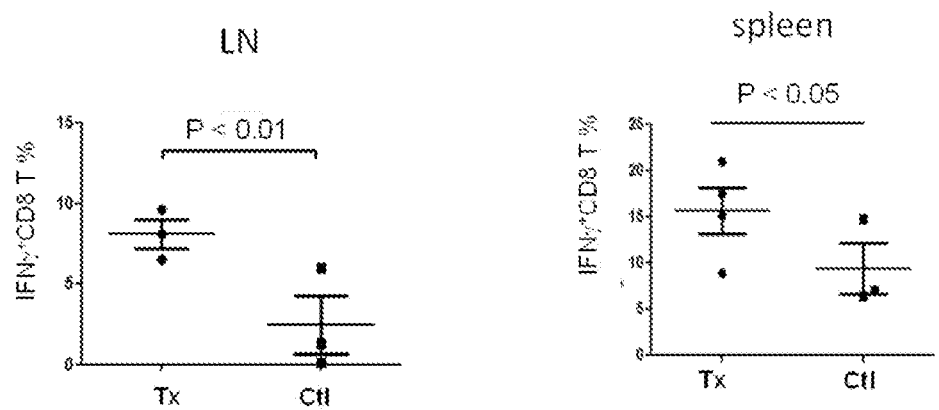

CD8 T cell tolerization has been described as a common mechanism of immune dysfunction in cancer patients and well documented in the prostate cancer mouse model TRAMP as well. With the antibody treatment to neutralize serum sMIC in TRAMP/MIC mice, a significant activation of CD8 T cells in the spleen and LN was seen as examined by NKG2D expression expression (FIG. 12A). As being described, in mouse NKG2D is only expressed by activated CD8 T cells. Moreover, a significant greater response to restimulation as measured by IFNγ production was seen in CD8 T cells from animals that received antibody treatment (FIG. 12B). Further, antibody treatment significant increased the pool of central memory CD8 T cells in both LN and spleen (FIG. 12C).

Antibody Treatment Polarizes CD4 T Helper Cells to Th1 and Th17 Types

Figure 13A:
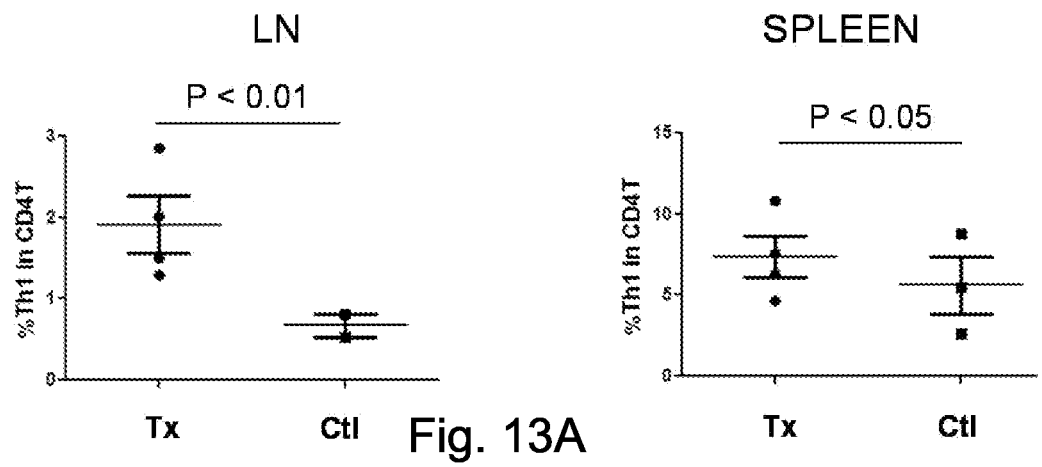
FIGS. 13A-13C demonstrate that antibody treatment polarizes CD4 helper T cell to Th1 and Th17 and enhances accumulation of central memory CD4 T cells.
Figure 13B:
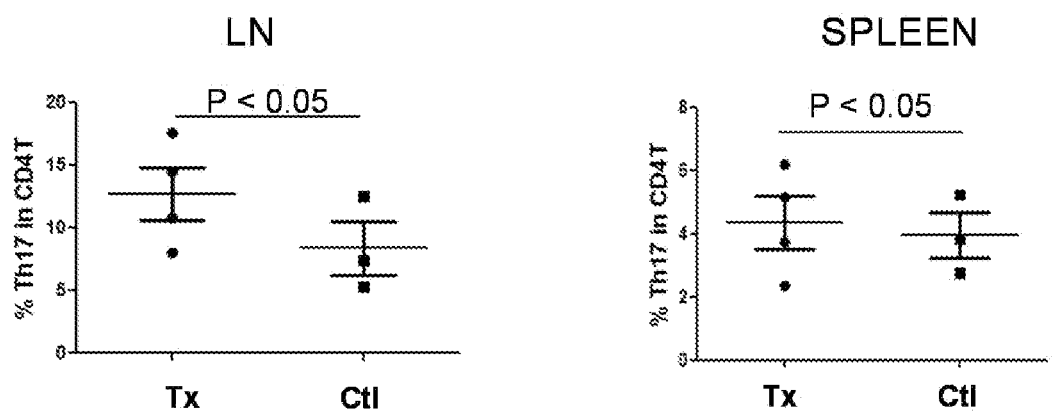
Figure 13C:
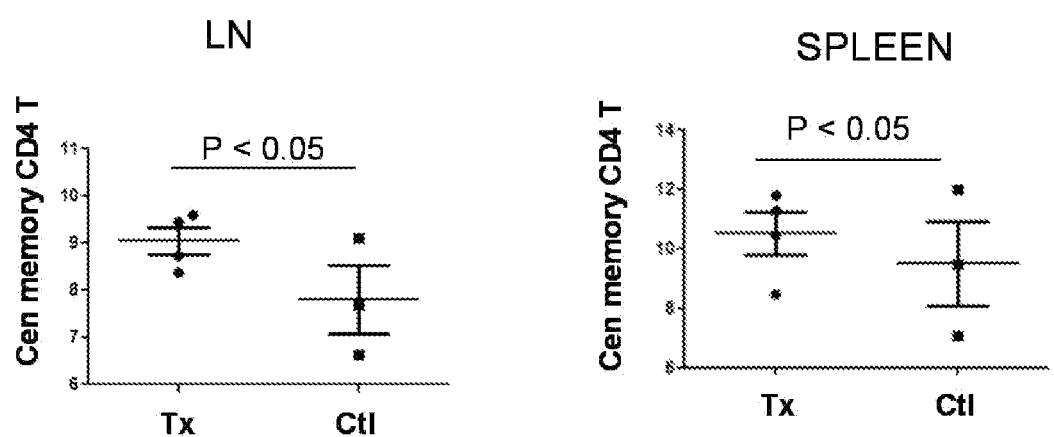
Figure 14A:
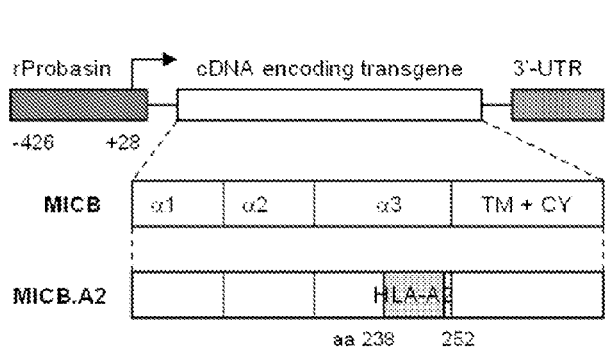
FIGS. 14A-14C demonstrate that prostate-restricted expression of NKG2D ligands does not alter prostate physiology or systemic immunity.
Figure 14B:
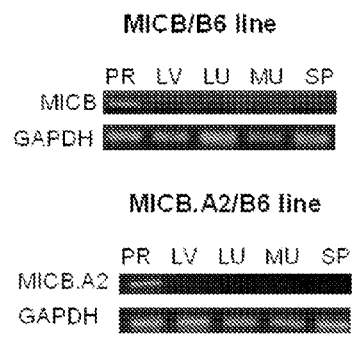
Figure 14C:
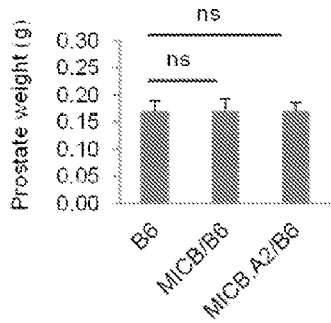
Figure 15A:
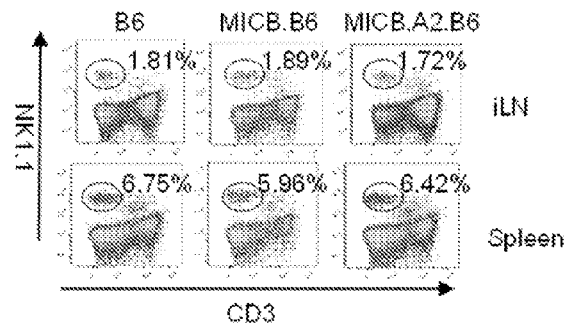
FIGS. 15A-15D demonstrate that prostate-specific expression of MIC has no impact on the number of systemic NK cells and CD8 T cells.
Figure 15B:
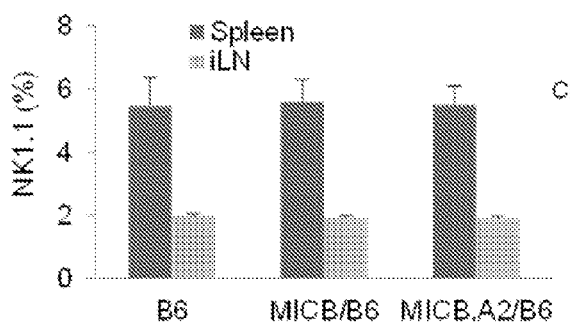
Figure 15C:
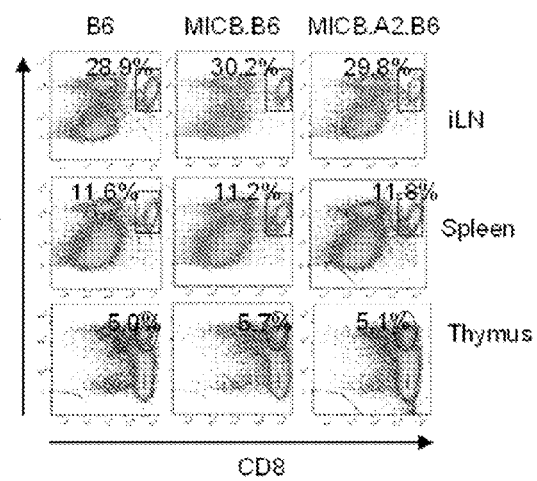
Figure 15D:
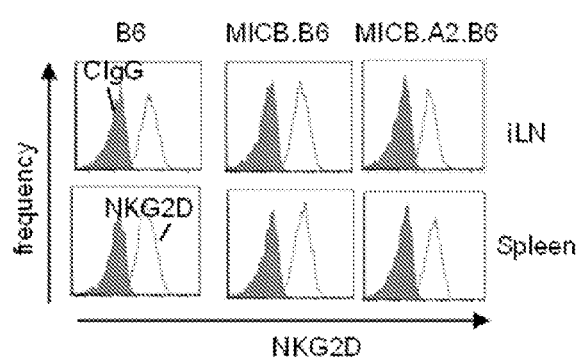

Antibody neutralizing sMIC did not have a significant effect on total CD4 T cell pool in the spleen or LN (data not shown). However, with the neutralization of sMIC, CD4 T cell were primed to polarization into Th1 and Th17 helper cells as assayed by staining with transcriptional factor T-bet and RORγt (FIGS. 13A and 13B). Similar effects on CD4 T cells were seen with adoptively transferred congenic splenocytes. Moreover, central memory CD4 T cell pool in the LN was significantly increased with the antibody treatment (FIG. 13C).

Discussion

It is demonstrated herein that neutralizing serum sMIC with a monoclonal antibody (e.g., P2B10G5) can effectively induce regression of advanced prostate carcinoma and inhibit metastasis with a clinically relevant animal model. It is further demonstrated that the tumor suppression and clearance is through re-establishment of NK cell homeostasis, polarization of CD4 T helper cells to Th1 and Th17, and reactivation of CD8 T cells. Further, it is demonstrated herein that adoptively transferred NK cells cannot be sustained in tumor host, unless sMIC was depleted. Importantly, reported herein is a novel class of monoclonal antibodies that can treat many advanced solid tumors, including but not limited to advanced prostate cancer.

Methods

Animals and Antibody administration. Breeding of TRAMP/MICB has been previously described (JCI revision). When mice reached 26-28 weeks of age, cohorts of animals were i.p. injected with mAb P2B10G5 or isotype control IgG at the dose of 30 mg/KG body weight twice weekly. All animals were treated for 6 weeks before euthanization which is defined as the study end point. Mice were fed with 0.8 mg/mL BrdU (Sigma) in drinking water for 5 days before study end point. All animals were housed in specific pathogen-free facilities. All experimental procedures were approved by the Institutional Animal Care and Use Committee.

Congenic cells transfer. For adaptive transfer of congenic spleen cells, C57BL/6 (CD45.1/Ly5.2) mice were purchased from Charles River Laboratories (Frederick Cancer Research Center, Frederick, Md.). Upon euthanizaiton, whole nucleated splenocytes were obtained after removal of red blood cells with red blood cell lysing buffer (Sigma) and labeled with V450 cell proliferation dye (eBioscience) according to manufacturer's instruction. V450-Labeled splenocytes were suspended in 1×PBS and i.v. injected into recipient at the dose of $2 \times 10^7$/mouse. The adoptive transfer was done 5 days before end point and tissue collection.

Tissue Collection. Peripheral blood mononuclear cells were collected using a tail bleed procedure the day before end point day. Single cell suspensions of PBMC were processed for FACS staining using 1×PBS based 1% Dextran T500 and red blood cell lysing buffer. Serum was collected for measurement of cytokine and sMIC. Spleens, lymph nodes, prostates, lungs, femur and tibia were collected. Single cell suspension of lymph nodes, spleen, and bone marrow were prepared as described elsewhere for phnotyping and functional analyses. Prostates, lungs, Kidney, and pancreas were collected, fixed in 10% NBF (neutral fixation buffer), paraffin embedded, and sectioned for histology analyses.

Flowcytometry. For surface phenotyping, the following antibody were used: Fluorochrome-conjugated or biotinylated monoclonal antibodies specific to mouse,CD3e (clone 145-2c11), CD8a (clone 53-6.7), CD4(clone GK1.5), NK1.1(clone PK136), NKG2D (clone CX5), CD27(clone LG.7F9), CD1 1b (clone M1/70), CD45.1 (clone A20), CD44 (clone IM7), FoxP3(clone FJK-16s), anti-BrdU (cloneBu20a), Ki67(clone SolA15), T-bet (clone eBio4B10), RORγt (clone B2D), CD62L (MEL-14), PD-1 (clone J43), (KLRG1) (clone 2F1) and the corresponding isotype control antibodies are products of eBioscience. CD69 (H1.2F3), INF-γ(XMG1.2), CD25(clone PC61) from BD. For ex vivo restimulation, freshly isolated splenocytes and single cell suspension from the LN were maintained in culture with SOng/mL PMA and 500 ng/mL Ionomycin in complete RPMI 1640 medium with (Hyclone) 10% FBS (Atlanta Biologicals, GA), penicillin/streptomycin (Hyclone) and 50 uM 2ME (Millipore) for 4-6 h and then analyzed by intracellular staining with antibodies specific to IFNg, IL-4, IL-17, and IL-10. BrdU staining was performed using a methanol fixation and acid treatment protocol as described. Multi-parameter Flow cytometry analyses were performed on an LSR II™ (BD) and analyzed with FlowJo™ software (Tree Star).

IHC staining and data collecting. The IHC staining protocol has been previously described. The following antigen-specific antibodies were used: anti-SV40T (Santa Cluz, clone v300), anti-Arginase I (Santa Cluz, clone H52), F4/80 (Biolegend, clone BM8), anti-Ki67 (Neomarker, clone SP6), MAC-2 (ATCC hybridoma), anti-Cleaved Caspase-3(cell signaling, clone 5A1E). All tissues were counter stained with Hemotoxyline (Thermo Scientific).

Cytokines panel reading. Serum cytokine concentrations were measured by Eve Technologies Corporation (Canada), using the mouse 32-plex discovery assay.

ELISA assay. Serum soluble MICB concentrations were tested using a MICB ELISA kit from R&D according to manufacturer's manual. Triplicates for each sample were assayed. OD450 referenced by OD570 value was read and compared between the treated group and the control group.

Statistical analysis. All results are expressed as the mean±SEM. Mouse and sample group sizes were n>5, unless otherwise indicated. Data were analyzed using unpaired test, and differences were determined significant at $P<0.05$.

References

1. Long, E. O. 2002. Versatile signaling through NKG2D. Nat Immunol 3:1119-1120.
2. Raulet, D. H. 2003. Roles of the NKG2D immunoreceptor and its ligands. Nat Rev Immunol 3:781-790.
3. Bauer, S., Groh, V., Wu, J., Steinle, A., Phillips, J. H., Lanier, L. L., and Spies, T. 1999. Activation of NK cells and T cells by NKG2D, a receptor for stress-inducible MICA. Science 285:727-729.
4. Groh, V., Rhinehart, R., Randolph-Habecker, J., Topp, M. S., Riddell, S. R., and Spies, T. 2001. Costimulation of CD8alphabeta T cells by NKG2D via engagement by MIC induced on virus-infected cells. Nat Immunol 2:255-260.
5. Wu, J., Groh, V., and Spies, T. 2002. T cell antigen receptor engagement and specificity in the recognition of stress-inducible MHC class I-related chains by human epithelial gamma delta T cells. Journal of immunology 169:1236-1240.

6. Diefenbach, A., Jensen, E. R., Jamieson, A. M., and Raulet, D. H. 2001. Rael and H60 ligands of the NKG2D receptor stimulate tumour immunity. Nature 413:165-171.
7. Cerwenka, A., Baron, J. L., and Lanier, L. L. 2001. Ectopic expression of retinoic acid early inducible-1 gene (RAE-1) permits natural killer cell-mediated rejection of a MHC class I-bearing tumor in vivo. Proc Natl Acad Sci USA 98:11521-11526.
8. Smyth, M. J., Swann, J., Cretney, E., Zerafa, N., Yokoyama, W. M., and Hayakawa, Y. 2005. NKG2D function protects the host from tumor initiation. J Exp Med 202:583-588.
9. Guerra, N., Tan, Y. X., Joncker, N. T., Choy, A., Gallardo, F., Xiong, N., Knoblaugh, S., Cado, D., Greenberg, N. M., and Raulet, D. H. 2008. NKG2D-deficient mice are defective in tumor surveillance in models of spontaneous malignancy. Immunity 28:571-580.
10. Nausch, N., and Cerwenka, A. 2008. NKG2D ligands in tumor immunity. Oncogene 27:5944-5958.
11. Groh, V., Rhinehart, R., Secrist, H., Bauer, S., Grabstein, K. H., and Spies, T. 1999. Broad tumor-associated expression and recognition by tumor-derived gamma delta T cells of MICA and MICB. Proc Natl Acad Sci USA 96:6879-6884.
12. Coudert, J. D., Zimmer, J., Tomasello, E., Cebecauer, M., Colonna, M., Vivier, E., and Held, W. 2005. Altered NKG2D function in NK cells induced by chronic exposure to NKG2D ligand-expressing tumor cells. Blood 106:1711-1717.
13. Holdenrieder, S., Stieber, P., Peterfi, A., Nagel, D., Steinle, A., and Salih, H. R. 2006. Soluble MICB in malignant diseases: analysis of diagnostic significance and correlation with soluble MICA. Cancer Immunol Immunother 55:1584-1589.
14. Holdenrieder, S., Stieber, P., Peterfi, A., Nagel, D., Steinle, A., and Salih, H. R. 2006. Soluble MICA in malignant diseases. Int J Cancer 118:684-687.
15. Oppenheim, D. E., Roberts, S. J., Clarke, S. L., Filler, R., Lewis, J. M., Tigelaar, R. E., Girardi, M., and Hayday, A. C. 2005. Sustained localized expression of ligand for the activating NKG2D receptor impairs natural cytotoxicity in vivo and reduces tumor immunosurveillance. Nat Immunol 6:928-937.
16. Raffaghello, L., Prigione, I., Airoldi, I., Camoriano, M., Levreri, I., Gambini, C., Pende, D., Steinle, A., Ferrone, S., and Pistoia, V. 2004. Downregulation and/or release of NKG2D ligands as immune evasion strategy of human neuroblastoma. Neoplasia 6:558-568.
17. Salih, H. R., Antropius, H., Gieseke, F., Lutz, S. Z., Kanz, L., Rammensee, H. G., and Steinle, A. 2003. Functional expression and release of ligands for the activating immunoreceptor NKG2D in leukemia. Blood 102:1389-1396.
18. Salih, H. R., Goehlsdorf, D., and Steinle, A. 2006. Release of MICB molecules by tumor cells: mechanism and soluble MICB in sera of cancer patients. Human immunology 67:188-195.
19. Wiemann, K., Mittrucker, H. W., Feger, U., Welte, S. A., Yokoyama, W. M., Spies, T., Rammensee, H. G., and Steinle, A. 2005. Systemic NKG2D down-regulation impairs NK and CD8 T cell responses in vivo. J Immunol 175:720-729.
20. McGilvray, R. W., Eagle, R. A., Rolland, P., Jafferji, I., Trowsdale, J., and Durrant, L. G. 2010. ULBP2 and RAET1E NKG2D ligands are independent predictors of poor prognosis in ovarian cancer patients. International journal of cancer. Journal international du cancer 127: 1412-1420.
21. Madjd, Z., Spendlove, I., Moss, R., Bevin, S., Pinder, S. E., Watson, N. F., Ellis, I., and Durrant, L. G. 2007. Upregulation of MICA on high-grade invasive operable breast carcinoma. Cancer immunity 7:17.
22. Watson, N. F., Spendlove, I., Madjd, Z., McGilvray, R., Green, A. R., Ellis, I. O., Scholefield, J. H., and Durrant, L. G. 2006. Expression of the stress-related MHC class I chain-related protein MICA is an indicator of good prognosis in colorectal cancer patients. International journal of cancer. Journal international du cancer 118:1445-1452.
23. McGilvray, R. W., Eagle, R. A., Watson, N. F., Al-Attar, A., Ball, G., Jafferji, I., Trowsdale, J., and Durrant, L. G. 2009. NKG2D ligand expression in human colorectal cancer reveals associations with prognosis and evidence for immunoediting. Clinical cancer research: an official journal of the American Association for Cancer Research 15:6993-7002.
24. de Kruijf, E. M., Sajet, A., van Nes, J. G., Putter, H., Smit, V. T., Eagle, R. A., Jafferji, I., Trowsdale, J., Liefers, G. J., van de Velde, C. J., et al. 2012. NKG2D ligand tumor expression and association with clinical outcome in early breast cancer patients: an observational study. BMC cancer 12:24.
25. Groh, V., Wu, J., Yee, C., and Spies, T. 2002. Tumour-derived soluble MIC ligands impair expression of NKG2D and T-cell activation. Nature 419:734-738.
26. Jinushi, M., Vanneman, M., Munshi, N.C., Tai, Y. T., Prabhala, R. H., Ritz, J., Neuberg, D., Anderson, K. C., Carrasco, D. R., and Dranoff, G. 2008. MHC class I chain-related protein A antibodies and shedding are associated with the progression of multiple myeloma. Proc Natl Acad Sci USA 105:1285-1290.
27. Tamaki, S., Kawakami, M., Ishitani, A., Kawashima, W., Kasuda, S., Yamanaka, Y., Shimomura, H., Imai, Y., Nakagawa, Y., Hatake, K., et al. 2010. Soluble MICB serum levels correlate with disease stage and survival rate in patients with oral squamous cell carcinoma. Anticancer Res 30:4097-4101.
28. Wu, J. D., Higgins, L. M., Steinle, A., Cosman, D., Haugk, K., and Plymate, S. R. 2004. Prevalent expression of the immunostimulatory MHC class I chain-related molecule is counteracted by shedding in prostate cancer. J Clin Invest 114:560-568.
29. Rebmann, V., Schutt, P., Brandhorst, D., Opalka, B., Moritz, T., Nowrousian, M. R., and Grosse-Wilde, H. 2007. Soluble MICA as an independent prognostic factor for the overall survival and progression-free survival of multiple myeloma patients. Clin Immunol 123:114-120.
30. Hayakawa, Y. 2012. Targeting NKG2D in tumor surveillance. Expert opinion on therapeutic targets 16:587-599.
31. Champsaur, M., and Lanier, L. L. 2010. Effect of NKG2D ligand expression on host immune responses. Immunol Rev 235:267-285.
32. Friese, M. A., Platten, M., Lutz, S. Z., Naumann, U., Aulwurm, S., Bischof, F., Buhring, H. J., Dichgans, J., Rammensee, H. G., Steinle, A., et al. 2003. MICA/NKG2D-mediated immunogene therapy of experimental gliomas. Cancer Res 63:8996-9006.
33. Wu, J. D., Atteridge, C. L., Wang, X., Seya, T., and Plymate, S. R. 2009. Obstructing shedding of the immunostimulatory MHC class I chain-related gene B prevents tumor formation. Clin Cancer Res 15:632-640.

34. Diefenbach, A., Jamieson, A. M., Liu, S. D., Shastri, N., and Raulet, D. H. 2000. Ligands for the murine NKG2D receptor: expression by tumor cells and activation of NK cells and macrophages. Nature immunology 1:119-126.
35. Greenberg, N. M., DeMayo, F., Finegold, M. J., Medina, D., Tilley, W. D., Aspinall, J. O., Cunha, G. R., Donjacour, A. A., Matusik, R. J., and Rosen, J. M. 1995. Prostate cancer in a transgenic mouse. Proc Natl Acad Sci USA 92:3439-3443.
36. Wang, X., Lundgren, A. D., Singh, P., Goodlett, D. R., Plymate, S. R., and Wu, J. D. 2009. An six-amino acid motif in the alpha3 domain of MICA is the cancer therapeutic target to inhibit shedding. Biochemical and biophysical research communications 387:476-481.
37. Gingrich, J. R., Barrios, R. J., Foster, B. A., and Greenberg, N. M. 1999. Pathologic progression of autochthonous prostate cancer in the TRAMP model. Prostate Cancer Prostatic Dis 2:70-75.
38. Kaplan-Lefko, P. J., Chen, T. M., Ittmann, M. M., Barrios, R. J., Ayala, G. E., Huss, W. J., Maddison, L. A., Foster, B. A., and Greenberg, N. M. 2003. Pathobiology of autochthonous prostate cancer in a pre-clinical transgenic mouse model. The Prostate 55:219-237.
39. Anderson, M. J., Shafer-Weaver, K., Greenberg, N. M., and Hurwitz, A. A. 2007. Tolerization of tumor-specific T cells despite efficient initial priming in a primary murine model of prostate cancer. J Immunol 178:1268-1276.
40. Bai, A., Higham, E., Eisen, H. N., Wittrup, K. D., and Chen, J. 2008. Rapid tolerization of virus-activated tumor-specific CD8+ T cells in prostate tumors of TRAMP mice. Proc Natl Acad Sci USA 105:13003-13008.
41. Ren, C., Kumar, S., Chanda, D., Kallman, L., Chen, J., Mountz, J. D., and Ponnazhagan, S. 2008. Cancer gene therapy using mesenchymal stem cells expressing interferon-beta in a mouse prostate cancer lung metastasis model. Gene therapy 15:1446-1453.
42. Varghese, S., Rabkin, S. D., Liu, R., Nielsen, P. G., Ipe, T., and Martuza, R. L. 2006 Enhanced therapeutic efficacy of IL-12, but not GM-CSF, expressing oncolytic herpes simplex virus for transgenic mouse derived prostate cancers. Cancer gene therapy 13:253-265.
43. Holdenrieder, S., Eichhorn, P., Beuers, U., Samtleben, W., Stieber, P., Nagel, D., Peterfi, A., Steinle, A., and Salih, H. R. 2007. Soluble NKG2D ligands in hepatic autoimmune diseases and in benign diseases involved in marker metabolism. Anticancer research 27:2041-2045.
44. Doubrovina, E. S., Doubrovin, M. M., Vider, E., Sisson, R. B., O'Reilly, R. J., Dupont, B., and Vyas, Y. M. 2003. Evasion from NK cell immunity by MHC class I chain-related molecules expressing colon adenocarcinoma. J Immunol 171:6891-6899.
45. Suzuki, Y., Sutoh, M., Hatakeyama, S., Mori, K., Yamamoto, H., Koie, T., Saitoh, H., Yamaya, K., Funyu, T., Habuchi, T., et al. 2012. MUC1 carrying core 2 O-glycans functions as a molecular shield against NK cell attack, promoting bladder tumor metastasis. International journal of oncology 40:1831-1838.
46. Galon, J., Costes, A., Sanchez-Cabo, F., Kirilovsky, A., Mlecnik, B., Lagorce-Pages, C., Tosolini, M., Camus, M., Berger, A., Wind, P., et al. 2006. Type, density, and location of immune cells within human colorectal tumors predict clinical outcome. Science 313:1960-1964.
47. Gulubova, M., Manolova, I., Kyurkchiev, D., Julianov, A., and Altunkova, I. 2009. Decrease in intrahepatic CD56+ lymphocytes in gastric and colorectal cancer patients with liver metastases. APMIS: acta pathologica, microbiologica, et immunologica Scandinavica 117:870-879.
48. Vivier, E., Ugolini, S., Blaise, D., Chabannon, C., and Brossay, L. 2012. Targeting natural killer cells and natural killer T cells in cancer. Nature reviews. Immunology 12:239-252.
49. Salagianni, M., Baxevanis, C. N., Papamichail, M., and Perez, S. A. 2012. New insights into the role of NK cells in cancer immunotherapy. Oncoimmunology 1:205-207.
50. Liu, G., Atteridge, C. L., Wang, X., Lundgren, A. D., and Wu, J. D. 2010. The membrane type matrix metalloproteinase MMP14 mediates constitutive shedding of MHC class I chain-related molecule A independent of A disintegrin and metalloproteinases. Journal of immunology 184:3346-3350.
51. Waldhauer, I., Goehlsdorf, D., Gieseke, F., Weinschenk, T., Wittenbrink, M., Ludwig, A., Stevanovic, S., Rammensee, H. G., and Steinle, A. 2008. Tumor-associated MICA is shed by ADAM proteases. Cancer research 68:6368-6376.
52. Perentes, J. Y., Kirkpatrick, N. D., Nagano, S., Smith, E. Y., Shaver, C. M., Sgroi, D., Garkavtsev, I., Munn, L. L., Jain, R. K., and Boucher, Y. 2011. Cancer cell-associated MT1-MMP promotes blood vessel invasion and distant metastasis in triple-negative mammary tumors. Cancer research 71:4527-4538.
53. Wu, J. D., Lin, D. W., Page, S. T., Lundgren, A. D., True, L. D., and Plymate, S. R. 2009. Oxidative DNA damage in the prostate may predispose men to a higher risk of prostate cancer. Translational oncology 2:39-45.

TABLE 1

Pathological comparison of TRAMP and TRAMP/MICB mice at 24 weeks.

| Pathology | TRAMP | TRAMP/MICB |
| --- | --- | --- |
| Normal/early PIN | 0/13 | 0/12 |
| PIN | 0/13 | 0/12 |
| Tumor | 13/13 | 12/12 |
| Palpable Tumors | 0/13 | 4/12 |
| WD | 12/13 (91.7%) | 6/12 (50%) |
| PD | 0/13 | 4/12 (33%) |
| [a] MD | 1/13 | 2/12 (17%) |
| [b] Phylloides | 2/13 (12.5%) | 0/13 |
| [c] Metastasis | 0/13 | 4/12 (33%) |
| [d] Prostate weight | 0.30 ± 0.04 | 0.82 ± 0.29 |
| Median Survival (wks) | 43.5 | 34 |

[a] MD lesions are in transition to PD lesions.
[b] Phylloides, a staghorn type oflesion. Among the two, one is a MD lesion and the other is a WD.
[c] Among the 4 animals with PD tumors, three had metastasis in lung and lymph nodes, one had only lung metastasis.
[d] Expressed as Mean ± SEM (g).

Example 3

Soluble NKG2D Ligand is an Effective Immunotherapeutic Target for Advanced Cancer Elevated tumor shedding of soluble NKG2D ligand, MHC I chain related molecule (sMIC), is associated with advanced cancer stage and metastasis in many types of solid tumors. High serum levels of sMIC not only down-regulate NKG2D expression on natural killer (NK) cells and effector T cells but also perturb NK cell peripheral maintenance. Whether sMIC is an effective therapeutic target in MIC cancer patients is unknown. Using a "humanized" clinically relevant spontaneous prostate carcinoma TRAMP/MIC bi-transgenic mouse model, it is demonstrated herein that therapy with a monoclonal antibody specific to sMIC significantly improved the survival of animals by induction of rapid regression and inhibition of primary tumors and metastasis. The therapy effected through the mechanism of reducing serum sMIC, restoring NK cell homeostatic renewal and function, priming and polarizing CD4 T cells to Th1 type, and potentiating CD8 T cell function. No systemic cytotoxicity was present. Notably, depletion of NK cells during therapy mitigated the therapeutic effect and failed to potentiate the effector function of both CD4 and CD8 T cells. This data indicates that sMIC is an effective therapeutic target for MIC advanced cancer and that co-targeting sMIC significantly potentiates adaptive-based immunotherapy for cancer.

MIC is an induced molecule expressed on human cancers and rarely present on normal tissues. In patients with metastatic cancer, serum levels of sMIC were consistently elevated. Rodents do not express MIC homolog and thus tumor shedding of sMIC is a human-specific phenomenon. To address the impact of tumor shedding of sMIC in cancer progression, a bi-transgenic TRAMP/MIC(B) mouse that express human MIC in the prostate epithelial cells of TRAMP mice directed by the prostate-specific promoter was developed. The TRAMP/MIC mouse closely recapitulates many immunological and pathological features of human cancer patients. Closely resembling men with prostate cancer, TRAMP/MIC mice with high serums levels of sMIC exhibited impaired NK cell peripheral homeostasis and high incidence of poorly-differentiated (PD) prostate carcinoma and metastasis. Typically by 24-week of age, more than 40% of the TRAMP/MIC mice develop PD carcinoma and metastasis. To evaluate whether sMIC is an effective therapeutic target, cohorts of 27 to 28-week old TRAMP/MIC mice were treated with a sMIC-specific monoclonal antibody B10G5 or control mouse IgG (cIgG, placebo) twice weekly via i.p. at the dose of 3.4 mg/kg body weight (FIG. 21A). After 8 weeks of treatment, all mice in the antibody treated group in general are healthy whereas all the mice in the control group showed severe symptoms of illness. Mice received B10G5 therapy had significantly smaller prostate in compare to those in the placebo group (FIGS. 21B-21C). No metastasis was present in the distant organ in the B10G5 treated mice. Conversely, over 60% of mice in the placebo group developed metastasis in distant organs (FIG. 21D). Systemic response to B10G5 treatment was determined. In response to B10G5 treatment, serum levels of sMIC were significantly reduced (FIG. 21E). Presumably as result of reactivation of host anti-tumor response with B10G5 treatment, a serum cytokine "storm" was presented with marked elevation of major anti-tumor cytokines, e.g. IFNγ, IL-12 (FIG. 21F). However, significant systemic cytotoxicity in response to B10G5 therapy was not observed, as no significant change in animal body weight, organ inflammation, or total serum IgG level was detected (FIG. 21G).

The effect of B10G5 therapy on primary tumors was examined Histologically, animals received B10G5 therapy exhibited organ-defined well-differentiated prostate carcinoma, whereas animals received placebo exhibited high frequency of progressed PD prostate carcinoma (data not shown). B10G5 therapy significantly inhibited the proliferation of prostate epithelial cells and induced apoptosis of as shown by Ki-67 and cleaved caspase-3 immunohistochemistry staining respectively (data not shown). In prostate cancer, although neuroendocrine cancer cells are rarely found in early stage prostate tumors, 40-100% of castrate-resistant prostate cancer (CRPC) demonstrate evidence of neuroendocrine trans-differentiation (15), a process whereby adenocarcinoma cells acquire markers for neuroendocrine cells, e.g. synaptophysin and chromogranin A. The neuroendocrine phenotype is intrinsically resistant to hormone-ablation therapies as these cells lose hormone receptor expression and therefore is considered to confer a poor prognosis (15-17). In the prostate of most TRAMP/MIC mice receiving placebo therapy or no therapy, a distinct population of disseminated synaptophysin-positive neuroendocrine cells was infiltrated in the stroma. B10G5 therapy remarkably eliminated synaptophysin-positive cells in the prostate (data not shown).

Systemic sMIC-targeting significantly primed prostate tumor microenvironment to be highly immune reactive represented by marked increase of tumor cytotoxic NK and CD8 T cell infiltration and elimination of immune suppressive regulatory T cells (Treg) and tumor-associated type 2 macrophages (M2) in the prostate. In most advanced malignancies, NK cells were rarely found in tumor infiltrates. In early stage of most primary solid tumors, NK cell infiltrates correlated with better clinical outcomes (Desbois M and Chaput N, 2012), suggesting an important role of NK cell in controlling cancer progression. We have recently shown that in TRAMP/MIC mice, NK infiltration in progressive prostate cancer is rarely found due to tumor shedding of sMIC. In response to B10G5 therapy, the primary prostate tumors were abundantly infiltrated with NK cells (data not shown). Anergy or tolerization of CD8 T cells in tumor microenvironment is well-described in TRAMP mice, also most tumor types Intriguingly, in response to B10G5 therapy, the prostate was inflamed with cytotoxic CD8 T cells (data not shown), suggesting a revived homing or proliferation of tumor-reactive cytotoxic T cells. It is well accepted that presence of immune suppressive $T_{regs}$ or Arginase I-producing M2 macrophages in the tumor microenvironment confers cancer poor prognosis. With B10G5 therapy, both populations were significantly diminished (data not shown).

Elevated serum sMIC was shown to impair peripheral NK function in cancer patients at large by down regulating NKG2D expression. With TRAMP/MIC mice, it was demonstrated that high levels of sMIC perturb NK cell homeostatic maintenance and are correlated with depletion of NK cell in cancer patients. This is thought to be the major mechanism by which sMIC confers immune suppression and facilitates cancer progression to metastasis. B10G5 therapy markedly restored peripheral NK cell pool in the periphery (FIG. 22A) and the ability of NK cell to renewal in the spleen and bone marrow as shown by BrdU uptake after a continuous BrdU pulsing (5-day in the drinking water, 0.8 mg/ml) (FIG. 22B). Moreover, B10G5 therapy markedly increased NK cell function as represented by IFNγ production in response to PMA and ionomycin stimulation (FIG. 22C). When congenic splenocytes were transferred to these animals, similar effects were demonstrated (data not shown). Together these data indicate that eliminating serum sMIC heightens NK cell homeostatic maintenance and function in $MIC^+$ cancer host.

Neutralizing serum sMIC with B10G5 profoundly potentiate both CD8 and CD4 anti-tumor responses, which to a great degree depend on the sustainability of functional NK cells. T cells are often tolerized or anergy in cancer patients and tumor-bearing mouse models. In TRAMP mouse, anergy of both CD8 and CD4 T cells has been well-documented. B10G5 therapy in TRAMP/MIC mice significant breaks CD8 T cell tolerance as shown by the increase in $NKG2D^+$ CD8 T cell population in the spleen, LN, and tumor infiltrates and high magnitude of IFNγ production in response to PMA and ionomycin stimulation (FIGS. 22D-22E). B10G5 therapy did not significantly impact the pool of peripheral CD4 T cells in the spleen or LN (data not shown); however, CD4 T cell were primed to polarization into Th1 and Th17 helper cells as assessed by significant increases in T-bet$^+$ and RORγt$^+$ population among CD4 T cells and cytokine IFNr and IL-17 in response to stimulation ex vivo (FIG. 22F).

Furthermore, in response to B10G5 therapy, populations of CD44$^{hi}$ memory CD8 T and CD4 T cell were both significant enhanced (FIG. 22G). It is intriguing that the anti-tumor effect of B10G5 and the potentiation of CD4 and CD8 T cells were mitigated when NK cells were depleted during therapy (FIG. 23A-23C).

Discussion

It is demonstrated herein, with a clinically relevant animal model for the first time, that antibody targeting sMIC effectively induces regression of primary tumor and inhibited metastasis in MIC$^+$ malignancy. It is further demonstrated that the mechanisms of tumor suppression and metastatic clearance is conferred through restoring NK cell homeostatic maintenance and function, potentiating cytotoxic CD8 T cells, and priming polarization of CD4 T helper cells to Th1 and Th17. Moreover, it is also indicated herein that targeting sMIC or other soluble NKG2D ligands can augment adoptive NK cell therapy for MIC$^+$ malignancies or, in a broad sense, NKG2D-ligand$^+$ malignancies. Furthermore, it is demonstrated herein that functional NK cells have a key role in potentiating adaptive immune responses against MIC$^+$ tumors. Together, provided herein is the in vivo proof-of-evidence that sMIC is an effective target for cancer therapy, and also the demonstration of a novel concept that co-targeting sMIC can enhance current clinical practice of cancer immunotherapy, whether NK or adaptive-based cancer immunotherapy, for MIC$^+$ tumors.

Methods Summary

Animals and antibody therapy. Breeding of TRAMP/MICB has been described. When mice reached 27-28 weeks of age, cohorts of animals were i.p. injected with B10G5 or isotype control IgG at the dose of 4 mg/Kg body weight twice weekly. Generation and Characterization of the B10G5 antibody were described previously. All animals were treated for eight weeks before euthanization which was designated as the study end point. Mice received daily refreshed drinking water containing 0.8 mg/mL BrdU for five consecutive days before study end point. All animals were housed in specific pathogen-free facilities. All experimental procedures were approved by the Institutional Animal Care and Use Committee. The study was repeated three times.

Congenic cells transfer. Splenocytes were isolated from congenic CD45.1$^+$ C57BL/6 mice (Charles River Laboratories, Frederick Cancer Research Center, Frederick, Md.) and labeled with V$_{450}$ cell-trace dye according to manufacteuer's protocol (eBioscience). V$_{450}$-labeled splenocytes were resuspended in PBS and injected via tail veil into recipient TRAMP/MICB mice (CD45.2$^+$) at the dose of 2×10$^7$/mouse five days before end point.

NK depletion. Mice were injected with NK1.1-specific antibody PK136 (BioXcell, Labnon, N.H.) at the dose of 200 μg/mouse one day before B10G5 antibody therapy and thereafter twice weekly at the dose of 100 μg/mouse till study end point. Three wild type C57BL/6 mice also received the same dose of PK136 antibody to monitor the efficacy of NK depletion. Efficiency of NK depletion was confirmed by flow cytometry analyses of NK cell population with an antibody to NK receptor NKp46 in the peripheral blood of experimental mice and control wild type C57BL/6 mice. Greater than 99% NK depletion was achieved one week after PK136 administration (data not shown).

Tissue collection. Blood was collected via tail bleeding during therapy and via cardiac puncture after euthanization. Spleens and draining lymph nodes (dLN) were collected for immunological analyses. Prostate, lung, liver, kidney, pancreas, and intestines were collected, fixed in 10% neutral fixation buffer followed by paraffin embedment or directly embedded in OCT, for pathological and histological analyses. In some experiments, partial of prostate tumors was digested with collegenase for analyses of tumor infiltrated lymphocytes.

Flow cytometry. Single cell suspension from splenocytes, dLN, or tumor infiltrates was prepared as described. Combination of the following antibody were used for cell surface or intracellular staining to define populations of NK, CD8, and subsets of CD4 T cells: CD3e (clone 145-2c11), CD8a (clone 53-6.7), CD4 (clone GK1.5), NK1.1 (clone PK136), NKp46, NKG2D (clone CX5), CD45.1 (clone A20), CD44 (clone IM7), CD62L (MEL-14), FoxP3 (clone FJK-16s, T-bet (clone eBio4B10), and RORγt (clone B2D). For ex vivo restimulation, single cell suspension of freshly isolated splenocytes or LN were cultured in complete RPMI 1640 medium containing 50 ng/mL PMA and 500 ng/mL Ionomycin for 4-6 h and analyzed by intracellular staining with antibodies specific to IFNγ (XMG1.2), IL-4, IL-17, and IL-10. For NK cell renewal, intracellular BrdU staining was performed using anti-BrdU antibody (cloneBu20a). All antibodies and the corresponding isotype controls were fluorochrome-conjugated and purchased from eBioscience or BD Biosciences. Multi-colored Flow cytometry analyses were performed on an LSR II™ (BD). Data were analyzed with FlowJo™ software (Tree Star).

Histology and immunohistochemistry staining (IHC). Prostate, Lung, and other organs were sectioned and stained with H&E for histological evaluation. For immunohistochemistry staining to detect specific antigens, the following antibodies were used: anti-SV40T (Santa Cluz, clone v300), anti-Arginase I (Santa Cluz, clone H52), anti-Ki67 (Neomarker, clone SP6), anti-cleaved Caspase-3(cell signaling, clone 5A1E), anti-FoxP3, anti-CD8, anti-NK1.1 (PK136), and anti-synaptophysin. The IHC staining protocol has been previously described. All tissues were counter stained with Hemotoxyline for visualization of nucleus.

Serum sMIC and cytokine detection. Serum levels of sMICB were assessed using a MICB Sandwich ELISA kit (R&D systems). Serum levels of cytokines were assayed by Eve Technologies Corporation using the Luminex technology (Alberta, Canada).

Statistical analysis. All results are expressed as the mean±SEM. Mouse and sample group sizes were n>5, unless otherwise indicated. Data were analyzed using unpaired test, and differences were determined significant at $P<0.05$.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the score of the disclosure.

TABLE 2

| SEQ ID NO: | | |
|---|---|---|
| 1 | Light chain CDR1 | GCC CAC ATT AAT AAT TGG |
| 2 | Light chain CDR2 | GAT GCA ACC |
| 3 | Light chain CDR3 | CAA CAT TAT TGG AGT ACT CCG TGG ACG |
| 4 | Heavy chain CDR1 | GGC TAC TCA ATC ACC AGT GAT TAT GCC |
| 5 | Heavy chain CD2 | ATA AGC TAC AGT GGT AGC ACT |
| 6 | Heavy chain CDR3 | GCA AGG GGG GGG ACT TAC TTT GAC TAC |

TABLE 2-continued

| SEQ ID NO: | | |
|---|---|---|
| 9 | Light chain CDR1 | AHINNW |
| 10 | Light chain CDR2 | DAT |
| 11 | Light chain CDR3 | QHYWSTPWT |
| 12 | Heavy chain CDR1 | GYSITSDYA |
| 13 | Heavy chain CD2 | ISYSGST |
| 14 | Heavy chain CDR3 | ARGGTYFDY |

Example 4

Generation of Chimeric chB10G5 Antibody cDNA of the B10G5 light chain variable region (VL) was amplified by PCR. After sequence confirmation, the cDNA fragment of VL was in-frame fused to the constant region of human IgG1 light chain by cloning to the expression vector pFUSE2-CLIg-hk (InvivoGen). cDNA of the B10G5 heavy chain variable region (VH) of was amplified by PCR. The cDNA fragment with correct sequence of VH was in-frame fused to the constant region of human IgG1 heavy chain by cloning to the expression vector pFUSE-CHIg-hG1 (Invivogen). The two expression plasmids, bearing the hybrid VL and VH, were co-transfected into 293T cells. Expression and specificity of the hybrid antibody in the transfected 293 T culture supernatant was determined by flow cytometry with MIC-expressing cells (FIG. 24).

What is claimed:

1. An isolated antibody or antigen-binding portion thereof that specifically binds to a sMIC polypeptide comprising heavy and light chain complementarity determining regions (CDRs):
   a. a light chain CDR1 having the amino acid sequence of SEQ ID NO: 9;
   b. a light chain CDR2 having the amino acid sequence of SEQ ID NO: 10;
   c. a light chain CDR3 having the amino acid sequence of SEQ ID NO: 11;
   d. a heavy chain CDR1 having the amino acid sequence of SEQ ID NO: 12;
   e. a heavy chain CDR2 having the amino acid sequence of SEQ ID NO: 13; and
   f. a heavy chain CDR3 having the amino acid sequence of SEQ ID NO: 14.

2. The antibody or antigen-binding portion thereof of claim 1, wherein the antibody or antigen-binding portion thereof is selected from the group consisting of:
   an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a diabody, a multispecific antibody, a dual specific antibody, an anti-idiotypic antibody, and a bispecific antibody.

3. A pharmaceutical composition comprising an antibody or antigen-binding portion thereof of claim 1 and a pharmaceutically acceptable carrier.

4. A nucleic acid encoding an antibody or antigen-binding portion thereof of claim 1.

5. The nucleic acid of claim 4, wherein one or more of the nucleic acid sequences encoding the CDRs of the antibody or antigen-binding portion thereof are selected from the group consisting of SEQ ID NOs: 1-6.

6. The nucleic acid of claim 4, wherein the nucleic acid sequences encoding the CDRs of the antibody or antigen-binding portion thereof are SEQ ID NOs: 1-6.

7. The nucleic acid of claim 4, wherein the nucleic acid is a cDNA.

8. A method of inhibiting sMIC, the method comprising contacting a cell with or administering to a subject an antibody or antigen-binding portion thereof of claim 1.

9. A method of treating a MIC-positive cancer in a subject in need thereof, the method comprising administering an effective amount of a pharmaceutical composition of claim 3 to the subject.

10. The method of claim 9, wherein the MIC-positive cancer is an epithelial cell tumor.

11. The method of claim 9, wherein the MIC-positive cancer is a hematopoietic malignancy.

12. The method of claim 9, further comprising administering an additional immunotherapy.

13. The antibody or antigen-binding portion thereof of claim 1, comprising a light chain having the sequence of SEQ ID NO: 7.

14. The antibody or antigen-binding portion thereof of claim 13, further comprising a conservative substitution in a sequence not comprised by a CDR.

15. The antibody or antigen-binding portion thereof of claim 1, comprising a heavy chain having the sequence of SEQ ID NO: 8.

16. The antibody or antigen-binding portion thereof of claim 15, further comprising a conservative substitution in a sequence not comprised by a CDR.

* * * * *

SEQUENCE LISTING

<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcccacatta ataattgg                                                        18

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 gatgcaacc                                                                   9

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 3
caacattatt ggagtactcc gtggacg                                          27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggctactcaa tcaccagtga ttatgcc                                          27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ataagctaca gtggtagcac t                                                21

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcaagggggg ggacttactt tgactac                                          27

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Val Leu Thr Gln Thr Thr Ser Tyr Leu Ser Val Ser Leu Gly
1               5                   10                  15

Gly Arg Val Thr Ile Ala Cys Lys Ala Ser Ala His Ile Asn Asn Trp
            20                  25                  30

Leu Ala Trp Tyr Gln Gln Lys Pro Gly Asn Ala Pro Arg Leu Leu Ile
        35                  40                  45

Ser Asp Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln His Tyr Trp Ser Thr Pro Trp
                85                  90                  95

Thr Phe Gly Gly Gly Thr Lys Leu Glu Ile Lys Arg Ala Asp Ala Ala
            100                 105                 110

Pro Thr Val Ser
            115

```
<210> SEQ ID NO 8
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Pro Glu Val Gln Leu Glu Glu Ser Gly Pro Gly Leu Val Lys Pro
1               5                   10                  15

Ser Gln Ser Leu Ser Leu Thr Cys Thr Val Thr Gly Tyr Ser Ile Thr
            20                  25                  30

Ser Asp Tyr Ala Trp Asn Trp Ile Arg Gln Phe Pro Gly Asn Lys Leu
        35                  40                  45

Glu Trp Met Gly Tyr Ile Ser Tyr Ser Gly Ser Thr Asn Tyr Asn Pro
    50                  55                  60

Ser Leu Lys Ser Arg Ile Ser Ile Thr Arg Asp Thr Ser Lys Asn Gln
65                  70                  75                  80

Phe Phe Leu Gln Leu Asn Ser Val Ile Thr Glu Asp Thr Ala Thr Tyr
                85                  90                  95

Tyr Cys Ala Arg Gly Gly Thr Tyr Phe Asp Tyr Trp Gly Gln Gly Thr
            100                 105                 110

Thr Leu Thr Val Ser Ser Ala Lys Thr Thr Pro Pro Ser Val Tyr
        115                 120                 125

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala His Ile Asn Asn Trp
1               5

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ala Thr
1

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln His Tyr Trp Ser Thr Pro Trp Thr
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Tyr Ser Ile Thr Ser Asp Tyr Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ser Tyr Ser Gly Ser Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Gly Gly Thr Tyr Phe Asp Tyr
1               5

<210> SEQ ID NO 15
<211> LENGTH: 383
<212> TYPE: PRT
<213> ORGANISM: Homo sapiens

<400> SEQUENCE: 15

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Thr Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160
```

```
Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380

<210> SEQ ID NO 16
<211> LENGTH: 383
<212> TYPE: PRT
<213> ORGANISM: Homo sapiens

<400> SEQUENCE: 16

Met Gly Leu Gly Arg Val Leu Leu Phe Leu Ala Val Ala Phe Pro Phe
1               5                   10                  15

Ala Pro Pro Ala Ala Ala Glu Pro His Ser Leu Arg Tyr Asn Leu
            20                  25                  30

Met Val Leu Ser Gln Asp Gly Ser Val Gln Ser Gly Phe Leu Ala Glu
        35                  40                  45

Gly His Leu Asp Gly Gln Pro Phe Leu Arg Tyr Asp Arg Gln Lys Arg
    50                  55                  60

Arg Ala Lys Pro Gln Gly Gln Trp Ala Glu Asn Val Leu Gly Ala Lys
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
        115                 120                 125

Gly Ser Arg His Phe Tyr Tyr Asp Gly Glu Leu Phe Leu Ser Gln Asn
    130                 135                 140

Leu Glu Thr Gln Glu Ser Thr Val Pro Gln Ser Ser Arg Ala Gln Thr
145                 150                 155                 160
```

-continued

```
Leu Ala Met Asn Val Thr Asn Phe Trp Lys Glu Asp Ala Met Lys Thr
                165                 170                 175
Lys Thr His Tyr Arg Ala Met Gln Ala Asp Cys Leu Gln Lys Leu Gln
            180                 185                 190
Arg Tyr Leu Lys Ser Gly Val Ala Ile Arg Arg Thr Val Pro Pro Met
        195                 200                 205
Val Asn Val Thr Cys Ser Glu Val Ser Glu Gly Asn Ile Thr Val Thr
    210                 215                 220
Cys Arg Ala Ser Ser Phe Tyr Pro Arg Asn Ile Thr Leu Thr Trp Arg
225                 230                 235                 240
Gln Asp Gly Val Ser Leu Ser His Asn Thr Gln Gln Trp Gly Asp Val
                245                 250                 255
Leu Pro Asp Gly Asn Gly Thr Tyr Gln Thr Trp Val Ala Thr Arg Ile
            260                 265                 270
Arg Gln Gly Glu Glu Gln Arg Phe Thr Cys Tyr Met Glu His Ser Gly
        275                 280                 285
Asn His Gly Thr His Pro Val Pro Ser Gly Lys Ala Leu Val Leu Gln
    290                 295                 300
Ser Gln Arg Thr Asp Phe Pro Tyr Val Ser Ala Ala Met Pro Cys Phe
305                 310                 315                 320
Val Ile Ile Ile Ile Leu Cys Val Pro Cys Cys Lys Lys Lys Thr Ser
                325                 330                 335
Ala Ala Glu Gly Pro Glu Leu Val Ser Leu Gln Val Leu Asp Gln His
            340                 345                 350
Pro Val Gly Thr Gly Asp His Arg Asp Ala Ala Gln Leu Gly Phe Gln
        355                 360                 365
Pro Leu Met Ser Ala Thr Gly Ser Thr Gly Ser Thr Glu Gly Thr
    370                 375                 380

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 17

Gly Gly Gly Gly Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
1               5

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: CDS
<222> LOCATION: (1)..(348)

<400> SEQUENCE: 19 gac att gtg ctc acc cag act aca tcc tac ttg tct gta tct cta gga    48
Asp Ile Val Leu Thr Gln Thr Thr Ser Tyr Leu Ser Val Ser Leu Gly
1               5                   10                  15 ggc aga gtc acc att gct tgc aag gca agt gcc cac att aat aat tgg    96
Gly Arg Val Thr Ile Ala Cys Lys Ala Ser Ala His Ile Asn Asn Trp
                20                  25                  30 tta gcc tgg tat cag cag aaa cca gga aat gct cct agg ctc tta ata   144
Leu Ala Trp Tyr Gln Gln Lys Pro Gly Asn Ala Pro Arg Leu Leu Ile
            35                  40                  45 tct gat gca acc agt ttg gaa act ggg gtt cct tca aga ttc agt ggc   192
Ser Asp Ala Thr Ser Leu Glu Thr Gly Val Pro Ser Arg Phe Ser Gly
50                  55                  60 agt gga tct gga aag gat tac act ctc agc att acc agt ctt cag act   240
Ser Gly Ser Gly Lys Asp Tyr Thr Leu Ser Ile Thr Ser Leu Gln Thr
65                  70                  75                  80 gaa gat gtt gct act tat tac tgt caa cat tat tgg agt act ccg tgg   288
Glu Asp Val Ala Thr Tyr Tyr Cys Gln His Tyr Trp Ser Thr Pro Trp
                85                  90                  95 acg ttc ggt gga ggc acc aag ctg gaa atc aaa cgg gct gat gct gca   336
Thr Phe Gly Gly Gly Thr Lys Leu Glu Ile Lys Arg Ala Asp Ala Ala
                100                 105                 110 cca act gta tcc acc                                               351
Pro Thr Val Ser
        115

<210> SEQ ID NO 20
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(381)

<400> SEQUENCE: 20 ctt ccg gag gtc cag ctg gag gag tct gga cct ggc ctg gtg aaa ccc    48
Leu Pro Glu Val Gln Leu Glu Glu Ser Gly Pro Gly Leu Val Lys Pro
1               5                   10                  15 tct cag tct ctg tcc ctc acc tgc act gtc act ggc tac tca atc acc    96
Ser Gln Ser Leu Ser Leu Thr Cys Thr Val Thr Gly Tyr Ser Ile Thr
                20                  25                  30 agt gat tat gcc tgg aac tgg atc cgg cag ttt cca gga aac aaa ctg   144
Ser Asp Tyr Ala Trp Asn Trp Ile Arg Gln Phe Pro Gly Asn Lys Leu
            35                  40                  45 gag tgg atg ggc tac ata agc tac agt ggt agc act aac tac aac cca   192
Glu Trp Met Gly Tyr Ile Ser Tyr Ser Gly Ser Thr Asn Tyr Asn Pro
50                  55                  60 tct ctc aaa agt cga atc tct atc act cga gac acc tcc aag aac cag   240
Ser Leu Lys Ser Arg Ile Ser Ile Thr Arg Asp Thr Ser Lys Asn Gln
65                  70                  75                  80 ttc ttc ctg cag ttg aat tct gtg att act gag gac aca gcc aca tat   288
Phe Phe Leu Gln Leu Asn Ser Val Ile Thr Glu Asp Thr Ala Thr Tyr
                85                  90                  95 tac tgt gca agg ggg ggg act tac ttt gac tac tgg ggc caa ggc acc   336
Tyr Cys Ala Arg Gly Gly Thr Tyr Phe Asp Tyr Trp Gly Gln Gly Thr
                100                 105                 110
```

-continued

```
act ctc aca gtc tcc tca gcc aaa acg aca ccc cca tct gtc tat tc      383
Thr Leu Thr Val Ser Ser Ala Lys Thr Thr Pro Pro Ser Val Tyr
        115                 120                 125
```